(12) United States Patent
Guo et al.

(10) Patent No.: US 8,716,285 B2
(45) Date of Patent: May 6, 2014

(54) N-HYDROXY-BENZAMIDS FOR THE TREATMENT OF CANCER

(75) Inventors: Lei Guo, Shanghai (CN); Guozhi Tang, Shanghai (CN); Zhanguo Wang, Shanghai (CN); Jason Christopher Wong, Shanghai (CN); Weixing Zhang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 301 days.

(21) Appl. No.: 13/226,567

(22) Filed: Sep. 7, 2011

(65) Prior Publication Data

US 2012/0065204 A1   Mar. 15, 2012

(30) Foreign Application Priority Data

Sep. 9, 2010   (WO) ............... PCT/CN2010/076767

(51) Int. Cl.
| | | |
|---|---|---|
| A61K 31/535 | (2006.01) | |
| A61K 31/517 | (2006.01) | |
| A61K 31/505 | (2006.01) | |
| A61K 31/47 | (2006.01) | |
| A61K 31/44 | (2006.01) | |
| C07D 413/12 | (2006.01) | |
| C07D 239/72 | (2006.01) | |
| C07D 401/12 | (2006.01) | |
| C07D 215/38 | (2006.01) | |
| C07D 213/02 | (2006.01) | |
| C07D 211/70 | (2006.01) | |
| C07C 255/24 | (2006.01) | |

(52) U.S. Cl.
USPC ............... 514/235.8; 514/266.4; 514/272; 514/313; 514/347; 514/357; 514/604; 514/619; 544/122; 544/292; 544/330; 544/331; 546/159; 546/293; 546/335; 558/415

(58) Field of Classification Search
USPC ............ 514/235.8, 272, 313, 347, 357, 604, 514/619; 544/122, 292, 330, 331, 300; 546/159, 293, 335, 89; 558/415
See application file for complete search history.

(56) References Cited

U.S. PATENT DOCUMENTS

2012/0015943 A1* 1/2012 Blackburn et al. ......... 514/235.5

FOREIGN PATENT DOCUMENTS

| WO | 2005/108367 | 11/2005 |
|---|---|---|
| WO | 2009/112550 | 9/2009 |
| WO | 2010/151318 | 12/2010 |

OTHER PUBLICATIONS

Mahboobi et al., J. Med. Chem. 50:4405-4418 ( 2007).
Ansel et al. Pharmaceutical Dosage Forms and Drug Delivery Systems Sixth edition,:196, 456-457 ( 1995).
Hideshima et al., Proc. Natl. Acad. Sci. USA 102(24):8567-8572 ( 2005).
Miller et al., Journal of Medicinal Chemistry 46(25):5097-5116 ( 2003).
Bastin et al. Organic Process Research & Development vol. 4:427-435 ( 2000).
Koyama et al., Blood 96:1490-1495 ( 2000).
Keegan, Discovery on Target HDAC Inhibitor Conference, (2007).
Wong, J.C. et al., J. Am. Chem. Soc 125:5586-5587 ( 2003).
Matsuoka et al., Biochemical Pharmacology 74:465-476 ( 2007).
Kozikowski et al., J. Med. Chem. 51:4370-4373 ( 2008).
Haggarty et al., Proc. Natl. Acad. Sci. USA 100(8):4389-4394 ( 2003).
Oehme et al., Clinical Cancer Research 15:91-99 ( 2009).
Krennhrubec et al., Bioorganic & Medicinal Chemistry Letters 17:2874-2878 ( 2007).
Kawaguchi et al., Cell 115:727-738 ( 2003).
Martin et al., Oncogene 26:5450-5467 ( 2007).
Chen, Y. et al., J. Med. Chem. 51:3437-3448 ( 2008).
(International Search Report for PCT/EP2011/065245 Dec. 12, 2011).

* cited by examiner

*Primary Examiner* — James O Wilson
*Assistant Examiner* — Ebenezer O Sackey

(57) ABSTRACT

The present invention provides a compound of formula (I)

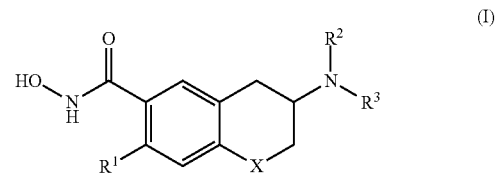

or a pharmaceutically acceptable salt, ester or stereoisomer thereof, wherein $R^1$ to $R^3$ and X have the significances given herein. The present invention is also directed to processes for making said compounds and uses of said compounds, in particular their use as medicaments, more particularly their use as medicaments in the treatment of cancer.

32 Claims, 2 Drawing Sheets

N-HYDROXY-BENZAMIDS FOR THE TREATMENT OF CANCER

PRIORITY TO RELATED APPLICATION(S)

This application claims the benefit of International Patent Application No. PCT/CN2010/076767, filed Sep. 9, 2010, which is hereby incorporated by reference in its entirety.

The invention relates to novel anti-tumor agents and pharmaceutically acceptable salts thereof, and processes for the manufacture of these novel compounds and medicaments containing them. The compounds of the invention have anti-proliferative and differentiation-inducing activity, which results in inhibition of tumor cell proliferation and induction of apoptosis. The invention also relates to the use of such compounds for the treatment of diseases such as cancer and for the manufacture of corresponding medicaments.

The invention relates in particular to (i) a compound of formula (I)

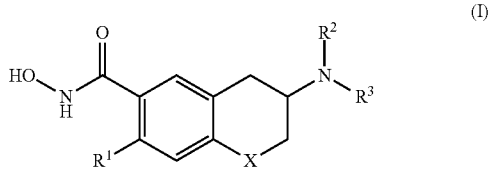

wherein
X is —CH$_2$—, oxygen or —NR$^4$;
R$^1$ is hydrogen or halogen;
R$^2$ is hydrogen; or
  alkyl, provided that X is —CH$_2$— or oxygen;
R$^3$ is phenyl, unsubstituted or once or twice substituted by halogen, nitro, alkyl, trifluoromethyl, dialkylamino, aminoalkyl, cyano or phenoxy;
  pyridin-2-yl, unsubstituted or once or twice substituted by nitro or trifluoromethyl;
  pyrimidin-2-yl, unsubstituted or once or twice substituted by alkyl, trifluoromethyl, alkoxy, phenoxy, pyridinyl, alkylpyridinyl, alkoxypyridinyl, halopyridinyl, morpholinylpyridinyl, naphthyl, quinolinyl, phenyl or substituted phenyl, wherein substituted phenyl is phenyl once or twice substituted by alkyl, halogen, dialkylamino, nitro, alkoxy, trifluoromethyl or phenoxy;
  quinazolin-2-yl, unsubstituted or once or twice substituted by halogen;
  phenylalkenylcarbonyl;
  phenylalkylcarbonyl;
  phenylalkoxycarbonyl;
  phenylcarbonyl, unsubstituted or once or twice substituted by halogen, alkyl, trifluoromethyl, alkoxy, trifluoromethoxy, cyano, dialkylamino or phenyl;
  pyridinylalkenylcarbonyl;
  pyridinylalkylcarbonyl;
  pyridinylalkoxycarbonyl;
  alkylsulfonyl;
  phenylsulfonyl, wherein phenyl is unsubstituted or once or twice substituted by halogen, trifluoromethyl, trifluoromethoxy, alkoxy, cyano, dialkylamino or dialkylaminoalkyl;
  or pyridinylsulfonyl;
R$^4$ is hydrogen or alkyl;
or a pharmaceutically acceptable salt, ester or stereoisomers thereof.

The invention also relates to a process for the manufacture of these novel compounds and medicaments containing them.

Histone deacetylases (HDACs) are one of the major classes of post-translational regulators and have been implicated in pro-growth, anti-apoptotic, and anti-differentiation roles in various cancer types. As the key enzymatic components of multiprotein complexes, histone deacetylases (HDACs) are responsible for deacetylation of lysine residues in histone and nonhistone protein substrates. Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., *Blood* 2000, 96, 1490-1495).

HDAC proteins comprise a family of 18 members in humans with homologies to yeast HDACs, Rpd3, Hda1, and Sir2. Based on their sequence similarity, cellular localization tendencies, tissue expression patterns, and enzymatic mechanisms, the HDACs can thus be divided into four classes. The class I HDACs (HDACs 1, 2, 3, and 8), homologous to Rpd3, localize primarily in the nucleus and appear to be ubiquitously expressed in most tissues. The class II HDACs (HDACs 4, 5, 6, 7, 9, 10), homologous to Hda1, are able to shuttle between the nucleus and the cytoplasm depending on a variety of regulatory signals and cellular state, and are expressed in a more limited number of cell types. These HDACs can be further subdivided into class IIa (HDACs 4, 5, 7, 9), and class IIb (HDACs 6, 10). HDAC11 is the sole member of class IV histone deacetylase. Class I, II, and IV HDACs are all zinc-dependent deacetylases. In contrast, the class III HDACs, homologous to Sir2, are NAD+-dependent deacetylases that are mechanistically distinct from the class I and II HDACs and are not inhibited by classical HDAC inhibitors such as trichostatin A, trapoxin B, or MS-275.

Given their association with cancer formation, class I and II HDAC proteins have emerged as attractive targets for anti-cancer therapy. The class I HDACs in particular have been closely associated with anti-proliferative effects against tumor cells. For example, pharmacological inhibition of HDACs 1-3 leads to induction of the cyclin-dependent kinase inhibitor p21 and concomitant cell cycle arrest. Several HDAC inhibitor (HDACi) drugs are in various stages of clinical trials, with SAHA (suberoylanilide hydroxamic acid, Vorinostat) and Romidepsin (FK228) gaining FDA approval in 2006 and 2009 respectively, for the treatment of cutaneous T-cell lymphoma (CTCL). Recently, the expression of HDAC8 (and not any other HDAC isoforms) was shown to significantly and independently correlate with the disease stage and poor survival of neuroblastoma (NB), which is a neoplasm of the peripheral autonomic nervous system that represents the second most common malignancy of childhood. Furthermore, knockdown of HDAC8 by siRNA led to NB cell differentiation and inhibited cell growth while its overexpression blocked retinoic acid-induced NB differentiation (*Clinical Cancer Research* 2009, 15, 91-99). HDAC8 is therefore a potential drug target for the differentiation therapy of minimal residual disease in NB. In addition, a possible correlation between HDAC8 and acute myeloid leukemia (AML) has also been suggested (*Bioorg. Med. Chem. Lett.* 2007, 17, 2874). Unlike class I HDACs which are predominantly nuclear enzymes, class IIa enzymes shuttle between the nucleus and cytoplasm, and are known to associate with the HDAC3/SMRT/N-CoR complex and MEF2 and as such have important roles in regulating muscle cell gene expression (reviewed in *Oncogene* 2007, 26, 5450-

5467) and the immune response (*Biochemical Pharmacology* 2007, 74, 465-476). The IIb subclass enzymes uniquely feature two deacetylase domains, and are primarily cytoplasmic. Significantly, HDAC6 operates on a variety of substrates other than histone proteins, and is involved in processing Lys40 of the mitotic spindle protein α-tubulin. HDAC6 also has a dynein motor binding domain to enable HDAC6 to shuttle cargo along the microtubule, and a zinc finger ubiquitin-binding domain at the C-terminus. Through its ubiquitin-binding activity, HDAC6 is able to mediate the recruitment of autophagic material to aggresomes for degradation, thus decreasing the cytotoxic effects of these aggregates (*Cell* 2003, 115, 727-738). Inhibition of HDAC6 activity by the specific inhibitor, tubacin, can increase accumulation of acetylated α-tubulin and inhibit cell motility without affecting microtubule stability per se (*J. Am. Chem. Soc.* 2003, 125, 5586-5587, *Proc. Nat. Acad. Sci. USA* 2003, 4389-4394).

Multiple myeloma (MM) is a plasma cell malignancy characterized by complex heterogeneous cytogenetic abnormalities and infiltration of malignant cells into the bone marrow, leading to bone disease, hypercalcemia, cytopenia, renal dysfunction, hyperviscosity and peripheral neuropathy. Standard proteasome inhibitor-based therapies have achieved remarkable response rates in MM, however combination therapies with new targeted drugs are still needed due to the development of drug resistance and poor long-term survival. It was recently demonstrated that concomitant proteasome and HDAC6 inhibition can lead to synergistic anti-proliferative effects in MM cells, most likely due to the role of HDAC6 in mediating aggresome function and the ensuing misfolded protein stress that develops as a result of dual proteasome/aggresome inhibition (*Proc. Nat. Acad. Sci. USA* 2005, 102, 8567-8572). HDAC6 is therefore an attractive novel target for the development of new MM combination therapies.

The compounds according to this invention are inhibitors of HDAC6 or HDAC8 and therefore show anti-proliferative and differentiation-inducing activities, which result in inhibition of tumor cell proliferation and induction of apoptosis. Pan HDAC inhibitors have broad spectrum preclinical activity against a wide range of cancer types, yet also possess non-specific cytotoxicity which may limit their clinical application. In contrast, HDAC inhibitors targeted toward specific isoforms, especially HDAC6 and HDAC8, typically show lower non-specific cytotoxicity and can be suitable for the treatment of certain cancer subtypes. The compounds of the present invention show enhanced selectivity toward HDAC6 or HDAC8 compared with the pan HDAC inhibitor SAHA, as assessed by both enzymatic and in-cell assays.

Based on different zinc binding groups, four major classes of HDAC inhibitors have been extensively described in the literature: (1) hydroxamic acids; (2) ortho-aminoanilides; (3) thiols or their prodrugs; (4) carboxylic acids and their analogues (reviewed in *J. Med. Chem.* 2003, 46, 5097-5116). In general, the hydroxamic acids such as SAHA, LBH589, PXD101, JNJ26481585 and ITF2357 display broad inhibitory activity against most HDAC isoforms in the submicromolar range (*J. Med. Chem.* 2007, 50, 4405). On the other hand, the ortho-aminoanilides exemplified by MS275 and its aryl substituted analog show high potency and class I activity confined primarily to the HDAC 1, 2, 3 subtypes. The thiol prodrug FK228 (depsipeptide/Romidepsin) also has been reported to have similar class I selectivity, although the drug's developer, Gloucester pharmaceuticals, has claimed that the molecule is a pan-HDAC inhibitor (Mitchell Keegan, *Discovery On Target HDAC Inhibitor Conference* 2007). In contrast, the fatty acid class are the least potent of the HDAC inhibitors, with enzyme inhibitory values in the high micromolar ranges.

Limited reports confined to the realm of hydroxamic acid-based molecules have been published describing compounds with HDAC6 and/or HDAC8 selectivity. Tubacin is the prototype HDAC6 selective inhibitor with a bulky capping group contacting the rim region of HDAC6. Kozikowski et al. have described potent HDAC6-selective triazolylphenyl capped hydroxamates and related phenylisoxazole capped hydroxamate inhibitors with greater than 50 fold selectivity over HDAC1 and HDAC3 (*J. Med. Chem.* 2008, 51, 3437 and *J. Med. Chem.* 2008, 51, 4370). In all instances, the inhibitors have rigid and bulky capping groups as selectivity elements and those capping groups are linked with zinc binding hydroxamic acids through flexible aliphatic chains. In a different approach, Envivo Pharmaceuticals disclosed 1,2,3,4-tetrahydroisoquinoline hydroxamates for potential treatment of neurodegenerative diseases (WO2005/108367), but their HDAC isoform selectivity has yet to be clarified. Most recently, Smil et. al. from MethylGene Inc. reported chiral 3,4-dihydroquinoxalin-2(1H)-one and piperazine-2,5-dione aryl hydroxamates with selectivity (up to 40-fold) for human HDAC6 over other class I/IIa HDACs. The compounds of the present invention employ rigid tetrahydronaphthylene, 1,2,3,4-tetrahydroquinoline and chroman as linker between the zinc-binding hydroxamic acid group and rim-binding capping groups. They demonstrate submicromolar to micromolar inhibition of HDAC6 or HDAC8 based on their in-cell tubulin acetylation induction activity (HDAC6 in-cell assay) and enzymatic inhibition of HDAC8. Compounds from the present invention are able to induce obvious NB cell differentiation. Compounds from the present invention also demonstrate synergy when combined with bortezomib in cell growth inhibition of MM cell lines. As a surrogate for in-cell HDAC1/2/3 inhibition, p21 induction was used as a counter-screen to evaluate the selectivity of the compounds in the present invention toward HDAC6 or HDAC8 over HDACs 1, 2, and 3. In contrast to positive controls MS275 and SAHA, none of the compounds of the present invention showed significant or comparable p21 induction activity at 3 μM, 10 μM, and 30 μM concentrations. The compounds of the present invention are potent and selective HDAC6 or HDAC8 inhibitors that could be particularly suitable for the treatment of multiple myeloma and neuroblastoma, based upon the emerging biology of HDAC6 and HDAC8 in these two cancer types.

It has been found that the compounds of the present invention are HDAC6 or HDAC8 inhibitors which have anti-proliferative and differentiation-inducing activity, resulting in inhibition of tumor cell proliferation and induction of apoptosis. These compounds are therefore useful for the treatment of diseases such as neuroblastoma and multiple myeloma in humans or animals.

As used herein, the term "alkyl", alone or in combination, signifies a saturated, linear- or branched chain alkyl group containing 1 to 8, preferably 1 to 6, more preferably 1 to 4 carbon atoms, for example methyl, ethyl, propyl, isopropyl, 1-butyl, 2-butyl and tert-butyl. Preferred "alkyl" groups are methyl, ethyl, isopropyl and tert-butyl.

The term "alkenyl", alone or in combination, signifies an alkyl group as defined above wherein one or more carbon-carbon single bond is replaced by a carbon-carbon double bond. Examples of alkenyl are ethenyl, propenyl, n-butenyl and i-butenyl. Preferred alkenyl groups are ethenyl, propenyl and i-propenyl.

The term "alkoxy", alone or in combination, signifies a group alkyl-O—, wherein the "alkyl" is as defined above; for example methoxy, ethoxy, propoxy, isopropoxy, n-butoxy, i-butoxy, 2-butoxy and t-butoxy. Preferred alkoxy groups are methoxy and ethoxy and more preferably methoxy.

The term "halogen" means fluorine, chlorine, bromine or iodine. Halogen is preferably fluorine, chlorine or bromine.

The term "halophenyl" means phenyl substituted by halogen.

The term "halopyridinyl" means pyridinyl substituted by halogen.

The term "carbonyl", alone or in combination, refers to the group —C(O)—.

The term "amino", alone or in combination, refers to primary (—NH$_2$), secondary (—NH—) or tertiary amino

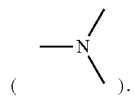

The term "nitro" refers to the group —NO$_2$.

The term "sulfonyl", alone or in combination, refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as acetate esters, propionate esters, benzoate esters and pivalate esters. Additionally, any physiologically acceptable equivalents of the compounds of general formula (I), similar to the metabolically labile esters, which are capable of producing the parent compounds of general formula (I) in vivo, are within the scope of this invention. Preferred are the acetyl, propionyl, and benzoyl esters of the compounds of formula (I).

Compounds of the general formula (I) which contain one or several chiral centers can either be present as racemates, diastereomeric mixtures, or optically active single isomers. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The term "MS-275" as used herein is otherwise also known as "SNDX-275" or "Entinostat", and has the chemical name Pyridin-3-ylmethyl N-[[4-[(2-aminophenyl)carbamoyl]phenyl]methyl]carbamate.

Another embodiment of present invention is (ii) a compound of formula (I) or a pharmaceutically acceptable salt, ester or stereoisomers thereof, wherein
X is —CH$_2$—, oxygen or —NR$^4$;
R$^1$ is hydrogen or halogen;
R$^2$ is hydrogen; or
  alkyl, provided that X is —CH$_2$— or oxygen;
R$^3$ is phenyl, unsubstituted or once or twice substituted by halogen, nitro or cyano;
  pyridin-2-yl, unsubstituted or once substituted by nitro;
  pyrimidin-2-yl, unsubstituted or once or twice substituted by alkyl, trifluoromethyl, alkoxy, phenoxy, pyridinyl, alkylpyridinyl, alkoxypyridinyl, halopyridinyl, morpholinylpyridinyl, naphthyl, quinolinyl, phenyl or substituted phenyl, wherein substituted phenyl is phenyl once or twice substituted by alkyl, halogen, dialkylamino, alkoxy, trifluoromethyl or phenoxy;
  quinazolin-2-yl substituted by halogen;
  alkoxyphenylcarbonyl;
  halophenylcarbonyl;
  trifluoromethylphenylcarbonyl;
  phenylphenylcarbonyl;
  pyridinylalkenylcarbonyl;
  pyridinylalkoxycarbonyl;
  alkylsulfonyl;
  phenylsulfonyl, wherein phenyl is once or twice substituted by halogen, trifluoromethyl, trifluoromethoxy or alkoxy;
  or pyridinylsulfonyl;
R$^4$ is hydrogen or alkyl.

Further particular embodiment of the invention is (iii) a compound of formula (I) or a pharmaceutically acceptable salt, ester or stereoisomers thereof, wherein R$^1$ is hydrogen or fluoro; and all remaining substituents have the significances given before.

Further particular embodiment of the invention is (iv) a compound of formula (I) or a pharmaceutically acceptable salt, ester or stereoisomers thereof, wherein R$^1$ is hydrogen; and all remaining substituents have the significances given before.

Further particular embodiment of the invention is (v) a compound of formula (I) or a pharmaceutically acceptable salt, ester or stereoisomers thereof, wherein R$^1$ is fluoro; and all remaining substituents have the significances given before.

Another particular embodiment of the invention is (vi) a compound of formula (I) or a pharmaceutically acceptable salt, ester or stereoisomers thereof, wherein R$^2$ is hydrogen; or methyl, provided that X is —CH$_2$— or oxygen; and all remaining substituents have the significances given before.

A further particular embodiment of the invention is (vii) a compound of formula (I) or a pharmaceutically acceptable salt, ester or stereoisomers thereof, wherein R$^2$ is hydrogen; and all remaining substituents have the significances given before.

Still another particular embodiment of the invention is (viii) a compound of formula (I) or a pharmaceutically acceptable salt, ester or stereoisomers thereof, wherein
R$^3$ is phenyl, unsubstituted or once or twice substituted by fluoro, chloro, bromo, nitro or cyano;

pyridin-2-yl, unsubstituted or once substituted by nitro;
pyrimidin-2-yl, unsubstituted or once or twice substituted by methyl, trifluoromethyl, ethoxy, phenoxy, pyridinyl, methylpyridinyl, methoxypyridinyl, chloropyridinyl, morpholinylpyridinyl, naphthyl, quinolinyl, phenyl or substituted phenyl wherein substituted phenyl is phenyl once or twice substituted by methyl, fluoro, chloro, dimethylamino, methoxy, trifluoromethyl or phenoxy;
fluoroquinazolin-2-yl;
pyridinylethylenylcarbonyl;
pyridinylmethoxycarbonyl;
methoxyphenylcarbonyl;
chlorophenylcarbonyl;
trifluoromethylphenylcarbonyl;
phenylphenylcarbonyl;
butylsulfonyl;
phenylsulfonyl, wherein phenyl is once or twice substituted by fluoro, chloro, trifluoromethyl, trifluoromethoxy or methoxy;
or pyridinylsulfonyl;
and all remaining substituents have the significances given before.

A particular embodiment of the invention is (ix) a compound of formula (I) or a pharmaceutically acceptable salt, ester or stereoisomers thereof, wherein
$R^3$ is phenyl, unsubstituted or once or twice substituted by bromo;
pyrimidin-2-yl, unsubstituted or once or twice substituted by methyl, trifluoromethyl, ethoxy, pyridinyl, methylpyridinyl, methoxypyridinyl, chloropyridinyl, morpholinylpyridinyl, quinolinyl, phenyl or substituted phenyl wherein substituted phenyl is phenyl once or twice substituted by methyl, fluoro, chloro, dimethylamino or methoxy;
fluoroquinazolin-2-yl;
pyridinylethoxycarbonyl;
methoxyphenylcarbonyl;
butylsulfonyl;
or phenylsulfonyl, wherein phenyl is once or twice substituted by fluoro, chloro, trifluoromethyl or methoxy;
and all remaining substituents have the significances given before.

Another particular embodiment of the invention is (x) a compound of formula (I) or a pharmaceutically acceptable salt, ester or stereoisomers thereof, wherein $R^4$ is hydrogen or methyl; and all remaining substituents have the significances given before.

A further particular embodiment of the invention is (xi) a compound of formula (I) or a pharmaceutically acceptable salt, ester or stereoisomers thereof, wherein X is —$CH_2$—.

Particular compounds of formula (I) or a pharmaceutically acceptable salt, ester or stereoisomers thereof, according to the invention can be selected from
7-(4-fluoro-phenylamino)-5,6,7,8-tetrahydro-naphthalene-2-carboxylic acid hydroxyamide;
7-(4-bromo-phenylamino)-5,6,7,8-tetrahydro-naphthalene-2-carboxylic acid hydroxyamide;
7-(4-nitro-phenylamino)-5,6,7,8-tetrahydro-naphthalene-2-carboxylic acid hydroxyamide;
7-(3-chloro-4-cyano-phenylamino)-5,6,7,8-tetrahydro-naphthalene-2-carboxylic acid hydroxyamide;
7-(pyridin-2-ylamino)-5,6,7,8-tetrahydro-naphthalene-2-carboxylic acid hydroxyamide;
7-(5-nitro-pyridin-2-ylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide;
7-(4-Phenyl-pyrimidin-2-ylamino)-5,6,7,8-tetrahydro-naphthalene-2-carboxylic acid hydroxyamide;
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(4-chloro-phenyl)-pyrimidin-2-ylamino]-5,6,7,8-tetrahydro-naphthalene-2-carboxylic acid hydroxyamide;
7-[4-(3-chloro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide;
7-[4-(2-fluoro-4-methyl-phenyl)-pyrimidin-2-ylamino]-5,6,7,8-tetrahydro-naphthalene-2-carboxylic acid hydroxyamide;
7-[4-(2,4-Dimethoxy-phenyl)-pyrimidin-2-ylamino]-5,6,7,8-tetrahydro-naphthalene-2-carboxylic acid hydroxyamide;
7-[4-(4-Trifluoromethyl-phenyl)-pyrimidin-2-ylamino]-5,6,7,8-tetrahydro-naphthalene-2-carboxylic acid hydroxyamide;
7-[4-(2,4-Dichloro-phenyl)-pyrimidin-2-ylamino]-5,6,7,8-tetrahydro-naphthalene-2-carboxylic acid hydroxyamide;
7-[4-(4-chloro-2-methyl-phenyl)-pyrimidin-2-ylamino]-5,6,7,8-tetrahydro-naphthalene-2-carboxylic acid hydroxyamide;
7-[4-(3-Chloro-4-fluoro-phenyl)-pyrimidin-2-ylamino]-5,6,7,8-tetrahydro-naphthalene-2-carboxylic acid hydroxyamide;
7-[4-(4-Phenoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Methoxy-pyridin-3-yl)-pyrimidin-2-ylamino]-5,6,7,8-tetrahydro-naphthalene-2-carboxylic acid hydroxyamide;
7-[4-(6-Chloro-pyridin-3-yl)-pyrimidin-2-ylamino]-5,6,7,8-tetrahydro-naphthalene-2-carboxylic acid hydroxyamide;
7-[4-(2-Chloro-pyridin-3-yl)-pyrimidin-2-ylamino]-5,6,7,8-tetrahydro-naphthalene-2-carboxylic acid hydroxyamide;
7-[4-(6-Morpholin-pyridin-3-yl)-pyrimidin-2-ylamino]-5,6,7,8-tetrahydro-naphthalene-2-carboxylic acid hydroxyamide;
7-(4-Methyl-6-phenoxy-pyrimidin-2-ylamino)-5,6,7,8-tetrahydro-naphthalene-2-carboxylic acid hydroxyamide;
7-(4-Naphthalen-2-yl-pyrimidin-2-ylamino)-5,6,7,8-tetrahydro-naphthalene-2-carboxylic acid hydroxyamide;
7-(4-Quinolin-3-yl-pyrimidin-2-ylamino)-5,6,7,8-tetrahydro-naphthalene-2-carboxylic acid hydroxyamide;
7-(6-Fluoro-quinazolin-2-ylamino)-5,6,7,8-tetrahydro-naphthalene-2-carboxylic acid hydroxyamide;
7-[Methyl-(4-pyridin-3-ylpyrimidin-2-yl)-amino]-5,6,7,8-tetrahydro-naphthalene-2-carboxylic acid hydroxyamide;

7-(3-Pyridin-3-yl-acryloylamino)-5,6,7,8-tetrahydro-naphthalene-2-carboxylic acid hydroxyamide;
7-(Hydroxycarbamoyl-1,2,3,4-tetrahydro-naphthalen-2-yl)-carbamic acid pyridin-3-ylmethyl ester;
7-(Butane-1-sulfonylamino)-5,6,7,8-tetrahydro-naphthalene-2-carboxylic acid hydroxyamide;
7-(3-Fluoro-benzenesulfonylamino)-5,6,7,8-tetrahydro-naphthalene-2-carboxylic acid hydroxyamide;
7-(4-Chloro-benzenesulfonylamino)-5,6,7,8-tetrahydro-naphthalene-2-carboxylic acid hydroxyamide;
7-(3-Chloro-benzenesulfonylamino)-5,6,7,8-tetrahydro-naphthalene-2-carboxylic acid hydroxyamide;
7-(3-Trifluoromethyl-benzenesulfonylamino)-5,6,7,8-tetrahydro-naphthalene-2-carboxylic acid hydroxyamide;
7-(2,4-Difluoro-benzenesulfonylamino)-5,6,7,8-tetrahydro-naphthalene-2-carboxylic acid hydroxyamide;
7-(3,4-Dimethoxy-benzenesulfonylamino)-5,6,7,8-tetrahydro-naphthalene-2-carboxylic acid hydroxyamide;
7-(2,4-Dichloro-benzenesulfonylamino)-5,6,7,8-tetrahydro-naphthalene-2-carboxylic acid hydroxyamide;
7-(3,4-Dichloro-benzenesulfonylamino)-5,6,7,8-tetrahydro-naphthalene-2-carboxylic acid hydroxyamide;
7-(Pyridine-3-sulfonylamino)-5,6,7,8-tetrahydro-naphthalene-2-carboxylic acid hydroxyamide;
3-Fluoro-7-(pyrimidin-2-ylamino)-5,6,7,8-tetrahydro-naphthalene-2-carboxylic acid hydroxyamide;
3-Fluoro-7-(4-phenyl-pyrimidin-2-ylamino)-5,6,7,8-tetrahydro-naphthalene-2-carboxylic acid hydroxyamide;
7-(4-Chloro-benzenesulfonylamino)-3-fluoro-5,6,7,8-tetrahydro-naphthalene-2-carboxylic acid hydroxyamide;
7-(3-Chloro-benzenesulfonylamino)-3-fluoro-5,6,7,8-tetrahydro-naphthalene-2-carboxylic acid hydroxyamide;
3-(Pyridin-3-yl-pyrimidine-2-ylamino)-1,2,3,4-tetrahydro-quinoline-6-carboxylic acid hydroxyamide;
3-(3-Methoxy-benzoylamino)-1,2,3,4-tetrahydro-quinoline-6-carboxylic acid hydroxyamide;
3-(4-Chloro-benzoylamino)-1,2,3,4-tetrahydro-quinoline-6-carboxylic acid hydroxyamide;
3-(3-Chloro-benzoylamino)-1,2,3,4-tetrahydro-quinoline-6-carboxylic acid hydroxyamide;
3-(3-Trifluoromethyl-benzoylamino)-1,2,3,4-tetrahydro-quinoline-6-carboxylic acid hydroxyamide;
3-(3,4-Dichloro-benzoylamino)-1,2,3,4-tetrahydro-quinoline-6-carboxylic acid hydroxyamide;
3-[(Biphenyl-4-carbonyl)-amino]-1,2,3,4-tetrahydro-quinoline-6-carboxylic acid hydroxyamide;
3-(3-Fluoro-benzenesulfonylamino)-1,2,3,4-tetrahydro-quinoline-6-carboxylic acid hydroxyamide;
3-(3-Chloro-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide;
3-(3-Trifluoromethyl-benzenesulfonylamino)-1,2,3,4-tetrahydro-quinoline-6-carboxylic acid hydroxyamide;
3-(3,4-Dimethoxy-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide; and
3-(4-Pyridin-3-yl-pyrimidin-2-ylamino)-chroman-6-6-carboxylic acid hydroxyamide.

Further particular compounds of formula (I) or a pharmaceutically acceptable salt, ester or stereoisomers thereof, according to the invention can be selected from can be selected from
7-(4-bromo-phenylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide;
7-(4-Phenyl-pyrimidin-2-ylamino)-5,6,7,8-tetrahydro-naphthalene-2-carboxylic acid hydroxyamide;
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide;
7-[4-(2-fluoro-4-methyl-phenyl)-pyrimidin-2-ylamino]-5,6,7,8-tetrahydro-naphthalene-2-carboxylic acid hydroxyamide;
7-[4-(2,4-Dimethoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Chloro-pyridin-3-yl)-pyrimidin-2-ylamino]-5,6,7,8-tetrahydro-naphthalene-2-carboxylic acid hydroxyamide;
7-[4-(2-Chloro-pyridin-3-yl)-pyrimidin-2-ylamino]-5,6,7,8-tetrahydro-naphthalene-2-carboxylic acid hydroxyamide;
7-[4-(6-Morpholin-pyridin-3-yl)-pyrimidin-2-ylamino]-5,6,7,8-tetrahydro-naphthalene-2-carboxylic acid hydroxyamide;
7-(4-Quinolin-3-yl-pyrimidin-2-ylamino)-5,6,7,8-tetrahydro-naphthalene-2-carboxylic acid hydroxyamide;
7-(6-Fluoro-quinazolin-2-ylamino)-5,6,7,8-tetrahydro-naphthalene-2-carboxylic acid hydroxyamide;
7-(Hydroxycarbamoyl-1,2,3,4-tetrahydro-naphthalen-2-yl)-carbamic acid pyridin-3-ylmethyl ester;
7-(Butane-1-sulfonylamino)-5,6,7,8-tetrahydro-naphthalene-2-carboxylic acid hydroxyamide;
7-(3-Fluoro-benzenesulfonylamino)-5,6,7,8-tetrahydro-naphthalene-2-carboxylic acid hydroxyamide;
7-(4-Chloro-benzenesulfonylamino)-5,6,7,8-tetrahydro-naphthalene-2-carboxylic acid hydroxyamide;
7-(3-Chloro-benzenesulfonylamino)-5,6,7,8-tetrahydro-naphthalene-2-carboxylic acid hydroxyamide;
7-(3-Trifluoromethyl-benzenesulfonylamino)-5,6,7,8-tetrahydro-naphthalene-2-carboxylic acid hydroxyamide;
7-(2,4-Difluoro-benzenesulfonylamino)-5,6,7,8-tetrahydro-naphthalene-2-carboxylic acid hydroxyamide;
7-(3,4-Dimethoxy-benzenesulfonylamino)-5,6,7,8-tetrahydro-naphthalene-2-carboxylic acid hydroxyamide;
7-(3,4-Dichloro-benzenesulfonylamino)-5,6,7,8-tetrahydro-naphthalene-2-carboxylic acid hydroxyamide;
3-Fluoro-7-(4-phenyl-pyrimidin-2-ylamino)-5,6,7,8-tetrahydro-naphthalene-2-carboxylic acid hydroxyamide;
7-(3-Chloro-benzenesulfonylamino)-3-fluoro-5,6,7,8-tetrahydro-naphthalene-2-carboxylic acid hydroxyamide;
3-(Pyridin-3-yl-pyrimidine-2-ylamino)-1,2,3,4-tetrahydro-quinoline-6-carboxylic acid hydroxyamide;

3-(3-Methoxy-benzoylamino)-1,2,3,4-tetrahydro-quinoline-6-carboxylic acid hydroxyamide;
3-(3-Fluoro-benzenesulfonylamino)-1,2,3,4-tetrahydro-quinoline-6-carboxylic acid hydroxyamide;
3-(3-Chloro-benzenesulfonylamino)-1,2,3,4-tetrahydro-quinoline-6-carboxylic acid hydroxyamide;
3-(3,4-Dimethoxy-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide; and
3-(4-Pyridin-3-yl-pyrimidin-2-ylamino)-chroman-6-6-carboxylic acid hydroxyamide.

The following compounds show activity as HDAC6 inhibitors and are particularly preferred according to the present invention 7-(4-fluoro-phenylamino)-5,6,7,8-tetrahydro-naphthalene-2-carboxylic acid hydroxyamide;
7-(4-bromo-phenylamino)-5,6,7,8-tetrahydro-naphthalene-2-carboxylic acid hydroxyamide;
7-(4-nitro-phenylamino)-5,6,7,8-tetrahydro-naphthalene-2-carboxylic acid hydroxyamide;
7-(3-chloro-4-cyano-phenylamino)-5,6,7,8-tetrahydro-naphthalene-2-carboxylic acid hydroxyamide;
7-(pyridin-2-ylamino)-5,6,7,8-tetrahydro-naphthalene-2-carboxylic acid hydroxyamide;
7-(5-nitro-pyridin-2-ylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide;
7-(4-Phenyl-pyrimidin-2-ylamino)-5,6,7,8-tetrahydro-naphthalene-2-carboxylic acid hydroxyamide;
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(4-chloro-phenyl)-pyrimidin-2-ylamino]-5,6,7,8-tetrahydro-naphthalene-2-carboxylic acid hydroxyamide;
7-[4-(3-chloro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide;
7-[4-(2-fluoro-4-methyl-phenyl)-pyrimidin-2-ylamino]-5,6,7,8-tetrahydro-naphthalene-2-carboxylic acid hydroxyamide;
7-[4-(2,4-Dimethoxy-phenyl)-pyrimidin-2-ylamino]-5,6,7,8-tetrahydro-naphthalene-2-carboxylic acid hydroxyamide;
7-[4-(4-Trifluoromethyl-phenyl)-pyrimidin-2-ylamino]-5,6,7,8-tetrahydro-naphthalene-2-carboxylic acid hydroxyamide;
7-[4-(2,4-Dichloro-phenyl)-pyrimidin-2-ylamino]-5,6,7,8-tetrahydro-naphthalene-2-carboxylic acid hydroxyamide;
7-[4-(4-chloro-2-methyl-phenyl)-pyrimidin-2-ylamino]-5,6,7,8-tetrahydro-naphthalene-2-carboxylic acid hydroxyamide;
7-[4-(3-Chloro-4-fluoro-phenyl)-pyrimidin-2-ylamino]-5,6,7,8-tetrahydro-naphthalene-2-carboxylic acid hydroxyamide;
7-[4-(4-Phenoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Methoxy-pyridin-3-yl)-pyrimidin-2-ylamino]-5,6,7,8-tetrahydro-naphthalene-2-carboxylic acid hydroxyamide;
7-[4-(6-Chloro-pyridin-3-yl)-pyrimidin-2-ylamino]-5,6,7,8-tetrahydro-naphthalene-2-carboxylic acid hydroxyamide;
7-[4-(2-Chloro-pyridin-3-yl)-pyrimidin-2-ylamino]-5,6,7,8-tetrahydro-naphthalene-2-carboxylic acid hydroxyamide;
7-[4-(6-Morpholin-pyridin-3-yl)-pyrimidin-2-ylamino]-5,6,7,8-tetrahydro-naphthalene-2-carboxylic acid hydroxyamide;
7-(4-Methyl-6-phenoxy-pyrimidin-2-ylamino)-5,6,7,8-tetrahydro-naphthalene-2-carboxylic acid hydroxyamide;
7-(4-Naphthalen-2-yl-pyrimidin-2-ylamino)-5,6,7,8-tetrahydro-naphthalene-2-carboxylic acid hydroxyamide;
7-(4-Quinolin-3-yl-pyrimidin-2-ylamino)-5,6,7,8-tetrahydro-naphthalene-2-carboxylic acid hydroxyamide;
7-(6-Fluoro-quinazolin-2-ylamino)-5,6,7,8-tetrahydro-naphthalene-2-carboxylic acid hydroxyamide;
7-[Methyl-(4-pyridin-3-ylpyrimidin-2-yl)-amino]-5,6,7,8-tetrahydro-naphthalene-2-carboxylic acid hydroxyamide;
7-(Hydroxycarbamoyl-1,2,3,4-tetrahydro-naphthalen-2-yl)-carbamic acid pyridin-3-ylmethyl ester;
7-(Butane-1-sulfonylamino)-5,6,7,8-tetrahydro-naphthalene-2-carboxylic acid hydroxyamide;
7-(3-Fluoro-benzenesulfonylamino)-5,6,7,8-tetrahydro-naphthalene-2-carboxylic acid hydroxyamide;
7-(4-Chloro-benzenesulfonylamino)-5,6,7,8-tetrahydro-naphthalene-2-carboxylic acid hydroxyamide;
7-(3-Chloro-benzenesulfonylamino)-5,6,7,8-tetrahydro-naphthalene-2-carboxylic acid hydroxyamide;
7-(3-Trifluoromethyl-benzenesulfonylamino)-5,6,7,8-tetrahydro-naphthalene-2-carboxylic acid hydroxyamide;
7-(2,4-Difluoro-benzenesulfonylamino)-5,6,7,8-tetrahydro-naphthalene-2-carboxylic acid hydroxyamide;
7-(3,4-Dimethoxy-benzenesulfonylamino)-5,6,7,8-tetrahydro-naphthalene-2-carboxylic acid hydroxyamide;
7-(2,4-Dichloro-benzenesulfonylamino)-5,6,7,8-tetrahydro-naphthalene-2-carboxylic acid hydroxyamide;
7-(3,4-Dichloro-benzenesulfonylamino)-5,6,7,8-tetrahydro-naphthalene-2-carboxylic acid hydroxyamide;
7-(Pyridine-3-sulfonylamino)-5,6,7,8-tetrahydro-naphthalene-2-carboxylic acid hydroxyamide;
3-Fluoro-7-(pyrimidin-2-ylamino)-5,6,7,8-tetrahydro-naphthalene-2-carboxylic acid hydroxyamide;
3-Fluoro-7-(4-phenyl-pyrimidin-2-ylamino)-5,6,7,8-tetrahydro-naphthalene-2-carboxylic acid hydroxyamide;
7-(4-Chloro-benzenesulfonylamino)-3-fluoro-5,6,7,8-tetrahydro-naphthalene-2-carboxylic acid hydroxyamide;
7-(3-Chloro-benzenesulfonylamino)-3-fluoro-5,6,7,8-tetrahydro-naphthalene-2-carboxylic acid hydroxyamide;
3-(Pyridin-3-yl-pyrimidine-2-ylamino)-1,2,3,4-tetrahydro-quinoline-6-carboxylic acid hydroxyamide;
3-(3-Methoxy-benzoylamino)-1,2,3,4-tetrahydro-quinoline-6-carboxylic acid hydroxyamide;
3-(4-Chloro-benzoylamino)-1,2,3,4-tetrahydro-quinoline-6-carboxylic acid hydroxyamide;
3-(3-Chloro-benzoylamino)-1,2,3,4-tetrahydro-quinoline-6-carboxylic acid hydroxyamide;

3-(3-Trifluoromethyl-benzoylamino)-1,2,3,4-tetrahydro-quinoline-6-carboxylic acid hydroxyamide;
3-(3,4-Dichloro-benzoylamino)-1,2,3,4-tetrahydro-quinoline-6-carboxylic acid hydroxyamide;
3-[(Biphenyl-4-carbonyl)-amino]-1,2,3,4-tetrahydro-quinoline-6-carboxylic acid hydroxyamide; and
3-(4-Chloro-benzenesulfonylamino)-1,2,3,4-tetrahydro-quinoline-6-carboxylic acid hydroxyamide.

The following compounds show activity as HDAC8 inhibitors and are particularly preferred according to the present invention 7-(4-fluoro-phenylamino)-5,6,7,8-tetrahydro-naphthalene-2-carboxylic acid hydroxyamide;
7-(4-bromo-phenylamino)-5,6,7,8-tetrahydro-naphthalene-2-carboxylic acid hydroxyamide;
7-(4-nitro-phenylamino)-5,6,7,8-tetrahydro-naphthalene-2-carboxylic acid hydroxyamide;
7-(3-chloro-4-cyano-phenylamino)-5,6,7,8-tetrahydro-naphthalene-2-carboxylic acid hydroxyamide;
7-(pyridin-2-ylamino)-5,6,7,8-tetrahydro-naphthalene-2-carboxylic acid hydroxyamide;
7-(5-nitro-pyridin-2-ylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide;
7-(4-Phenyl-pyrimidin-2-ylamino)-5,6,7,8-tetrahydro-naphthalene-2-carboxylic acid hydroxyamide;
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(4-chloro-phenyl)-pyrimidin-2-ylamino]-5,6,7,8-tetrahydro-naphthalene-2-carboxylic acid hydroxyamide;
7-[4-(3-chloro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide;
7-[4-(2-fluoro-4-methyl-phenyl)-pyrimidin-2-ylamino]-5,6,7,8-tetrahydro-naphthalene-2-carboxylic acid hydroxyamide;
7-[4-(2,4-Dimethoxy-phenyl)-pyrimidin-2-ylamino]-5,6,7,8-tetrahydro-naphthalene-2-carboxylic acid hydroxyamide;
7-[4-(4-Trifluoromethyl-phenyl)-pyrimidin-2-ylamino]-5,6,7,8-tetrahydro-naphthalene-2-carboxylic acid hydroxyamide;
7-[4-(2,4-Dichloro-phenyl)-pyrimidin-2-ylamino]-5,6,7,8-tetrahydro-naphthalene-2-carboxylic acid hydroxyamide;
7-[4-(4-chloro-2-methyl-phenyl)-pyrimidin-2-ylamino]-5,6,7,8-tetrahydro-naphthalene-2-carboxylic acid hydroxyamide;
7-[4-(3-Chloro-4-fluoro-phenyl)-pyrimidin-2-ylamino]-5,6,7,8-tetrahydro-naphthalene-2-carboxylic acid hydroxyamide;
7-[4-(4-Phenoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Methoxy-pyridin-3-yl)-pyrimidin-2-ylamino]-5,6,7,8-tetrahydro-naphthalene-2-carboxylic acid hydroxyamide;
7-[4-(6-Chloro-pyridin-3-yl)-pyrimidin-2-ylamino]-5,6,7,8-tetrahydro-naphthalene-2-carboxylic acid hydroxyamide;
7-[4-(2-Chloro-pyridin-3-yl)-pyrimidin-2-ylamino]-5,6,7,8-tetrahydro-naphthalene-2-carboxylic acid hydroxyamide;
7-[4-(6-Morpholin-pyridin-3-yl)-pyrimidin-2-ylamino]-5,6,7,8-tetrahydro-naphthalene-2-carboxylic acid hydroxyamide;
7-(4-Methyl-6-phenoxy-pyrimidin-2-ylamino)-5,6,7,8-tetrahydro-naphthalene-2-carboxylic acid hydroxyamide;
7-(4-Naphthalen-2-yl-pyrimidin-2-ylamino)-5,6,7,8-tetrahydro-naphthalene-2-carboxylic acid hydroxyamide;
7-(4-Quinolin-3-yl-pyrimidin-2-ylamino)-5,6,7,8-tetrahydro-naphthalene-2-carboxylic acid hydroxyamide;
7-(6-Fluoro-quinazolin-2-ylamino)-5,6,7,8-tetrahydro-naphthalene-2-carboxylic acid hydroxyamide;
7-[Methyl-(4-pyridin-3-ylpyrimidin-2-yl)-amino]-5,6,7,8-tetrahydro-naphthalene-2-carboxylic acid hydroxyamide;
7-(3-Pyridin-3-yl-acryloylamino)-5,6,7,8-tetrahydro-naphthalene-2-carboxylic acid hydroxyamide;
7-(Hydroxycarbamoyl-1,2,3,4-tetrahydro-naphthalen-2-yl)-carbamic acid pyridin-3-ylmethyl ester;
7-(Butane-1-sulfonylamino)-5,6,7,8-tetrahydro-naphthalene-2-carboxylic acid hydroxyamide;
7-(3-Fluoro-benzenesulfonylamino)-5,6,7,8-tetrahydro-naphthalene-2-carboxylic acid hydroxyamide;
7-(4-Chloro-benzenesulfonylamino)-5,6,7,8-tetrahydro-naphthalene-2-carboxylic acid hydroxyamide;
7-(3-Chloro-benzenesulfonylamino)-5,6,7,8-tetrahydro-naphthalene-2-carboxylic acid hydroxyamide;
7-(3-Trifluoromethyl-benzenesulfonylamino)-5,6,7,8-tetrahydro-naphthalene-2-carboxylic acid hydroxyamide;
7-(2,4-Difluoro-benzenesulfonylamino)-5,6,7,8-tetrahydro-naphthalene-2-carboxylic acid hydroxyamide;
7-(3,4-Dimethoxy-benzenesulfonylamino)-5,6,7,8-tetrahydro-naphthalene-2-carboxylic acid hydroxyamide;
7-(2,4-Dichloro-benzenesulfonylamino)-5,6,7,8-tetrahydro-naphthalene-2-carboxylic acid hydroxyamide;
7-(3,4-Dichloro-benzenesulfonylamino)-5,6,7,8-tetrahydro-naphthalene-2-carboxylic acid hydroxyamide;
7-(Pyridine-3-sulfonylamino)-5,6,7,8-tetrahydro-naphthalene-2-carboxylic acid hydroxyamide;
3-Fluoro-7-(4-phenyl-pyrimidin-2-ylamino)-5,6,7,8-tetrahydro-naphthalene-2-carboxylic acid hydroxyamide;
7-(4-Chloro-benzenesulfonylamino)-3-fluoro-5,6,7,8-tetrahydro-naphthalene-2-carboxylic acid hydroxyamide;
7-(3-Chloro-benzenesulfonylamino)-3-fluoro-5,6,7,8-tetrahydro-naphthalene-2-carboxylic acid hydroxyamide;
3-(Pyridin-3-yl-pyrimidine-2-ylamino)-1,2,3,4-tetrahydro-quinoline-6-carboxylic acid hydroxyamide;
3-(3-Methoxy-benzoylamino)-1,2,3,4-tetrahydro-quinoline-6-carboxylic acid hydroxyamide;
3-(4-Chloro-benzoylamino)-1,2,3,4-tetrahydro-quinoline-6-carboxylic acid hydroxyamide;
3-(3-Chloro-benzoylamino)-1,2,3,4-tetrahydro-quinoline-6-carboxylic acid hydroxyamide;
3-(3-Trifluoromethyl-benzoylamino)-1,2,3,4-tetrahydro-quinoline-6-carboxylic acid hydroxyamide;
3-(3,4-Dichloro-benzoylamino)-1,2,3,4-tetrahydro-quinoline-6-carboxylic acid hydroxyamide;

3-[(Biphenyl-4-carbonyl)-amino]-1,2,3,4-tetrahydro-quinoline-6-carboxylic acid hydroxyamide;
3-(3-Fluoro-benzenesulfonylamino)-1,2,3,4-tetrahydro-quinoline-6-carboxylic acid hydroxyamide;
3-(3-Chloro-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide;
3-(3-Trifluoromethyl-benzenesulfonylamino)-1,2,3,4-tetrahydro-quinoline-6-carboxylic acid hydroxyamide;
3-(3,4-Dimethoxy-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide; and
3-(4-Pyridin-3-yl-pyrimidin-2-ylamino)-chroman-6-6-carboxylic acid hydroxyamide.

The compounds of the present invention can be prepared by any conventional means. Suitable processes for synthesizing these compounds as well as their starting materials are provided in the schemes below and in the examples. All substituents, in particular, $R^1$ to $R^6$, and X are as defined above unless otherwise indicated. Furthermore, and unless explicitly otherwise stated, all reactions, reaction conditions, abbreviations and symbols have the meanings well known to a person of ordinary skill in organic chemistry.

ABBREVIATION

Boc: tert-butoxycarbonyl
d: day
Dabco: 1,4-diazabicyclo[2.2.2]octane
DIPEA: diisopropylethylamine
DMF: dimethylformamide
DMSO: dimethylsulfoxide
ECL: enhanced chemiluminescence
EDCI: 1-ethyl-3-(3-dimethylaminopropyl)carbodiimide
ELISA: enzyme-linked immunosorbent assay
EtOAc: ethyl acetate
FBS: fetal bovine serum
g: gram
$EC_{50}$: concentration required for 50% induction of acetylated tubulin
$IC_{50}$: concentration required for 50% enzymatic inhibition of HDAC8
h: hour
HATU: O-(7-azabenzotriazol-1-yl)-N,N,N',N'-tetramethyluronium hexafluorophosphate
HDAC: histone deacetylase
HOBt: 1-hydroxybenzotriazole
HPLC: high performance liquid chromatography
HRP: horseradish peroxidase
Hz: Hertz
KOH: potassium hydroxide
MeOD: deuterated methanol
MeOH: methanol
mg: milligram
MHz: megahertz
mL: milliliter
MM: multiple myeloma
mmol: millimole
NAD: nicotinamide adenine dinucleotide
NaOH: sodium hydroxide
NB: neuroblastoma
NMR: nuclear magnetic resonance
PyBrop: bromo-tris-pyrrolidino-phosphoniumhexafluorophosphate
psi: pounds per square inch
rt: room temperature
SAHA: suberoylanilide hydroxamic acid
TBS: tris-buffered saline
TEA: triethylamine
t-BuOK: potassium tert-butoxide
THF: tetrahydrofuran
µl: microliter
µM: micromole
WST: 4-[3-(4-iodophenyl)-2-(4-nitrophenyl)-2H-5-tetrazolio]-1,3-benzene disulfonate General Synthetic Scheme for 7-Phenylamino Based Analogues Ia (Scheme 1).

One category of the compounds described herein relates to 7-phenylamino-5,6,7,8-tetrahydro-naphthalene-2-carboxylic acid hydroxyamide based analogues with the formula Ia wherein $R^5$ is hydrogen, halogen, nitro, alkyl, trifluoromethyl, alkoxy, dialkylamino, aminoalkyl, cyano or phenoxy:

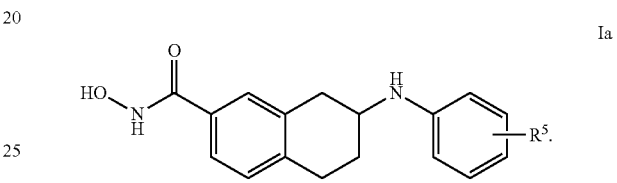

Ia

Compounds of interest Ia can be prepared according to the general synthesis method shown in Scheme 1.

Scheme 1

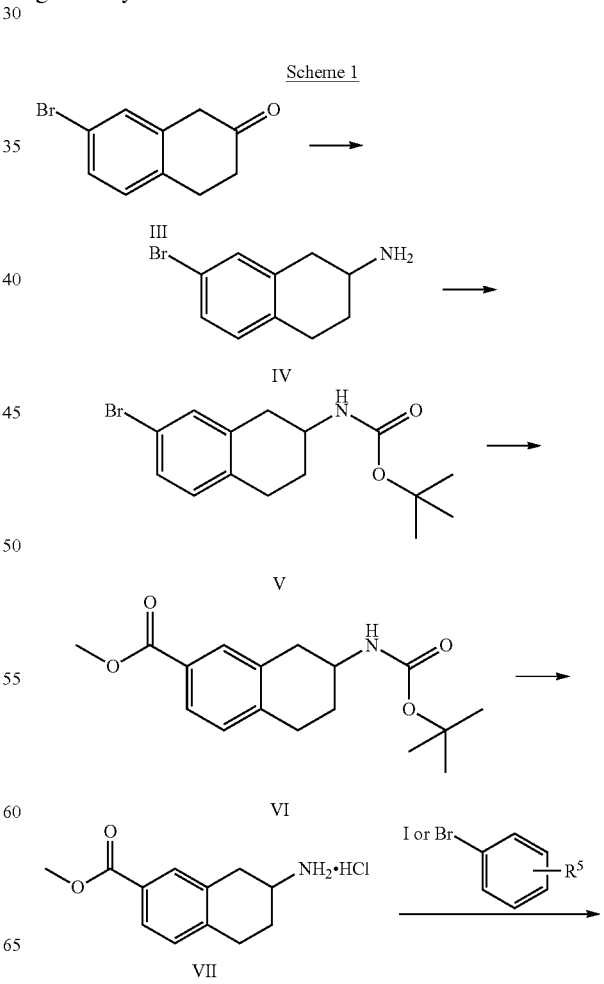

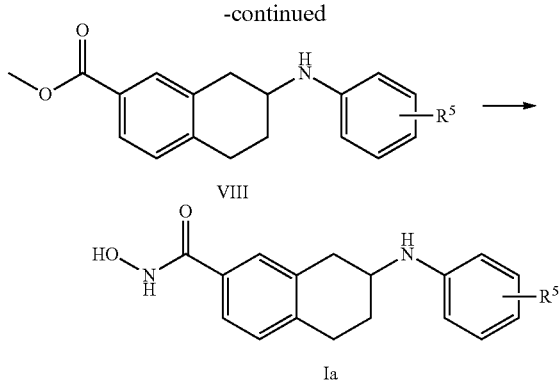

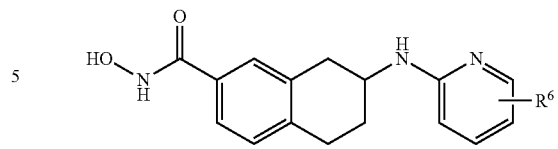

Compounds of interest Ib can be prepared according to Scheme 2. Starting with intermediate VII, it is coupled with various substituted pyridine analogues to give compound IX. Methyl ester IX is treated with aqueous hydroxylamine in the presence of NaOH to give compound of interest Ib.

Scheme 2

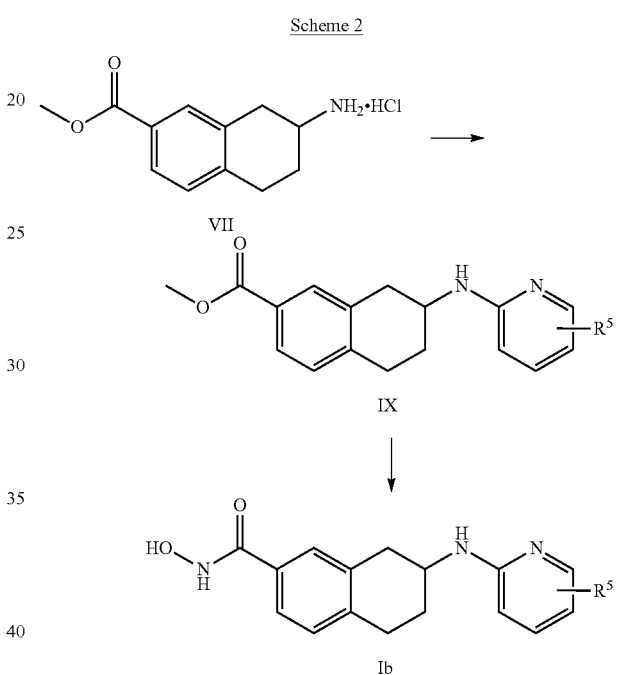

Starting from commercial available 7-bromo-3,4-dihydro-1H-naphthalen-2-one III, reductive amination of III with ammonium acetate and sodium cyanoborohydride affords substituted amine IV. When the free amine group of IV is protected with Boc anhydride to give compound V, a palladium catalyzed carbonyl insertion affords Boc-protected methyl ester VI. The Boc protective group in ester VI is removed under acidic conditions to give compound VII, which is in turn coupled with various substituted iodobenzene or bromobenzene analogues to give compound VIII. The methyl ester VIII is reacted with hydroxylamine in NaOH solution to give compounds of interest Ia.

7-Bromo-1,2,3,4-tetrahydro-naphthalen-2-ylamine IV can be prepared from reductive amination of compound III with ammonium acetate. The reaction can be carried out with a suitable reducing agent such as sodium triacetoxyborohydride in MeOH, typically at room temperature (rt) for twelve to sixteen hours.

Boc-protected compound V can be obtained by reaction of 7-bromo-1,2,3,4-tetrahydro-naphthalen-2-ylamine IV with di-tert-butyldicarbonate. The reaction can be carried out with a suitable organic base such as triethylamine (TEA) in an inert organic solvent such as dichloromethane, typically at rt for about five hours.

Compound VI can be prepared by carbonyl insertion of compound V with carbon monoxide and palladium catalyst in MeOH. The reaction is typically performed in deoxygenated MeOH with carbon monoxide, TEA, and tetrakis(triphenylphosphine)platinum (0) at 80-100° C. for about thirteen to eighteen hours.

Compound VII can be obtained by deprotection of VI. The reaction is typically performed in methanolic hydrogen chloride at rt over several hours.

Compound VIII can be prepared by copper-catalyzed coupling of amine VII with various substituted iodobenzene or bromobenzene analogues. The reaction is typically performed in deoxygenated DMF with TEA, cuprous iodide, L-proline at 120-140° C. for about four to ten hours under inert atmosphere.

Compounds of interest Ia can be obtained by treatment of methyl ester VIII with 50% hydroxylamine solution. The reaction is typically carried out in a mixture of methanol and aqueous KOH for about one hour.

General Synthetic Scheme for 7-(pyridin-2-ylamino) Based Analogues Ib (Scheme 2).

One category of the compounds described herein relates to 7-(pyridin-2-ylamino)-5,6,7,8-tetrahydro-naphthalene-2-carboxylic acid hydroxyamide based analogues with the formula Ib wherein $R^6$ is hydrogen, nitro, alkoxy or trifluoromethyl:

Compound IX can be prepared by copper-catalyzed coupling of amine VII with various substituted pyridine analogues. The reaction is typically performed in deoxygenated DMF with TEA, cuprous iodide, L-proline at 120-140° C. for about four to ten hours under inert atmosphere. Alternatively, IX can be prepared by nucleophilic displacement of substituted 2-fluoropyridine or 2-chloropyridine analogs with amine VII under basic conditions.

Compounds of interest Ib are obtained by treatment of methyl ester IX with 50% hydroxylamine solution. The reaction is typically carried out in a mixture of MeOH and aqueous KOH at rt for about one hour.

General Synthetic Scheme for 7-(pyrimidin-2-ylamino) Based Analogues Ic (Scheme 3).

One category of the compounds described herein relates to 7-(pyrimidin-2-ylamino)-5,6,7,8-tetrahydro-naphthalene-2-carboxylic acid hydroxyamide based analogues having the formula Ib wherein $R^7$ is hydrogen, alkyl, trifluoromethyl, alkoxy, phenoxy, pyridinyl, alkylpyridinyl, alkoxypyridinyl, halopyridinyl morpholinylpyridinyl, naphthyl, quinolinyl, phenyl or substituted phenyl, wherein substituted phenyl is phenyl once or twice substituted by alkyl, halogen, dialkylamino, nitro, alkoxy, trifluoromethyl or phenoxy:

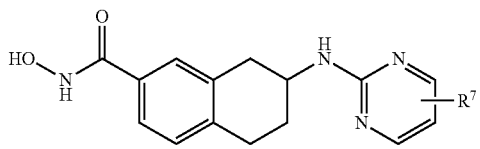

Compounds of interest Ic can be prepared according to Scheme 3. Starting with amine intermediate VII, it is are coupled with various substituted 2-chloro-pyrimidine analogues to give compounds X. The methyl esters X are treated with aqueous hydroxylamine in the presence of NaOH to give compounds of interest Ic.

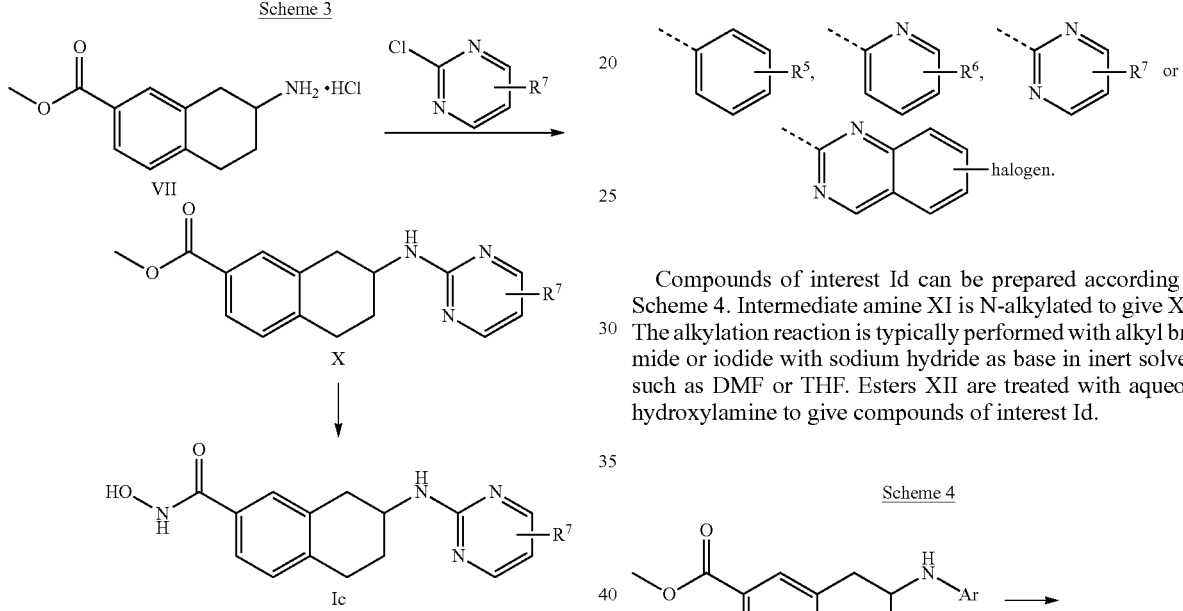

Compounds X can be prepared by nucleophilic displacement of various substituted 2-chloro pyrimidine analogues with amine VII under basic conditions. The reaction is typically performed at 120-150° C. for about 30 minutes to one hour in a microwave reactor with deoxygenated DMF as solvent.

Compounds of interest Ic are obtained by treatment of methyl ester X with 50% hydroxylamine solution. The reaction is typically carried out in a mixture of MeOH and aqueous KOH for about one hour.

Additional, the 7-(quinazolin-2-ylamino) analogs with 5, 6, 7 or 8-halogen substituted quinazolinyl groups can be prepared in a similar manner by using substituted 2-chloro-quinazolines as starting material in the nucleophilic displacement reaction.

General Synthetic Scheme for 7-N-alkyl Substituted Analogues Id (Scheme 4).

One category of the compounds described herein relates to 7-(N-alkyl, N-aryl)-amino analogues having the formula Id wherein $R^2$ is alkyl. Ar is phenyl, unsubstituted or substituted by halogen, nitro, alkyl, trifluoromethyl, alkoxy, dialkylamino, aminoalkyl, cyano or phenoxy; pyridin-2-yl, unsubstituted or substituted by nitro, alkoxy or trifluoromethyl; pyrimidin-2-yl, unsubstituted or substituted by alkyl, trifluoromethyl, alkoxy, phenoxy, pyridinyl, alkylpyridinyl, alkoxy-pyridinyl, halopyridinyl morpholinylpyridinyl, naphthyl, quinolinyl, phenyl or substituted phenyl, wherein substituted phenyl is phenyl once or twice substituted by alkyl, halogen, dialkylamino, nitro, alkoxy, trifluoromethyl or phenoxy; quinazolin-2-yl, unsubstituted or substituted by halogen:

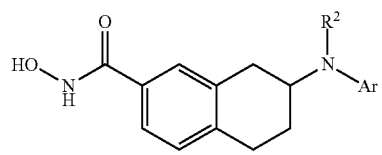

Ar is

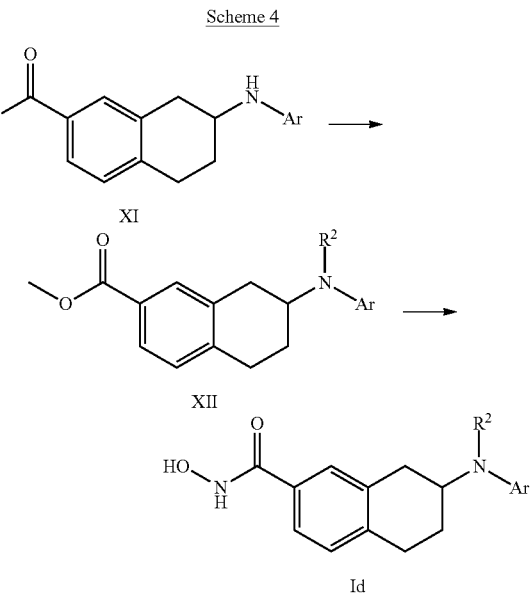

Compounds of interest Id can be prepared according to Scheme 4. Intermediate amine XI is N-alkylated to give XII. The alkylation reaction is typically performed with alkyl bromide or iodide with sodium hydride as base in inert solvent such as DMF or THF. Esters XII are treated with aqueous hydroxylamine to give compounds of interest Id.

Ar is

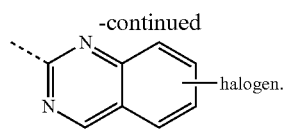

General Synthetic Scheme for 7-amide Substituted Analogues Ie (Scheme 5).

One category of the compounds described herein relates to 7-carbonylamino-5,6,7,8-tetrahydro-naphthalene-2-carboxylic acid hydroxyamide based analogues with the formula Ie wherein $R^8$ is phenylalkenyl, phenylalkyl, phenylalkoxy, pyridinylalkenyl, pyridinylalkyl, pyridinylalkoxy, phenyl or substituted phenyl wherein substituted phenyl is phenyl once or twice substituted by halogen, alkyl, trifluoromethyl, alkoxy, trifluoromethoxy, cyano, dialkylamino or phenyl:

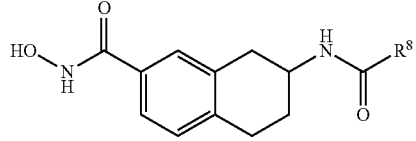

Compounds of interest Ie can be prepared according to Scheme 5. Intermediate amine VII is coupled with various substituted carboxylic acids or acyl chlorides to give compounds XIII. The methyl esters XIII are treated with aqueous hydroxylamine in the presence of NaOH to give compounds of interest Ie.

Scheme 5

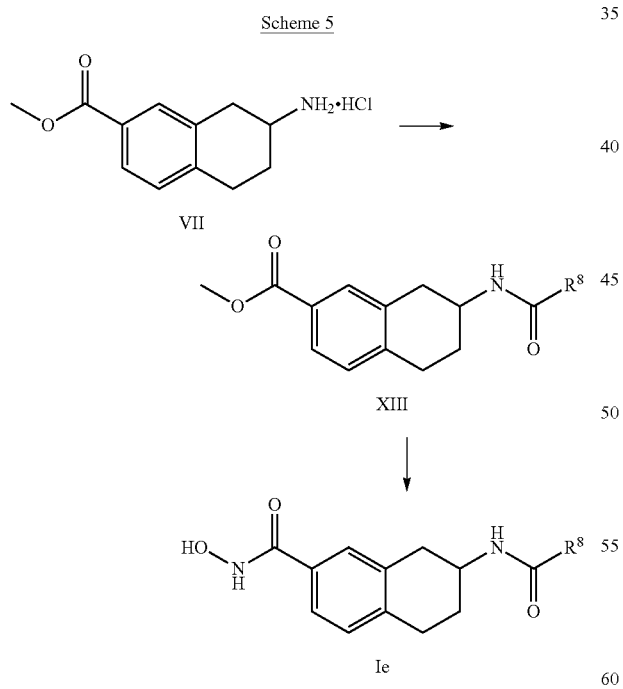

Amides XIII can be prepared from coupling of compound VII with various carboxylic acids. The reaction is typically performed with standard peptide coupling reagents such as EDCI and HOBt, PyBrop and DIPEA, or HATU and TEA in a suitable inert solvent such as dichloromethane or DMF or mixtures thereof at rt for several hours.

Compounds of interest Ie are obtained by treatment of methyl ester XIII with 50% hydroxylamine solution. The reaction is typically carried out in a mixture of MeOH and aqueous KOH for about one hour.

General Synthetic Scheme for 7-sulfonylamino Substituted Analogues If (Scheme 6).

One category of the compounds described herein relates to 7-sulfonylamino-5,6,7,8-tetrahydro-naphthalene-2-carboxylic acid hydroxyamide based analogues having the formula Ie wherein $R^9$ is alkyl, pyridinyl, phenyl or substituted phenyl wherein substituted phenyl is phenyl once or twice substituted by halogen, trifluoromethyl, trifluoromethoxy, alkoxy, cyano, dialkylamino or dialkylaminoalkyl:

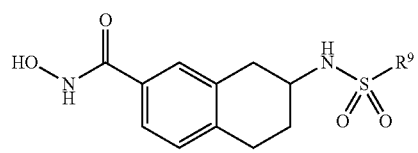

Compounds of interest If can be prepared according to Scheme 6. Intermediate VII is treated with various substituted sulfonyl chlorides to give sulfonamides XIV. Methyl esters XIV are treated with aqueous hydroxylamine in the presence of NaOH to give compounds of interest If.

Scheme 6

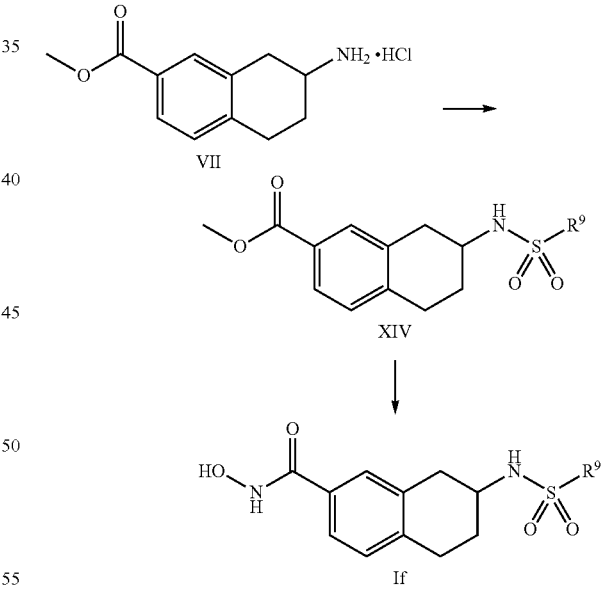

Sulfonamide XIV can be prepared from coupling of compound VII with various sulfonyl chlorides. The reaction is typically performed under standard sulfonylation conditions with DIPEA or TEA in a suitable inert solvent such as THF, dichloromethane, DMF, or mixtures thereof at rt for several hours.

Compounds of interest If are obtained by treatment of methyl esters XIV with 50% hydroxylamine solution. The reaction is typically performed in MeOH with a suitable base such as KOH.

General Synthetic Scheme for 3-fluoro Substituted Analogues Ig (Scheme 7).

One category of the compounds described herein relates to 3-fluoro substituted analogues with the formula Ig.

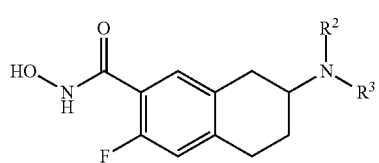

Ig

Scheme 7 shows the general synthesis method for compounds of interest Ig. In analogy to the synthesis of Ia, Ib, Ic, Id, Ie, and If, the 3-fluoro substituted analogs Ig are made from intermediate XIX for functional group transformations. $R^2$ and $R^3$ have the same definition as described in formula Ia, Ib, Ic, Id, Ie, and If.

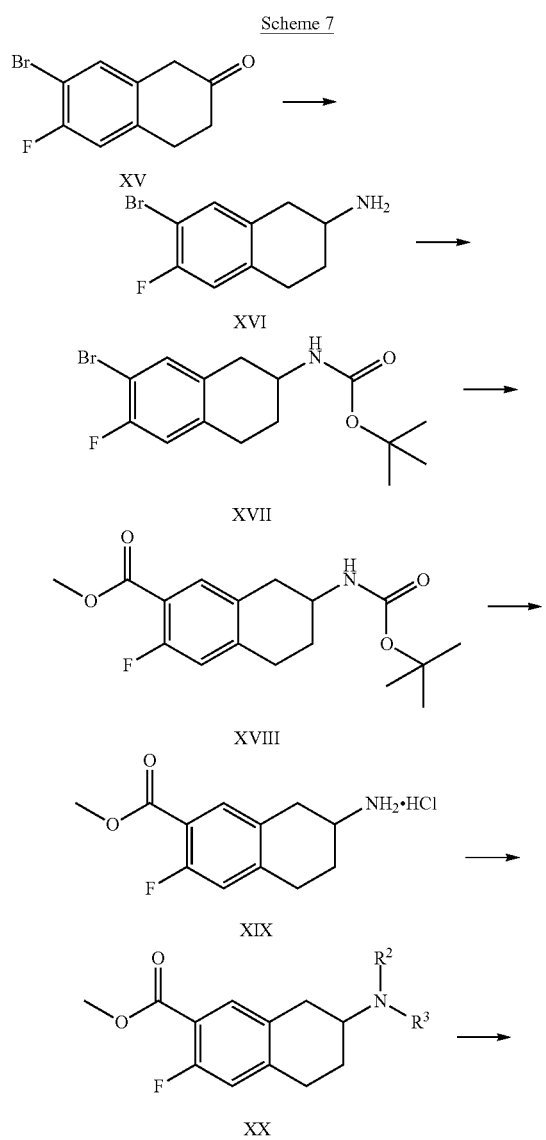

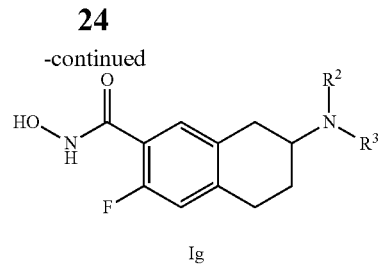

Ig

Starting from 7-bromo-6-fluoro-3,4-dihydro-1H-naphthalen-2-one XV, amine XIX can be prepared by reductive amination, Boc protection of free amine group, carbonyl insertion and deprotection of Boc. The amino group of XIX can be transformed in a similar manner as shown in Scheme 1 to 6 to give methyl esters XX. Thus, compounds XX are prepared by either copper catalyzed coupling, nucleophilic displacement reaction, alkylation, acylation, or sulfonation of amine XIX in analogy to the synthesis of intermediates VIII, IX, X, XII, XIII, and XIV. XX can be treated with aqueous hydroxylamine in the presence of NaOH to give compounds of interest Ig.

General Synthetic Scheme for 1,2,3,4-tetrahydro-quinoline Based Analogues Ih and Ii (Scheme 8).

One category of the compounds described herein relates to 3-amino-1,2,3,4-tetrahydro-quinoline-6-carboxylic acid hydroxyamides with the formula If and Ii wherein $R^2$ is hydrogen, $R^3$ has the same definition as described previously in formula Ia, Ib, Ic, Id, Ie and If, and $R^4$ is alkyl.

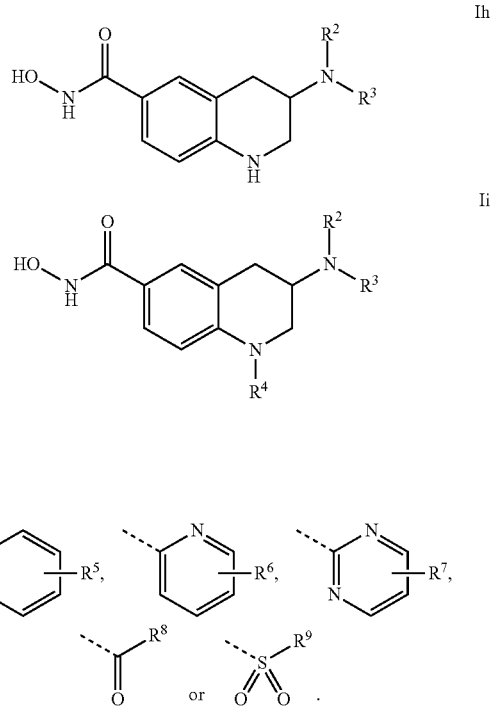

Compounds of interest Ih can be prepared according to Scheme 8. Starting with commercial available quinolin-3-ylamine XXI, the free amine group is protected by Boc anhydride to give compound XXII, which is reduced to XXIII through catalytic hydrogenation. Bromination of XXIII with pyridinium tribromide gives 6-bromo analog XXIV regioselectively. The bromide XXIV is converted to the corresponding 6-cyano derivative XXV by zinc cyanide. Hydrolysis of XXV by methanolic hydrogen chloride leads to ester XXVI with concomitant removal of Boc protective group. In analogy to the synthesis of Ia, Ib, Ic, Ie, and If, the target compounds of interest Ih are made from intermediate XXVI through functional group transformations and subsequent treatment of esters XXVII with aqueous hydroxylamine. Additionally, 1,2,3,4-tetrahydro-quinolines XXVII can be transformed to N-alkylated products XXVIII by treatment with aldehyde and reducing agents. Compounds of interest Ii are obtained by treating XXVIII with aqueous hydroxylamine under basic conditions.

reaction is carried out in two steps by hydrolysis of cyano group and esterification. The cyano group can be hydrolyzed with a suitable inorganic acid such as concentrated hydrochloride at refluxing temperature in a sealed tube for four to six hours. When the hydrolysis is complete, MeOH is added to the reaction mixture, and the esterification can be finished in three to five hours.

Compound XXVII can be prepared by either copper catalyzed coupling, nucleophilic displacement reaction, acylation or sulfonation of amine XXVI in analogy to the synthesis of intermediates VIII, IX, X, XIII, and XIV.

Scheme 8

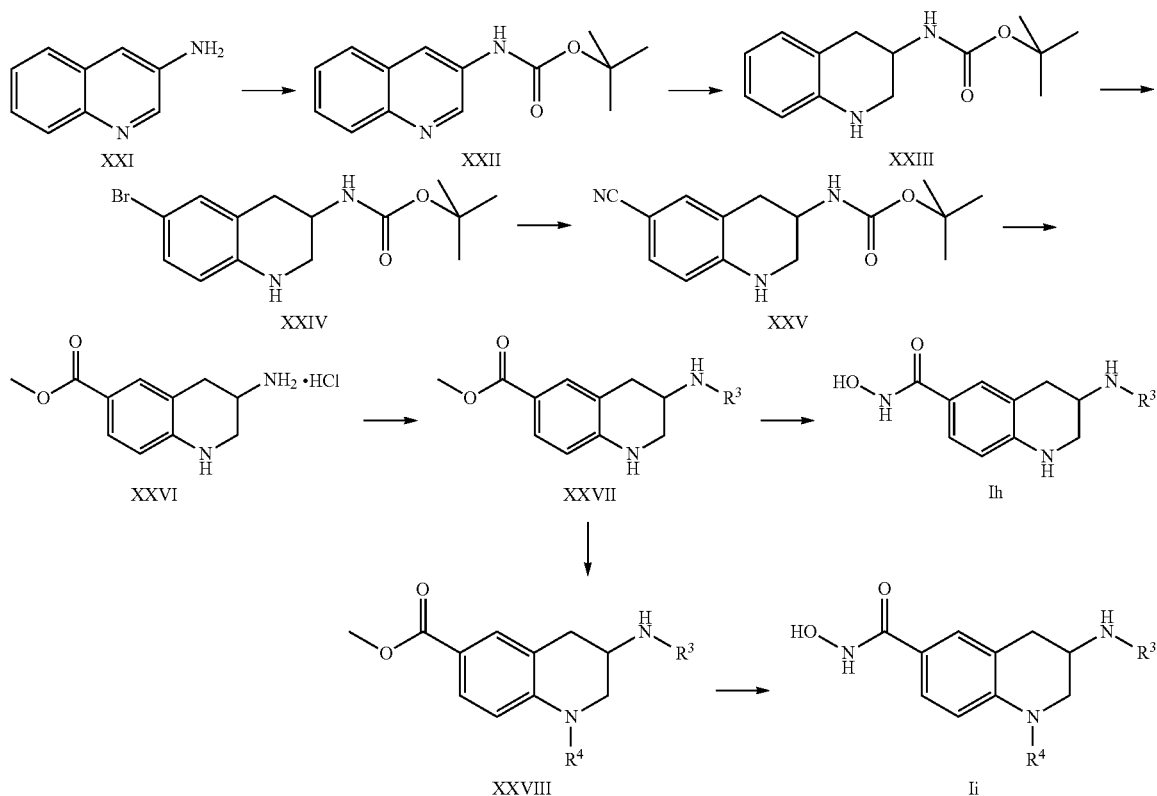

The carbamate XXII can be obtained by the reaction of quinolin-3-ylamine XXI with di-tert-butyldicarbonate. The reaction is carried out with a suitable organic base such as sodium bis(trimethylsilyl)amide in an organic solvent such as anhydrous THF, typically at rt for about five hours.

Boc-protected 3-amine-1,2,3,4-tetrahydroquinoline XXIII can be prepared by catalytic hydrogenation of XXII The reaction can be carried out with a suitable catalyst such as palladium in MeOH, typically at rt for twelve to sixteen hours.

The bromide XXIV can be prepared by bromination with pyridinium tribromide. The reaction is typically performed in anhydrous THF at rt for about half an hour.

Compound XXV can be prepared by palladium-catalyzed cyanation reaction of XXIV. The reaction is typically performed in deoxygenated DMF with zinc cyanide, tetrakis(triphenylphosphine)platinum (0), at 120-150° C. for about thirteen to eighteen hours under inert atmosphere.

The amine XXVI can be prepared from one-pot acid hydrolysis and Boc deprotection of compound XXV. The Compounds XXVIII can be prepared by N-alkylation of compounds XXVII with aldehyde and reducing agents. The reaction can be carried out with a suitable reducing agent such as sodium cyanoborohydride in acetic acid or THF, typically at rt for five hours.

Compounds of interest Ih or Ii are obtained by treating methyl esters XXVII or XXVIII with 50% hydroxylamine solution. The reaction is typically carried out in MeOH with aqueous KOH for about one hour.

General Synthetic Scheme for 3-amino-chroman Based Analogues Ij (Scheme 9).

One category of the compounds described herein relates to 3-amino-chroman-6-carboxylic acid hydroxyamides having the formula Ij wherein $R^2$ is hydrogen or alkyl, and $R^3$ has the same definition as described previously in formula Ia, Ib, Ic, Id, Ie, and If.

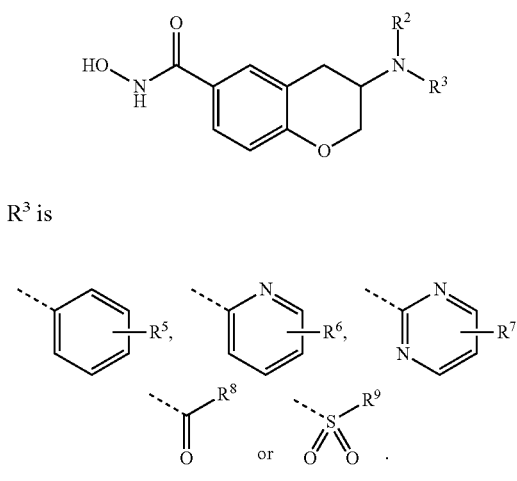

R³ is

Compounds of interest Ij can be prepared according to Scheme 9. Treatment of commercial available 5-bromo-2-hydroxy-benzaldehyde XXIX with acrylonitrile and 1,4-diazabicyclo[2.2.2]octane (Dabco) affords 6-bromo-2H-chromene-3-carbonitrile XXX. Hydrolysis of XXX leads to acid XXXI. Acid XXXI is then converted to ester XXXII via carbonyl insertion, followed by catalytic hydrogenation over palladium to give chroman XXXIII. The amine intermediate XXXIV is made by Curtius rearrangement of acid XXXIII. In analogy to the synthesis of Ia, Ib, Ic, Id, Ie, and If, the target compounds of interest Ij are made by functional group transformations of amine XXXIV and subsequent treatment of esters XXXV with aqueous hydroxylamine.

Scheme 9

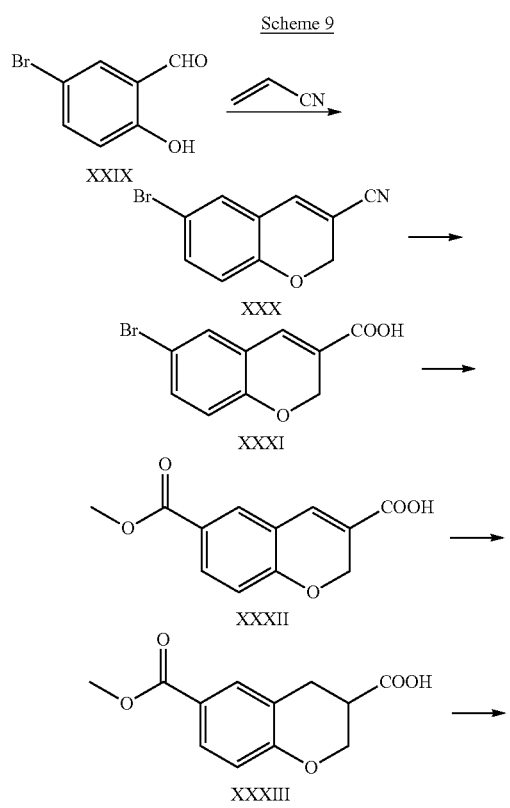

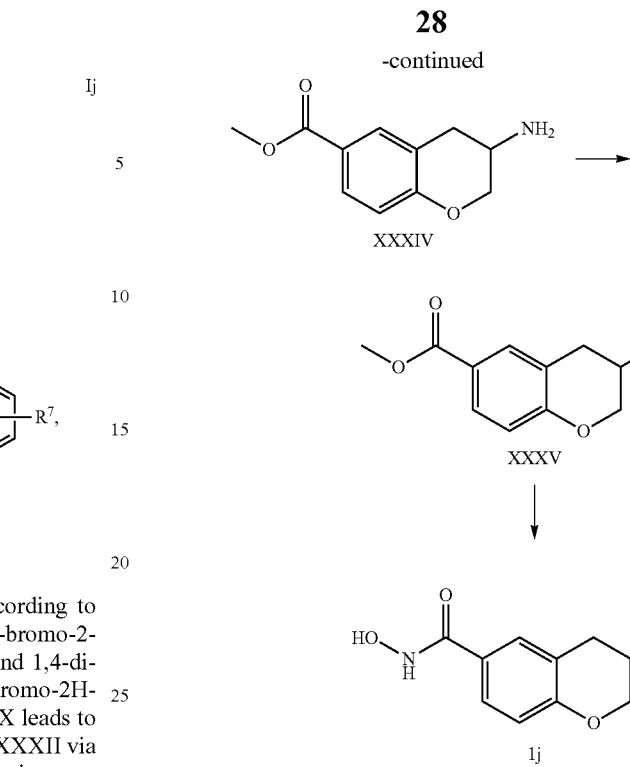

6-Bromo-2H-chromene-3-carbonitrile XXX can be obtained by condensation of XXIX with acrylonitrile. The reaction can be carried out using a suitable organic base such as Dabco in solvent-free system at reflux temperature for twenty hours.

Acid XXXI can be prepared from hydrolysis of XXX under basic conditions. The reaction can be carried out with NaOH, typically at refluxing temperature for six hours.

2H-Chromene-3,6-dicarboxylic acid 6-methyl ester XXXII can be prepared by carbonyl insertion of XXXI with carbon monoxide. The reaction is typically performed in deoxygenated MeOH with TEA, tetrakis(triphenylphosphine)platinum (0), at 80-100° C. for about thirteen to eighteen hours under inert atmosphere.

Compound XXXIII can be prepared by catalytic hydrogenation with XXXII. The reaction can be carried out with a suitable catalyst such as palladium hydroxide and in a suitable organic solvent such as MeOH, typically at 80° C. for about 48 hours under 40 psi hydrogen atmosphere.

Compound XXXIV can be prepared by Curtius rearrangement reaction of XXXIII. The reaction is typically performed in tert-butylalcohol with TEA, diphenyl phosphoryl azide at 80° C. for about twelve hours.

Compound XXXV can be prepared by either copper catalyzed coupling, nucleophilic displacement reaction, alkylation, acylation or sulfonation of amine XXXIV in analogy to the synthesis of intermediates VIII, IX, X, XII, XIII, and XIV.

Compounds of interest Ij are obtained by treatment of methyl ester XXXV with 50% hydroxylamine solution. The reaction is typically carried out with hydroxylamine and aqueous KOH in MeOH.

The invention also relates to a process for the preparation of a compound of formula (I) comprising one of the following steps:

(a) the reaction of a compound of formula (A1) or (A2)

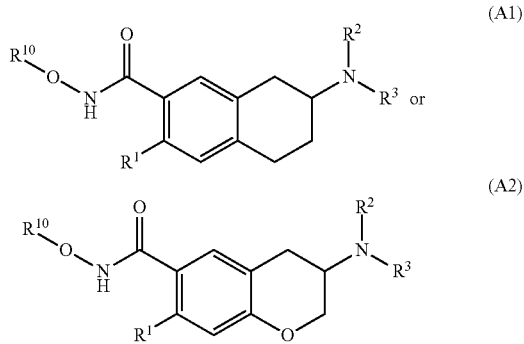

in the presence of a base and hydroxyamine;
(b) the reaction of a compound of formula (B)

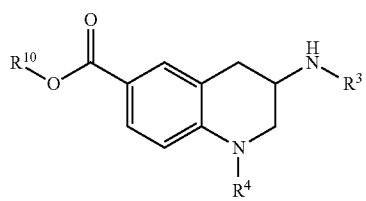

in the presence of a base and hydroxyamine;
wherein $R^1$, $R^2$, $R^3$, $R^4$ are given before and $R^{10}$ is alkyl.

In step (a) and (b), the reaction is carried out with hydroxylamine and aqueous KOH in MeOH for one to several hours.

The compounds of formula (I) show valuable properties due to their ability to selectively inhibit HDAC 6 or 8. Therefore the present compounds may be used in the treatment of diseases mediated by HDAC 6 or HDAC 8 dysfunction, in particular in the treatment of certain types of cancer, in particular neuroblastoma or multiple myeloma.

The invention thus also relates to a compound of formula (I) for use as medicament.

The invention also relates to a pharmaceutical composition comprising a compound of formula (I) and a therapeutically inert carrier.

In another embodiment according to the present invention, there is provided the use of a compound of formula (I) for the preparation of medicaments useful in the treatment of cancer, in particular, neuroblastoma and multiple myeloma. This embodiment also encompasses the use of a compound of formula (I) for the preparation of a medicament for the treatment of cancer, in particular, neuroblastoma and multiple myeloma.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, as such carriers (or excipients) for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-200 mg/kg, and can be taken singly or distributed over several administrations.

A compound of formula (I) when manufactured according to the above process is also an object of the invention.

Furthermore, the invention also relates to a method for the treatment of diseases that are related to HDAC 6 or HDAC 8 inhibition, which method comprises administering an effective amount of a compound of formula (I).

The invention further relates to a method for the treatment of cancer, in particular multiple myeloma, which method comprises administering an effective amount of a compound of formula (I).

Furthermore, the invention also relates to a compound of formula (I) for the preparation of medicaments useful in the treatment of diseases that are related to HDAC 6 or HDAC 8 inhibition. The invention provides a method for the treatment of diseases that are related to HDAC 6 or HDAC 8 inhibition, which method comprises administering an effective amount of a compound of formula (I).

EXAMPLES

Figure 1:
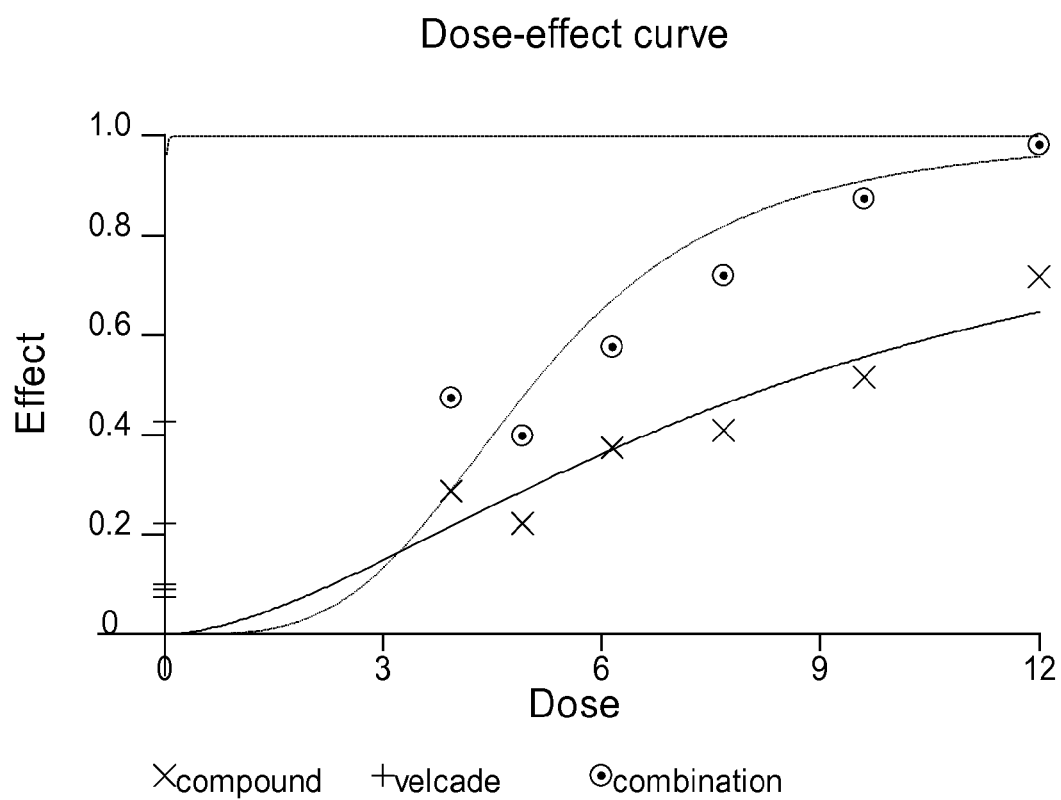
FIG. 1. EXAMPLE 24 synergized with Velcade to inhibit the cell growth of RPMI-8226 cells.

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 min):
Acidic condition: A: 0.1% formic acid in $H_2O$; B: 0.1% formic acid in acetonitrile;

Basic condition: A: 0.01% NH$_3$.H$_2$O in H$_2$O; B: acetonitrile;
Neutral condition: A: H$_2$O; B: acetonitrile.
Mass spectra (MS): generally only ions which indicate the parent mass are reported, and unless otherwise stated the mass ion quoted is the positive mass ion (M+H)$^+$.
The microwave assisted reactions were carried out in a Biotage Initiator Sixty.
NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

Example 1

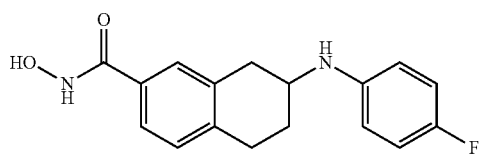 [SMILES: O=C(NO)c1ccc2c(c1)CC(Nc1ccc(F)cc1)CC2]

7-(4-fluoro-phenylamino)-5,6,7,8-tetrahydro-naphthalene-2-carboxylic acid hydroxyamide The title compound was prepared according to the synthesis method shown in Scheme 1. And a detailed synthesis route was provided as shown in Scheme 10.

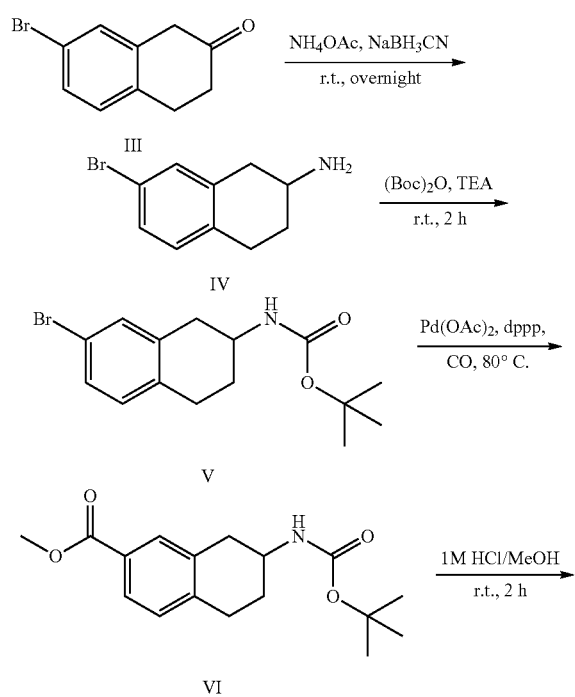

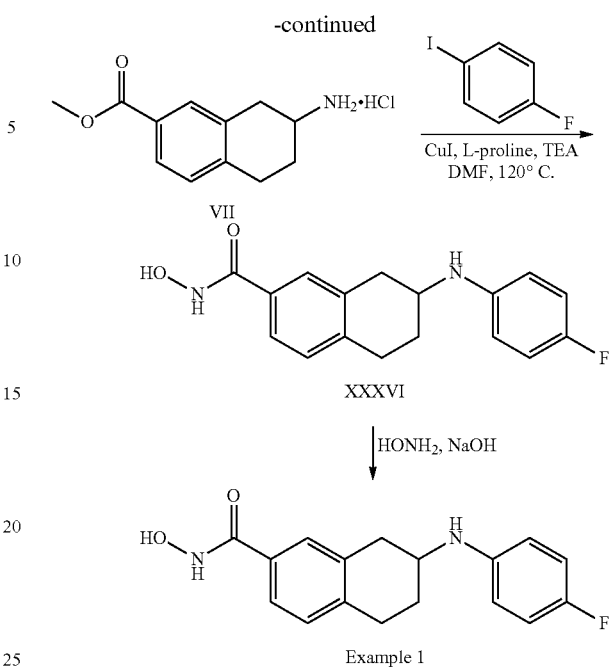

In details, 7-bromo-1,2,3,4-tetrahydro-naphthalen-2-ylamine (IV) was prepared from commercial available 7-bromo-2-tetralone. 1 g of 7-bromo-2-tetralone (4.5 mmol) was dissolved in 50 mL of MeOH. To the solution was added NaBH$_3$CN (0.44 g) and NH$_4$OAc (6 g) at rt. The mixture was stirred at rt overnight. The mixture was concentrated and partitioned between aqueous Na$_2$CO$_3$ (100 mL) and DCM (100 mL). The organic layer was dried and evaporated, and the crude product was used in next step reaction without further purification.

The crude product, 7-bromo-1,2,3,4-tetrahydro-naphthalen-2-ylamine (1 g) was dissolved in 50 mL of EtOH. To the solution was added 1.3 g of (Boc)$_2$O and 1 mL of TEA. The mixture was stirred at rt for 2 hours. The mixture was evaporated to oil and worked up with water (100 mL) and EtOAc (100 mL). The organic layer was washed with saline, dried and evaporated to give the crude product (IV), which was used in the next step without further purification. A mixture of (7-Bromo-1,2,3,4-tetrahydro-naphthalen-2-yl)-carbamic acid tert-butyl ester (IV, 0.3 g), TEA (0.5 mL), palladium acetate (60 mg), 1,3-bis(diphenylphosphino)propane (60 mg) and DMF (3 mL) in 10 mL of MeOH was purged for ten minutes with carbon monoxide. The reaction mixture was stirred under carbon monoxide atmosphere for 12 hours at 80° C. The reaction mixture was concentrated and partitioned between water and EtOAc. 280 mg of 7-tert-butoxycarbonylamino-5,6,7,8-tetrahydro-naphthalene-2-carboxylic acid methyl ester (VI) was obtained by flash chromatography on silica gel.

7-Amino-5,6,7,8-tetrahydro-naphthalene-2-carboxylic acid methyl ester (VII) was prepared by treating 7-tert-Butoxycarbonylamino-5,6,7,8-tetrahydro-naphthalene-2-carboxylic acid methyl ester (VI, 280 mg) with 1M HCl/MeOH (10 mL) at rt for 1 hour. The mixture was evaporated and the crude product (0.2 g) was used in the next step functional group transformations without further purification.

A mixture of HCl salt of amine VII (180 mg, 0.88 mmol), 1-fluoro-4-iodo-benzene (124 mg, 0.58 mmol), TEA (0.16 mL, 1.2 mmol), CuI (11 mg, 0.058 mmol), and L-proline (13 mg, 0.116 mmol) in 3 mL of DMF was heated in microwave reactor at 120° C. for 30 min. When the reaction was complete, the mixture was partitioned between water and EtOAc. The crude product (XXXVI) was mixed with 50% aqueous NH$_2$OH (1 mL) and KOH (50 mg) in 1 mL of MeOH. After stirred at rt for 1 hour, the reaction solution was sent to preparative RP-HPLC for purification without further workup. After HPLC separation, the eluent was concentrated under vacuum to remove the organic solution. The residue was dried by lyophylization to give the title compound, EXAMPLE 1. MS: calc'd (MH$^+$) 301, exp (MH$^+$) 301.1. $^1$HNMR (CD$_3$OD, 400 MHz), 7.52 (d, 2H, J=8.0 Hz), 7.24 (m, 1H), 7.12 (m, 4H), 3.85 (m, 1H), 3.22 (m, 1H), 3.05-2.84 (m, 3H), 2.26 (m, 1H), 1.78 (m, 1H).

Example 2

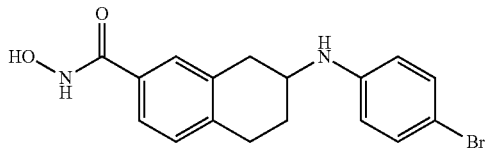 [SMILES: O=C(NO)c1ccc2c(c1)CC(Nc1ccc(Br)cc1)CC2]

7-(4-bromo-phenylamino)-5,6,7,8-tetrahydro-naphthalene-2-carboxylic acid hydroxyamide The title compound was prepared in analogy to EXAMPLE 1 as shown in Scheme 10, by using 1-bromo-4-iodo-benzene instead of 1-fluoro-4-iodo-benzene. MS: calc'd (MH$^+$) 361.2, exp (MH$^+$) 361.0. $^1$H NMR (CD$_3$OD, 400 MHz), 7.50 (d, 2H, J=6.4 Hz), 7.22 (d, 1H, J=8.8 Hz), 7.01 (t, 1H, J=8.0 Hz), 6.83 (t, 1H, J=2.0 Hz), 6.71 (m, 1H), 6.63 (m, 1H), 3.74 (m, 1H), 3.20 (m, 1H), 2.97 (m, 2H), 2.76 (m, 1H), 2.21 (m, 1H), 1.73 (m, 1H).

Example 3

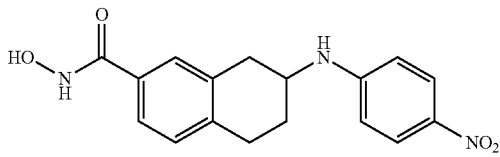 [SMILES: O=C(NO)c1ccc2c(c1)CC(Nc1ccc([N+](=O)[O-])cc1)CC2]

7-(4-nitro-phenylamino)-5,6,7,8-tetrahydro-naphthalene-2-carboxylic acid hydroxyamide The title compound was prepared in analogy to EXAMPLE 1 as shown in Scheme 10, by using 1-iodo-4-nitro-benzene instead of 1-fluoro-4-iodo-benzene. MS: calc'd (MH$^+$) 328.3, exp (MH$^+$) 328.1. $^1$H NMR (CD$_3$OD, 400 MHz), 8.05 (m, 2H), 7.52 (d, 2H, J=6.0 Hz), 7.23 (d, 1H, J=8.4 Hz), 6.72 (m, 2H), 3.93 (m, 1H), 3.24 (m, 1H), 3.02 (m, 2H), 2.84 (m, 1H), 2.24 (m, 1H), 1.82 (m, 1H).

Example 4

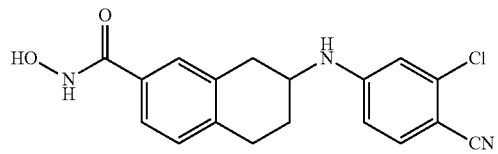 [SMILES: N#Cc1ccc(NC2CCc3ccc(C(=O)NO)cc3C2)cc1Cl]

7-(3-chloro-4-cyano-phenylamino)-5,6,7,8-tetrahydro-naphthalene-2-carboxylic acid hydroxyamide The title compound was prepared in analogy to EXAMPLE 1 as shown in Scheme 10, by using 2-chloro-4-iodo-benzonitrile instead of 1-fluoro-4-iodo-benzene. MS: calc'd (MH$^+$) 342.1, exp (MH+) 342. $^1$H NMR (CD$_3$OD, 400 MHz), 7.64 (m, 2H), 7.51 (m, 2H), 7.24 (d, 1H, J=8.8 Hz), 6.95 (d, 1H, J=8.8 Hz), 3.98 (m, 1H), 3.27 (m, 1H), 3.04 (m, 2H), 2.97 (m, 1H), 2.24 (m, 1H), 1.87 (m, 1H).

Example 5

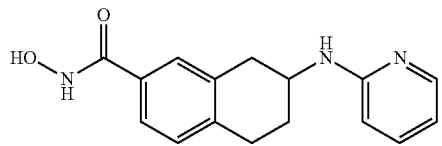 [SMILES: O=C(NO)c1ccc2c(c1)CC(Nc1ccccn1)CC2]

7-(Pyridin-2-ylamino)-5,6,7,8-tetrahydro-naphthalene-2-carboxylic acid hydroxyamide The title compound was prepared in analogy to EXAMPLE 1 as shown in Scheme 10, by using 2-bromopyridine instead of 1-fluoro-4-iodo-benzene. MS: calc'd (MH$^+$) 284.1, exp (MH$^+$) 284.3. $^1$H NMR (CD$_3$OD, 400 MHz), 7.85-7.93 (m, 2H), 7.55 (m, 2H), 7.25 (d, 1H, J=8 Hz), 7.12 (d, 1H, J=8.8 Hz), 6.92 (t, 1H, J=6.4 Hz), 4.79 (m, 1H), 2.8-3.2 (m, 4H), 2.2 (m, 1H), 1.9 (m, 1H).

Example 6

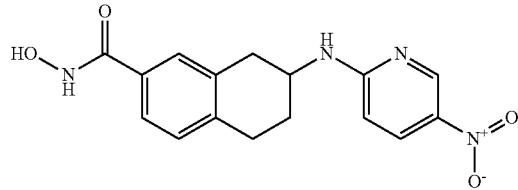 [SMILES: O=C(NO)c1ccc2c(c1)CC(Nc1ccc([N+](=O)[O-])cn1)CC2]

7-(5-Nitro-pyridin-2-ylamino)-5,6,7,8-tetrahydro-naphthalene-2-carboxylic acid hydroxyamide The title compound was prepared in analogy to EXAMPLE 1 as shown in Scheme 10, by using 2-bromo-5- nitro-pyridine instead of 1-fluoro-4-iodo-benzene. MS: calc'd (MH⁺) 329.1, exp (MH⁺) 329.3. $^1$H NMR (MeOD, 400 MHz), 8.95-8.96 (d, 1H, J=2.8 Hz), 8.13-8.16 (dd, 1H, $J_j$=9.2 Hz, $J_2$=2 Hz), 7.52-7.53 (d, 2H, J=5.6 Hz), 7.22-7.24 (d, 1H, J=8.4 Hz), 6.57-6.59 (d, 1H, J=9.2 Hz), 4.39-4.05 (m, 1H), 3.23-3.28 (m, 1H), 2.99-3.03 (m, 2H), 2.80-2.87 (m, 1H), 2.21-2.23 (m, 1H), 1.84-1.91 (m, 1H).

Example 7

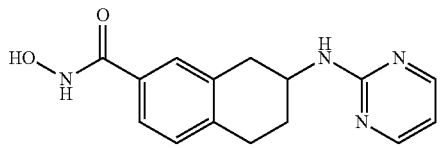 [SMILES: O=C(NO)c1ccc2c(c1)CC(Nc1ncccn1)CC2]

7-(Pyrimidin-2-ylamino)-5,6,7,8-tetrahydro-naphthalene-2-carboxylic acid hydroxyamide The title compound was prepared according to Scheme 3. And a detailed synthesis route was provided as shown in Scheme 11.

Scheme 11

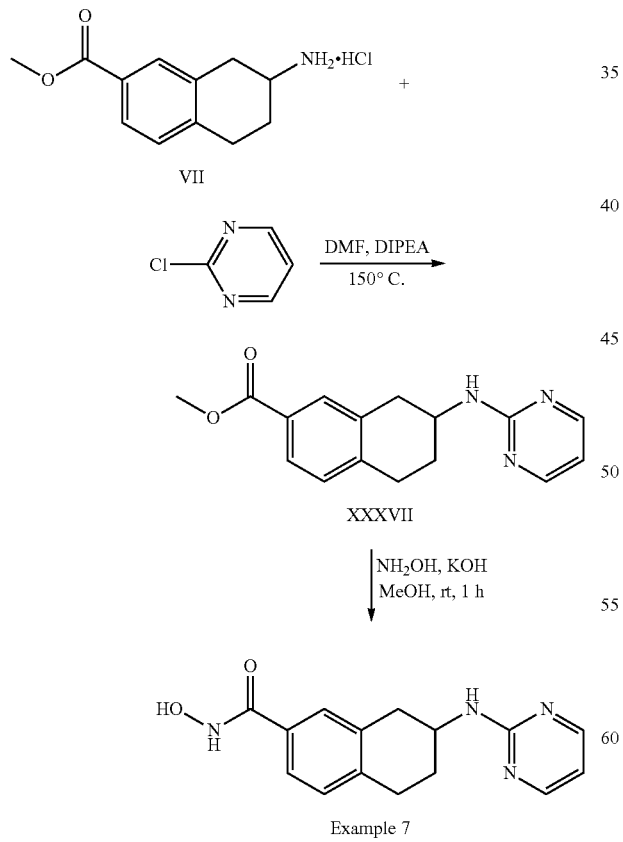

7-(Pyrimidin-2-ylamino)-5,6,7,8-tetrahydro-naphthalene-2-carboxylic acid methyl Ester (XXXVII) was obtained by heating the mixture of 7-amino-5,6,7,8-tetrahydro-naphthalene-2-carboxylic acid methyl ester (VII, 60 mg), 2-chloro-pyrimidine (50 mg) and TEA (0.2 mL) in 2 mL of DMF at 150° C. for 1 hour in microwave reactor. The mixture was diluted with EtOAc (50 mL) and washed with water (50 mL). After concentration, the crude product (XXXVII, 40 mg) was dissolved in 1 mL of MeOH. To the solution was added a solution of 50% aqueous NH₂OH (1 mL) and KOH (50 mg). After stirred at rt for 1 hour, the reaction solution was sent to preparative RP-HPLC to give EXAMPLE 7. MS: calc'd (MH⁺) 285.1, exp (MH⁺) 285.3. $^1$H NMR (CD₃OD, 400 MHz), 8.42 (d, 2H, J=4.8 Hz), 7.22-7.52 (m, 3H), 6.8 (d, 1H, J=4.8 Hz), 4.30 (m, 1H), 2.8-3.2 (m, 4H), 2.25 (m, 1H), 1.9 (m, 1H).

Example 8

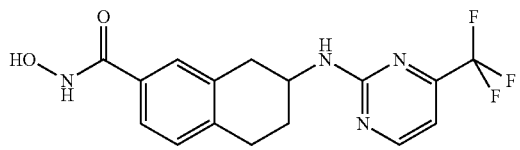 [SMILES: O=C(NO)c1ccc2c(c1)CC(Nc1nccc(C(F)(F)F)n1)CC2]

7-(4-Trifluoromethyl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-trifluoromethyl-pyrimidine instead of 2-chloro-pyrimidine. MS: calc'd (MH⁺) 353.1, exp (MH⁺) 353.3. $^1$H NMR (CD₃OD, 400 MHz), 8.54 (d, 1H, J=4.4 Hz), 7.51 (m, 2H), 7.22 (d, 1H, J=8.4 Hz), 6.91 (d, 1H, J=5.2 Hz), 4.3 (m, 1H), 2.8-3.2 (m, 4H), 2.1 (m, 1H), 1.8 (m, 1H).

Example 9

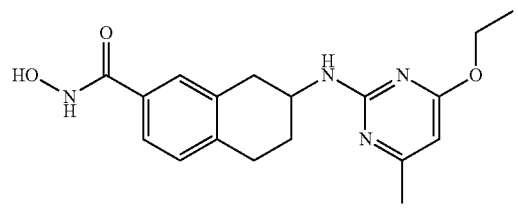 [SMILES: CCOc1cc(C)nc(NC2CCc3ccc(C(=O)NO)cc3C2)n1]

7-(4-Ethoxy-6-methyl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-ethoxy-6-methyl-pyrimidine instead of 2-chloro-pyrimidine. MS: calc'd (MH⁺) 343, exp (MH⁺) 343. $^1$H NMR (CD₃OD, 400 MHz), 7.54 (d, 2H, J=8.4 Hz), 7.24 (d, 1H, J=7.6 Hz), 6.26 (s, 1H), 4.55 (m, 2H), 4.40 (m, 1H), 2.8-3.2 (m, 4H), 2.42 (m, 3H), 2.2 (m, 1H), 1.8 (m, 1H), 1.41 (m, 3H).

Example 10

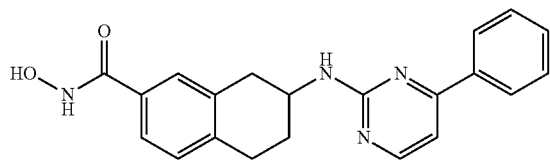 [SMILES: O=C(NO)c1ccc2c(c1)CC(Nc1nccc(-c3ccccc3)n1)CC2]

7-(4-Phenyl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-phenyl-pyrimidine instead of 2-chloro-pyrimidine. MS: calc'd (MH+) 361.1, exp (MH+) 361.4. $^1$H NMR (CD$_3$OD, 400 MHz), 8.34 (d, 1H, J=6 Hz), 8.22 (d, 2H, J=7.6 Hz), 7.5-7.7 (m, 5H), 7.42 (d, 1H, J=5.6 Hz), 7.25 (d, 1H, J=8 Hz), 4.41 (s, 1H), 3.30 (m, 1H), 2.9-3.07 (m, 3H), 2.29 (m, 1H), 1.98 (m, 1H).

Example 11

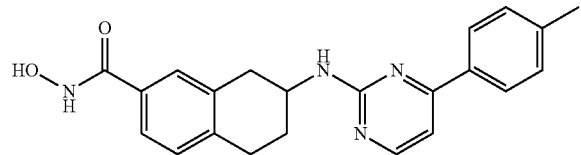 [SMILES: Cc1ccc(-c2ccnc(NC3CCc4ccc(C(=O)NO)cc4C3)n2)cc1]

7-(4-p-Tolyl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-p-tolyl-pyrimidine instead of 2-chloro-pyrimidine. MS: calc'd (MH+) 375.1, exp (MH+) 375.4. $^1$H NMR (CD$_3$OD, 400 MHz), 8.30 (d, 1H, J=6.4 Hz), 8.12 (d, 2H, J=8.0 Hz), 7.54 (m, 2H), 7.38 (d, 3H, J=8.0 Hz), 7.26 (d, 1H, J=8.0 Hz), 4.41 (s, 1H), 3.30 (m, 1H), 3.05 (t, 2H, J=5.6 Hz), 2.90 (m, 1H), 2.45 (s, 3H), 2.28 (m, 1H), 1.94 (m, 1H).

Example 12

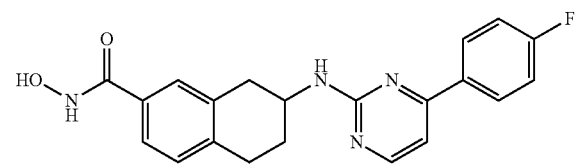 [SMILES: O=C(NO)c1ccc2c(c1)CC(Nc1nccc(-c3ccc(F)cc3)n1)CC2]

7-[4-(4-Fluoro-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(4-fluoro-phenyl)-pyrimidine instead of 2-chloro-pyrimidine. MS: calc'd (MH+) 379.2, exp (MH+) 379.4. $^1$H NMR (CD$_3$OD, 400 MHz), 8.32 (d, 1H, J=6.8 Hz), 8.20 (t, 2H, J=7.2 Hz), 7.53 (m, 2H), 7.20-7.27 (m, 4H), 4.41 (s, 1H), 3.30 (m, 1H), 3.05 (t, 2H, J=5.6 Hz), 2.90 (m, 1H), 2.28 (m, 1H), 1.94 (m, 1H).

Example 13

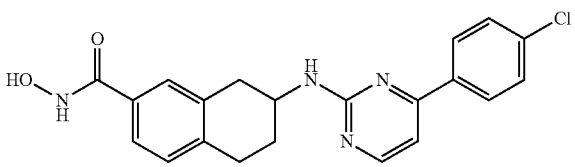 [SMILES: O=C(NO)c1ccc2c(c1)CC(Nc1nccc(-c3ccc(Cl)cc3)n1)CC2]

7-[4-(4-Chloro-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(4-chloro-phenyl)-pyrimidine instead of 2-chloro-pyrimidine. MS: calc'd (MH+) 395, exp (MH+) 395. $^1$H NMR (CD$_3$OD, 400 MHz), 8.35 (d, 1H, J=6.0 Hz), 8.20 (d, 2H, J=8.4 Hz), 7.55 (m, 4H), 7.35 (d, 1H, J=5.6 Hz), 7.25 (d, 1H, J=8.0 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 14

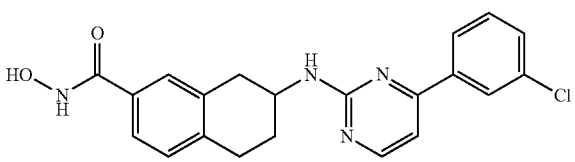 [SMILES: O=C(NO)c1ccc2c(c1)CC(Nc1nccc(-c3cccc(Cl)c3)n1)CC2]

7-[4-(3-Chloro-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(3-chloro-phenyl)-pyrimidine instead of 2-chloro-pyrimidine. MS: calc'd (MH+) 395, exp (MH+) 395. $^1$H NMR (CD$_3$OD, 400 MHz), 8.35 (d, 1H, J=5.2 Hz), 8.14 (m, 1H), 8.02 (m, 1H), 7.46-7.54 (m, 4H), 7.25 (d, 1H, J=8.4 Hz), 7.15 (d, 1H, J=5.2 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 15

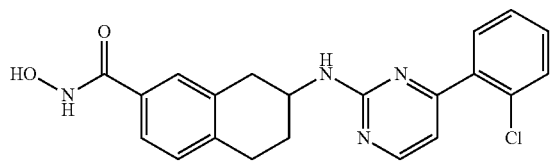 [SMILES: O=C(NO)c1ccc2c(c1)CC(Nc1nccc(-c3ccccc3Cl)n1)CC2]

7-[4-(2-Chloro-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(2-chloro-phenyl)-pyrimidine instead of 2-chloro-pyrimidine. MS: calc'd (MH$^+$) 395, exp (MH$^+$) 395. $^1$H NMR (CD$_3$OD, 400 MHz), 8.35 (d, 1H, J=4.8 Hz), 7.60 (m, 1H), 7.54 (m, 3H), 7.43 (m, 2H), 7.22 (d, 1H, J=8.4 Hz), 6.90 (d, 1H, J=5.2 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 16

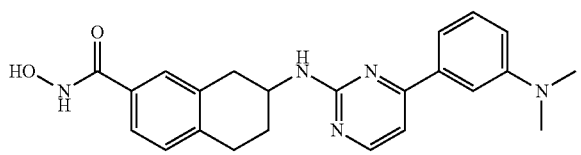 [SMILES: CN(C)c1cccc(-c2ccnc(NC3CCc4ccc(C(=O)NO)cc4C3)n2)c1]

7-[4-(3-Dimethylamino-phenyl)-pyrimidin-2-ylamino]-5,6,7,8-tetrahydro-naphthalene-2-carboxylic acid hydroxyamid The title compound was prepared in analogy to EXAMPLE 7 as shown in Scheme 11, by using [3-(2-chloro-pyrimidin-4-yl)-phenyl]-dimethyl-amine instead of 2-chloro-pyrimidine. MS: calc'd (MH$^+$) 404.2, exp (MH$^+$) 404.5. $^1$H NMR (CD$_3$OD, 400 MHz), 8.30 (d, 1H, J=4.8 Hz), 7.52-7.59 (m, 3H), 7.33-7.43 (m, 2H), 7.18-7.25 (m, 2H), 6.99 (m, 1H), 4.41 (s, 1H), 3.30 (m, 1H), 3.05 (t, 2H, J=5.6 Hz), 3.00 (s, 6H), 2.90 (m, 1H), 2.28 (m, 1H), 1.94 (m, 1H).

Example 17

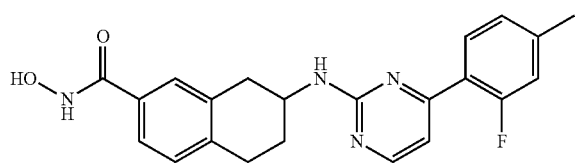 [SMILES: Cc1ccc(-c2ccnc(NC3CCc4ccc(C(=O)NO)cc4C3)n2)c(F)c1]

7-[4-(2-Fluoro-4-methyl-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(2-fluoro-4-methyl-phenyl)-pyrimidine instead of 2-chloro-pyrimidine. MS: calc'd (MH$^+$) 393.2, exp (MH$^+$) 393.4. $^1$H NMR (CD$_3$OD, 400 MHz), 8.34 (d, 1H, J=6.4 Hz), 7.91 (m, 1H), 7.53 (m, 2H), 7.37 (m, 1H), 7.12-7.26 (m, 3H), 4.41 (s, 1H), 3.30 (m, 1H), 3.05 (t, 2H, J=5.6 Hz), 2.90 (m, 1H), 2.40 (s, 3H) 2.28 (m, 1H), 1.94 (m, 1H).

Example 18

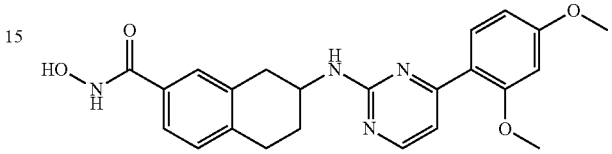

7-[4-(2,4-Dimethoxy-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(2,4-dimethoxy-phenyl)-pyrimidine instead of 2-chloro-pyrimidine. MS: calc'd (MH$^+$) 421.2, exp (MH$^+$) 421.5. $^1$H NMR (CD$_3$OD, 400 MHz), 8.19 (d, 1H, J=7.2 Hz), 7.95 (d, 1H, J=8.0 Hz), 7.51 (m, 2H), 7.23 (m, 2H), 6.63 (m, 2H), 4.41 (s, 1H), 3.30 (m, 1H), 3.91 (s, 3H), 3.87 (s, 3H), 3.05 (t, 2H, J=5.6 Hz), 2.90 (m, 1H), 2.28 (m, 1H), 1.94 (m, 1H).

Example 19

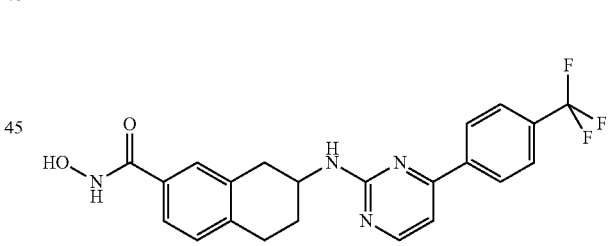

7-[4-(4-Trifluoromethyl-phenyl)-pyrimidin-2-ylamino]-5,6,7,8-tetrahydro-naphthalene-2-carboxylic acid hydroxyamid The title compound was prepared in analogy to EXAMPLE 7 as shown in Scheme 11, by using 2-chloro-4-(4-trifluoromethyl-phenyl)-pyrimidine instead of 2-chloro-pyrimidine. MS: calc'd (MH$^+$) 429.2, exp (MH$^+$) 429.4. $^1$H NMR (CD$_3$OD, 400 MHz), 8.40 (d, 1H, J=5.6 Hz), 8.33 (d, 2H, J=8.0 Hz), 7.83 (d, 2H, J=8.4 Hz), 7.53 (m, 2H), 7.31 (d, 1H, J=5.2 Hz), 7.25 (d, 1H, J=8.4 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 20

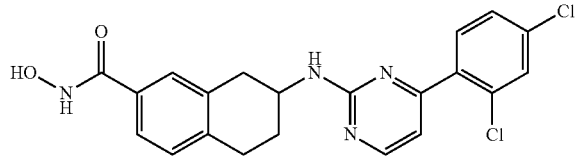 [SMILES: O=C(NO)c1ccc2c(c1)CC(Nc1nccc(-c3ccc(Cl)cc3Cl)n1)CC2]

7-[4-(2,4-Dichloro-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(2,4-dichloro-phenyl)-pyrimidine instead of 2-chloro-pyrimidine. MS: calc'd (MH$^+$) 429.1, exp (MH$^+$) 429.3. $^1$H NMR (CD$_3$OD, 400 MHz), 8.40 (d, 1H, J=5.6 Hz), 7.65-7.70 (m, 2H), 7.50-7.53 (m, 3H), 7.23 (d, 1H, J=8.4 Hz), 7.10 (d, 1H, J=7.2 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 21

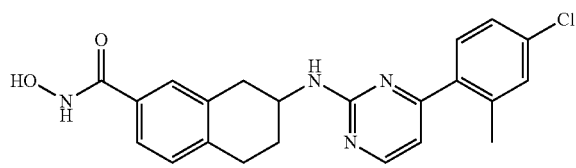 [SMILES: Cc1cc(Cl)ccc1-c1ccnc(NC2CCc3ccc(C(=O)NO)cc3C2)n1]

7-[4-(4-Chloro-2-methyl-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(4-chloro-2-methyl-phenyl)-pyrimidine instead of 2-chloro-pyrimidine. MS: calc'd (MH$^+$) 409.1, exp (MH$^+$) 408.9. $^1$H NMR (CD$_3$OD, 400 MHz), 8.37 (d, 1H, J=6.0 Hz), 7.53 (m, 3H), 7.35-7.40 (m, 2H), 7.23 (d, 1H, J=8.4 Hz), 6.99 (d, 1H, J=6.0 Hz), 4.41 (s, 1H), 3.30 (m, 1H), 3.05 (t, 2H, J=5.6 Hz), 2.90 (m, 1H), 2.51 (s, 3H), 2.28 (m, 1H), 1.94 (m, 1H).

Example 22

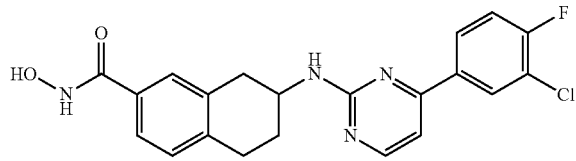 [SMILES: O=C(NO)c1ccc2c(c1)CC(Nc1nccc(-c3ccc(F)c(Cl)c3)n1)CC2]

7-[4-(3-Chloro-4-fluoro-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(3-chloro-4-fluoro-phenyl)-pyrimidine instead of 2-chloro-pyrimidine. MS: calc'd (MH$^+$) 413.1, exp (MH$^+$) 413. $^1$H NMR (CD$_3$OD, 400 MHz), 8.35 (m, 2H), 8.17 (m, 1H), 7.53 (m, 2H), 7.42 (t, 1H, J=8.8 Hz), 7.33 (d, 1H, J=6.4 Hz), 7.25 (d, 1H, J=8.0 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 23

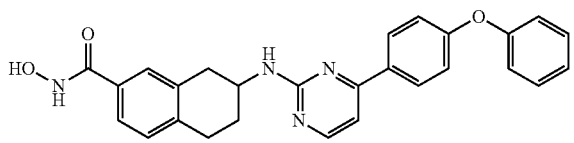 [SMILES: O=C(NO)c1ccc2c(c1)CC(Nc1nccc(-c3ccc(Oc4ccccc4)cc3)n1)CC2]

7-[4-(4-Phenoxy-phenyl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(4-phenoxy-phenyl)-pyrimidine instead of 2-chloro-pyrimidine. MS: calc'd (MH$^+$) 453.2, exp (MH$^+$) 453.5. $^1$H NMR (CD$_3$OD, 400 MHz), 8.27 (d, 1H, J=5.2 Hz), 8.12 (d, 2H, J=8.8 Hz), 7.51 (m, 2H), 7.42 (t, 2H, J=8.0 Hz), 7.18-7.25 (m, 2H), 7.06-7.11 (m, 5H), 4.41 (s, 1H), 3.30 (m, 1H), 3.05 (t, 2H, J=5.6 Hz), 2.90 (m, 1H), 2.28 (m, 1H), 1.94 (m, 1H).

Example 24

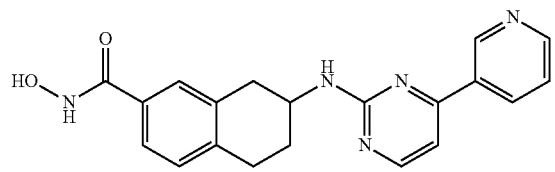

7-(4-Pyridin-3-yl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-pyridin-3-yl-pyrimidine instead of 2-chloro-pyrimidine. MS: calc'd (MH$^+$) 362.1, exp (MH$^+$) 362.4. $^1$H NMR (CD$_3$OD, 400 MHz), 9.48 (s, 1H), 8.99 (d, 1H, J=8 Hz), 8.88 (s, 1H), 8.48 (d, 1H, J=4.8 Hz), 7.99 (m, 1H), 7.52 (m, 2H), 7.43 (d, 1H, J=4.4 Hz), 7.24 (d, 1H, J=8.4 Hz), 2.8-3.2 (m, 5H), 2.29 (m, 1H), 2.00 (m, 1H).

Example 25

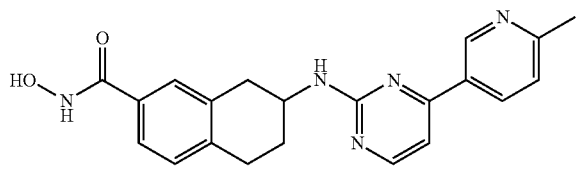 [SMILES: Cc1ccc(-c2ccnc(NC3CCc4ccc(C(=O)NO)cc4C3)n2)cn1]

7-[4-(6-Methyl-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(6-methyl-pyridin-3-yl)-pyrimidine instead of 2-chloro-pyrimidine. MS: calc'd (MH$^+$) 376.2, exp (MH$^+$) 376.4. $^1$H NMR (CD$_3$OD, 400 MHz), 9.35 (s, 1H), 9.02 (d, 1H, J=8.4 Hz), 8.5 (s, 1H), 7.95 (d, 1H, J=8.4 Hz), 7.51 (m, 2H), 7.38 (d, 1H, J=4.4 Hz), 7.25 (d, 1H, J=7.6 Hz), 2.8-3.2 (m, 5H), 2.42 (m, 3H), 2.77 (s, 3H), 2.2 (m, 1H), 1.8 (m, 1H).

Example 26

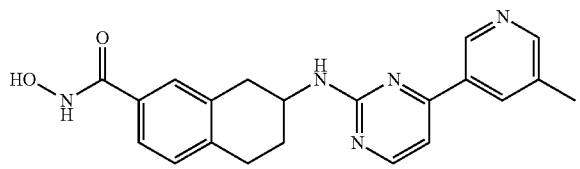 [SMILES: Cc1cncc(-c2ccnc(NC3CCc4ccc(C(=O)NO)cc4C3)n2)c1]

7-[4-(5-Methyl-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(5-methyl-pyridin-3-yl)-pyrimidine instead of 2-chloro-pyrimidine. MS: calc'd (MH$^+$) 376.2, exp (MH$^1$) 376.4. $^1$H NMR (CD$_3$OD, 400 MHz), 9.05 (s, 1H), 8.49 (s, 1H), 8.37 (m, 2H), 8.14 (s, 1H), 7.52 (m, 2H), 7.22 (d, 1H, J=4.4 Hz), 7.18 (d, 1H, J=4.4 Hz), 4.36 (s, 1H), 2.8-3.2 (m, 5H), 2.28 (s, 3H), 2.2 (m, 1H), 1.9 (m, 1H).

Example 27

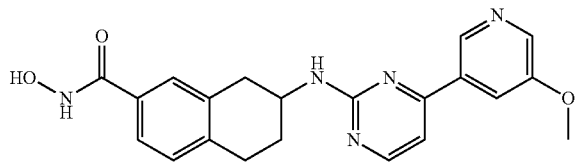 [SMILES: COc1cncc(-c2ccnc(NC3CCc4ccc(C(=O)NO)cc4C3)n2)c1]

7-[4-(5-Methoxy-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(5-methoxy-pyridin-3-yl)-pyrimidine instead of 2-chloro-pyrimidine. MS: calc'd (MH$^+$) 392.2, exp (MH$^+$) 392.4. $^1$H NMR (CD$_3$OD, 400 MHz), 9.10 (s, 1H), 8.65 (s, 1H), 8.56 (s, 1H), 8.50 (d, 1H, J=5.6 Hz), 7.54 (m, 3H), 7.25 (d, 1H, J=8 Hz), 4.08 (s, 3H), 2.8-3.2 (m, 5H), 2.3 (m, 1H), 2.0 (m, 1H).

Example 28

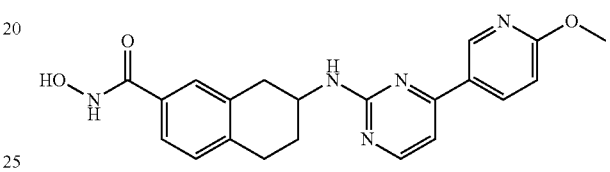

7-[4-(6-Methoxy-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(6-methoxy-pyridin-3-yl)-pyrimidine instead of 2-chloro-pyrimidine. MS: calc'd (MH$^+$) 392.1, exp (MH$^+$) 392.4. $^1$H NMR (CD$_3$OD, 400 MHz), 9.10 (d, 1H, J=2.4 Hz), 8.50-8.53 (m, 1H), 8.31 (d, 1H, J=6.4 Hz), 7.54 (m, 3H), 7.25 (d, 1H, J=8 Hz), 7.00 (d, 1H, J=8.8 Hz), 4.08 (s, 3H), 2.8-3.2 (m, 5H), 2.3 (m, 1H), 2.0 (m, 1H).

Example 29

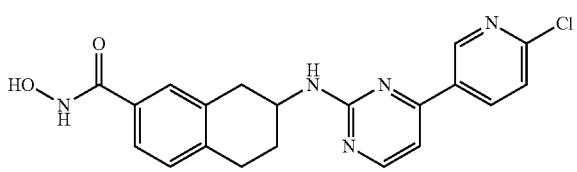 [SMILES: O=C(NO)c1ccc2c(c1)CC(Nc1nccc(-c3ccc(Cl)nc3)n1)CC2]

7-[4-(6-Chloro-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(6-chloro-pyridin-3-yl)-pyrimidine instead of 2-chloro-pyrimidine. MS: calc'd (MH$^+$) 396.1, exp (MH$^+$) 396.8. $^1$H NMR (CD$_3$OD, 400 MHz), 9.16 (d, 1H, J=2.4 Hz), 8.56 (m, 1H), 8.41 (d, 1H, J=6 Hz), 7.52-7.65 (m, 3H), 7.41 (d, 1H, J=5.6 Hz), 7.26 (d, 1H, J=8 Hz), 4.37 (s, 1H), 2.8-3.2 (m, 4H), 2.3 (m, 1H), 2.0 (m, 1H).

Example 30

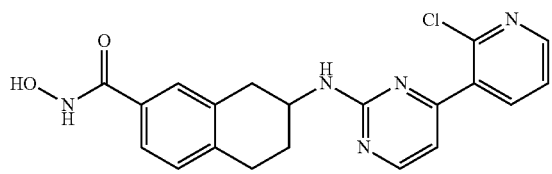 [SMILES: O=C(NO)c1ccc2c(c1)CC(Nc1nccc(-c3cccnc3Cl)n1)CC2]

7-[4-(2-Chloro-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(2-chloro-pyridin-3-yl)-pyrimidine instead of 2-chloro-pyrimidine. MS: calc'd (MH+) 396.1, exp (MH+) 396.8. $^1$H NMR (CD$_3$OD, 400 MHz), 8.4-8.6 (m, 2H), 8.15 (d, 1H, J=6.8 Hz), 7.50-7.57 (m, 3H), 7.23 (d, 1H, J=8.4 Hz), 7.16 (d, 1H, J=5.2 Hz), 4.37 (s, 1H), 2.8-3.2 (m, 4H), 2.3 (m, 1H), 2.0 (m, 1H).

Example 31

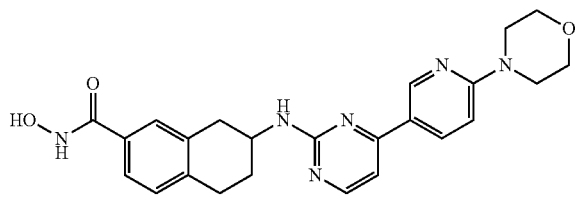 [SMILES: O=C(NO)c1ccc2c(c1)CC(Nc1nccc(-c3ccc(N4CCOCC4)nc3)n1)CC2]

7-[4-(6-Morpholin-4-yl-pyridin-3-yl)-pyrimidin-2-ylamino]-5,6,7,8-tetrahydro-naphthalene-2-carboxylic acid hydroxyamide The title compound was prepared in analogy to EXAMPLE 7 as shown in Scheme 11, by using 2-chloro-4-(6-morpholin-yl-pyridin-3-yl)-pyrimidine instead of 2-chloro-pyrimidine. MS: calc'd (MH+) 447.2, exp (MH+) 447.5. $^1$H NMR (CD$_3$OD, 400 MHz), 9.02 (s, 1H), 8.43 (m, 1H), 8.20 (d, 1H, J=6.4 Hz), 7.56 (m, 2H), 7.43 (d, 1H, J=6.8 Hz), 7.26 (m, 1H), 7.04 (d, 1H, J=9.6 Hz), 3.77-3.82 (m, 8H), 2.8-3.2 (m, 5H), 2.2 (m, 1H), 2.0 (m, 1H).

Example 32

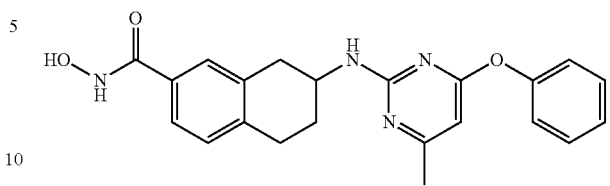

7-(4-Methyl-6-phenoxy-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-methyl-6-phenoxy-pyrimidine instead of 2-chloro-pyrimidine. MS: calc'd (MH+) 391.2, exp (MH+) 391.4. $^1$H NMR (CD$_3$OD, 400 MHz), 7.42-7.49 (m, 4H), 7.15-7.28 (m, 4H) 6.42 (s, 1H), 3.85 (m, 1H), 2.8-3.2 (m, 4H), 2.46 (s, 3H), 2.1 (m, 1H), 1.8 (m, 1H).

Example 33

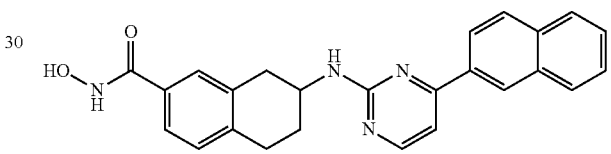

7-(4-Naphthalen-2-yl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-4-naphthalen-2-yl-pyrimidine instead of 2-chloro-pyrimidine. MS: calc'd (MH+) 411.2, exp (MH+) 411.5. $^1$H NMR (CD$_3$OD, 400 MHz), 8.75 (m, 1H), 8.37 (d, 1H, J=6.4 Hz), 8.28 (d, 1H, J=8.8 Hz), 7.94-8.06 (m, 3H), 7.51-7.63 (m, 5H), 7.27 (d, 1H, J=7.6 Hz), 4.41 (s, 1H), 3.30 (m, 1H), 3.05 (t, 2H, J=5.6 Hz), 2.90 (m, 1H), 2.28 (m, 1H), 1.94 (m, 1H).

Example 34

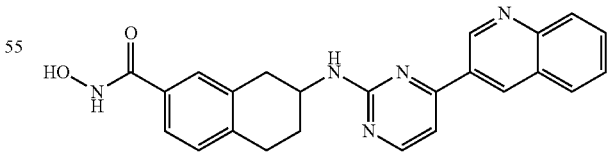

7-(4-Quinolin-3-yl-pyrimidin-2-ylamino)-5,6,7,8-tetrahydro-naphthalene-2-carboxylic acid hydroxyamide The title compound was prepared in analogy to EXAMPLE 7 as shown in Scheme 11, by using 3-(2-chloropyrimidin-4-yl)-quinoline instead of 2-chloro-pyrimidine. MS: calc'd (MH+) 412.1, exp (MH+) 412.5. $^1$H NMR (CD$_3$OD, 400 MHz), 9.78 (s, 1H), 9.53 (s, 1H), 8.51 (d, 1H, J=5.6 Hz), 8.31 (d, 1H, J=8 Hz), 8.23 (d, 1H, J=8.4 Hz), 8.11 (t, 1H, J=8 Hz), 7.90 (m, 1H), 7.51 (m, 3H), 7.28 (d, 1H, J=5.6 Hz), 2.8-3.2 (m, 5H), 2.2 (m, 1H), 2.0 (m, 1H).

Example 35

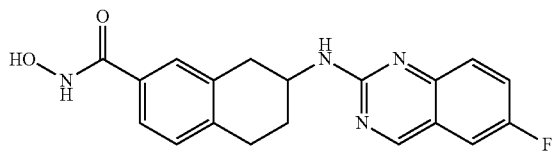 [SMILES: O=C(NO)c1ccc2c(c1)CC(Nc1ncc3cc(F)ccc3n1)CC2]

7-(6-Fluoro-quinazolin-2-ylamino)-5,6,7,8-tetrahydro-naphthalene-2-carboxylic acid hydroxyamide The title compound was prepared in analogy to EXAMPLE 7 as shown in Scheme 11, by using 2-chloro-6-fluoro-quinazoline instead of 2-chloro-pyrimidine. MS: calc'd (MH+) 353.1, exp (MH+) 353.4. $^1$H NMR (CD$_3$OD, 400 MHz), 7.55-7.66 (m, 4H), 7.25 (m, 3H), 5.79 (s, 1H), 4.41 (s, 1H), 2.8-3.2 (m, 3H), 2.28 (m, 1H), 1.9 (m, 1H).

Example 36

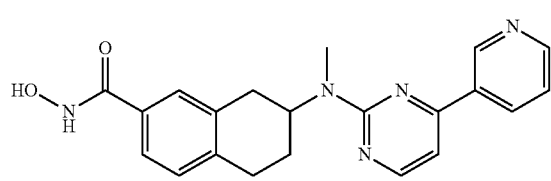 [SMILES: CN(c1nccc(-c2cccnc2)n1)C1CCc2ccc(C(=O)NO)cc2C1]

7-[Methyl-(4-pyridin-3-yl-pyrimidin-2-yl)-amino]-5,6,7,8-tetrahydro-naphthalene-2-carboxylic acid hydroxyamide The title compound was prepared according to Scheme 4 by N-methylation of appropriate starting material. MS: calc'd (MH+) 376.1, exp (MH+) 376.4. $^1$H NMR (CD$_3$OD, 400 MHz), 9.34 (s, 1H), 8.72 (m, 2H), 8.50 (d, 1H, J=4.8 Hz), 7.5 (m, 1H), 7.4-7.5 (m, 4 Hz), 5.20 (s, 2H), 3.2 (s, 3H), 2.9-3.07 (m, 4H), 2.12 (m, 2H).

Example 37

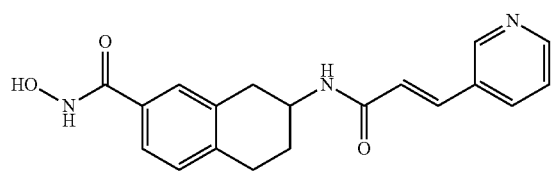 [SMILES: O=C(/C=C/c1cccnc1)NC1CCc2ccc(C(=O)NO)cc2C1]

7-((E)-3-Pyridin-3-yl-acryloylamino)-5,6,7,8-tetrahydro-naphthalene-2-carboxylic acid hydroxyamide The title compound was prepared in two steps according to Scheme 5 by (1) treating amine VII with (E)-3-pyridin-3-yl-acrylic acid, EDCI, HOBt, and TEA in dichloromethane, and (2) treating the ester intermediate with aqueous HONH$_2$ and KOH. MS: calc'd (MH+) 338.1, exp (MH+) 338.4. $^1$H NMR (CD$_3$OD, 400 MHz), 9.07 (s, 1H), 8.82 (m, 2H). 8.11 (m, 1H), 7.7 (m, 1H, J=15.6 Hz), 7.52 (m, 2H), 7.22 (m, 1H), 7.7 (d, 1H, J=16 Hz), 4.29 (m, 1H), 2.8-3.2 (m, 4H), 2.25 (m, 1H), 1.9 (m, 1H).

Example 38

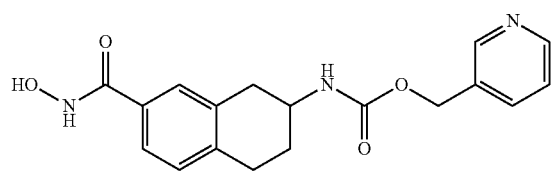 [SMILES: O=C(NC1CCc2ccc(C(=O)NO)cc2C1)OCc1cccnc1]

7-Hydroxycarbamoyl-1,2,3,4-tetrahydro-naphthalen-2-yl)-carbamic acid pyridin-3-ylmethyl ester The title compound was prepared in two steps according to Scheme 5 by (1) treating amine VII with pyridin-3-yl-methoxycarbonyl chloride and TEA in dichloromethane, and (2) treating the ester intermediate with aqueous HONH$_2$ and KOH. MS: calc'd (MH+) 342.1, exp (MH+) 342.4. $^1$H NMR (CD$_3$OD, 400 MHz), 8.91 (s, 1H), 8.84 (d, 1H, J=5.6 Hz), 8.64 (d, 1H, J=8 Hz), 8.11 (m, 1H), 7.49 (m, 2H), 7.2 (d, 1H, J=8.4 Hz), 5.34 (s, 2H), 3.88 (m, 1H), 2.8-3.2 (m, 4H), 2.1 (m, 1H), 1.8 (m, 1H).

Example 39

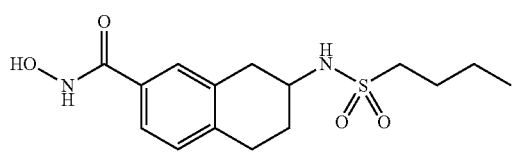 [SMILES: CCCCS(=O)(=O)NC1CCc2ccc(C(=O)NO)cc2C1]

7-(Butane-1-sulfonylamino)-5,6,7,8-tetrahydro-naphthalene-2-carboxylic acid hydroxyamid The title compound was prepared in two steps according to Scheme 6 by (1) treating amine VII with n-butylsulfonyl chloride and TEA in dichloromethane, and (2) treating the ester intermediate with aqueous HONH$_2$ and KOH. MS: calc'd (MH+) 327, exp (MH+) 327.4. $^1$H NMR (CD$_3$OD, 400 MHz), 7.50 (d, 1H, J=7.6 Hz), 7.49 (s, 1H), 7.19 (d, 1H, J=8.0

Hz), 3.68 (m, 1H), 3.14 (m, 3H), 2.79-3.00 (m, 3H), 2.16 (m, 1H), 1.82 (m, 3H), 1.50 (m, 2H), 0.99 (m, 3H).

Example 40

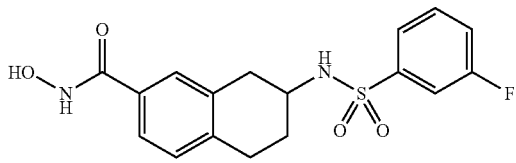 [SMILES: O=C(NO)c1ccc2c(c1)CC(NS(=O)(=O)c1cccc(F)c1)CC2]

7-(3-Fluoro-benzenesulfonylamino)-5,6,7,8-tetrahydro-naphthalene-2-carboxylic acid hydroxyamide The title compound was prepared in two steps according to Scheme 6 by (1) treating amine VII with 3-fluorobenzenesulfonyl chloride and TEA in dichloromethane, and (2) treating the ester intermediate with aqueous HONH$_2$ and KOH. MS: calc'd (MH$^+$) 365, exp (MH$^+$) 365.4. $^1$H NMR (CD$_3$OD, 400 MHz), 7.75 (d, 1H, J=8.0 Hz), 7.60-7.66 (m, 2H), 7.46 (d, 1H, J=8.0 Hz), 7.41 (m, 1H), 7.36 (s, 1H), 7.14 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 41

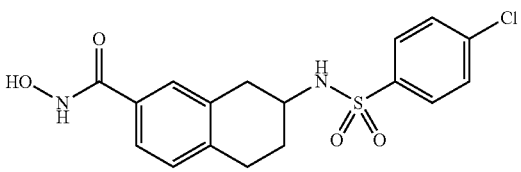 [SMILES: O=C(NO)c1ccc2c(c1)CC(NS(=O)(=O)c1ccc(Cl)cc1)CC2]

7-(4-Chloro-benzenesulfonylamino)-5,6,7,8-tetrahydro-naphthalene-2-carboxylic acid hydroxyamide The title compound was prepared in two steps according to Scheme 6 by (1) treating amine VII with 4-chlorobenzenesulfonyl chloride and TEA in dichloromethane, and (2) treating the ester intermediate with aqueous HONH$_2$ and KOH. MS: calc'd (MH$^+$) 381, exp (MH$^+$) 381. $^1$H NMR (CD$_3$OD, 400 MHz), 7.90 (d, 2H, J=8.4 Hz), 7.60 (d, 2H, J=8.4 Hz), 7.47 (d, 1H, J=8.0 Hz), 7.37 (s, 1H), 7.15 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 42

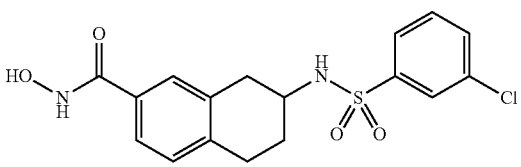 [SMILES: O=C(NO)c1ccc2c(c1)CC(NS(=O)(=O)c1cccc(Cl)c1)CC2]

7-(3-Chloro-benzenesulfonylamino)-5,6,7,8-tetrahydro-naphthalene-2-carboxylic acid hydroxyamide The title compound was prepared in two steps according to Scheme 6 by (1) treating amine VII with 3-chlorobenzenesulfonyl chloride and TEA in dichloromethane, and (2) treating the ester intermediate with aqueous HONH$_2$ and KOH. MS: calc'd (MH$^+$) 381, exp (MH$^+$) 381. $^1$H NMR (CD$_3$OD, 400 MHz), 7.90 (m, 1H), 7.84 (d, 1H, J=8.0 Hz), 7.66 (d, 1H, J=8.4 Hz), 7.59 (t, 1H, J=8.0 Hz), 7.47 (d, 1H, J=8.0 Hz), 7.36 (s, 1H), 7.15 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 43

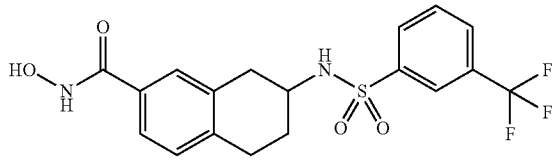 [SMILES: O=C(NO)c1ccc2c(c1)CC(NS(=O)(=O)c1cccc(C(F)(F)F)c1)CC2]

7-(3-Trifluoromethyl-benzenesulfonylamino)-5,6,7,8-tetrahydro-naphthalene-2-carboxylic acid hydroxyamid The title compound was prepared in two steps according to Scheme 6 by (1) treating amine VII with 3-trifluoromethyl-benzenesulfonyl chloride and TEA in dichloromethane, and (2) treating the ester intermediate with aqueous HONH$_2$ and KOH. MS: calc'd (MH$^+$) 415, exp (MH$^+$) 415.4. $^1$H NMR (CD$_3$OD, 400 MHz), 8.20 (s, 1H), 8.18 (d, 1H, J=8.8 Hz), 7.97 (d, 1H, J=8.0 Hz), 7.82 (t, 1H, J=7.6 Hz), 7.46 (d, 1H, J=7.6 Hz), 7.36 (s, 1H), 7.15 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 44

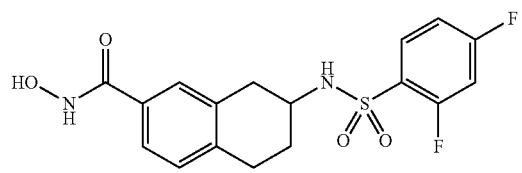 [SMILES: O=C(NO)c1ccc2c(c1)CC(NS(=O)(=O)c1ccc(F)cc1F)CC2]

7-(2,4-Difluoro-benzenesulfonylamino)-5,6,7,8-tetrahydro-naphthalene-2-carboxylic acid hydroxyamide The title compound was prepared in two steps according to Scheme 6 by (1) treating amine VII with 2,4-difluorobenzenesulfonyl chloride and TEA in dichloromethane, and (2) treating the ester intermediate with aqueous HONH$_2$ and KOH. MS: calc'd (MH$^+$) 383, exp (MH$^+$) 383.4. $^1$H NMR (CD$_3$OD, 400 MHz), 7.97 (m, 1H), 7.47 (d, 1H, J=8.0 Hz), 7.37 (s, 1H), 7.24 (m, 1H), 7.18 (m, 2H), 3.55 (m, 1H), 2.95 (m, 2H), 2.82 (m, 1H), 2.69 (m, 1H), 1.95 (m, 1H) 1.73 (m, 1H).

Example 45

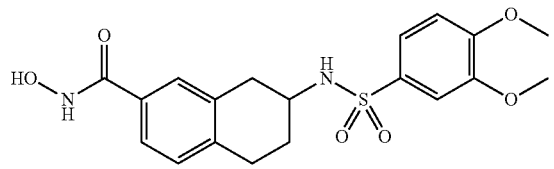 [SMILES: COc1ccc(S(=O)(=O)NC2CCc3ccc(C(=O)NO)cc3C2)cc1OC]

7-(3,4-Dimethoxy-benzenesulfonylamino)-5,6,7,8-tetrahydro-naphthalene-2-carboxylic acid hydroxyamide The title compound was prepared in two steps according to Scheme 6 by (1) treating amine VII with 3,4-dimethoxybenzenesulfonyl chloride and TEA in dichloromethane, and (2) treating the ester intermediate with aqueous $HONH_2$ and KOH. MS: calc'd ($MH^+$) 407, exp ($MH^+$) 407.5. $^1$H NMR ($CD_3OD$, 400 MHz), 7.51 (dd, 1H, $J_1$=8.4 Hz, $J_2$=2.0 Hz), 7.46 (d, 1H, J=8.0 Hz), 7.42 (d, 1H, J=1.6 Hz), 7.35 (s, 1H), 7.11 (m, 2H), 3.92 (s, 3H), 3.88 (s, 3H), 3.55 (m, 1H), 2.95 (m, 2H), 2.82 (m, 1H), 2.69 (m, 1H), 1.95 (m, 1H) 1.73 (m, 1H).

Example 46

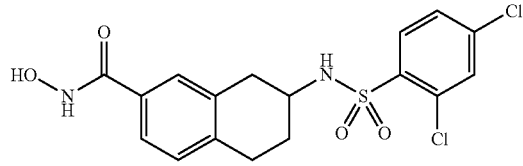 [SMILES: O=C(NO)c1ccc2c(c1)CC(NS(=O)(=O)c1ccc(Cl)cc1Cl)CC2]

7-(2,4-Dichloro-benzenesulfonylamino)-5,6,7,8-tetrahydro-naphthalene-2-carboxylic acid hydroxyamide The title compound was prepared in two steps according to Scheme 6 by (1) treating amine VII with 2,4-dichlorobenzenesulfonyl chloride and TEA in dichloromethane, and (2) treating the ester intermediate with aqueous $HONH_2$ and KOH. MS: calc'd ($MH^+$) 415, exp ($MH^+$) 415.3. $^1$H NMR ($CD_3OD$, 400 MHz), 8.09 (d, 1H, J=8.4 Hz), 7.70 (d, 1H, J=2.0 Hz), 7.54 (dd, 1H, $J_1$=8.4 Hz, $J_2$=2.0 Hz), 7.46 (d, 1H, J=8.0 Hz), 7.33 (s, 1H), 7.14 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 47

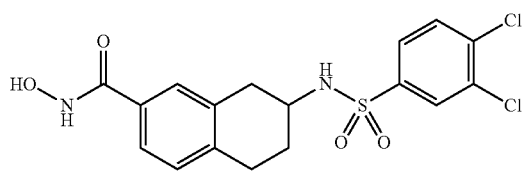 [SMILES: O=C(NO)c1ccc2c(c1)CC(NS(=O)(=O)c1ccc(Cl)c(Cl)c1)CC2]

7-(3,4-Dichloro-benzenesulfonylamino)-5,6,7,8-tetrahydro-naphthalene-2-carboxylic acid hydroxyamide The title compound was prepared in two steps according to Scheme 6 by (1) treating amine VII with 3,4-dichlorobenzenesulfonyl chloride and TEA in dichloromethane, and (2) treating the ester intermediate with aqueous $HONH_2$ and KOH. MS: calc'd ($MH^+$) 415, exp ($MH^+$) 415.3. $^1$H NMR ($CD_3OD$, 400 MHz), 8.05 (d, 1H, J=2.0 Hz), 7.82 (dd, 1H, $J_1$=8.4 Hz, $J_2$=2.0 Hz), 7.76 (d, 1H, J=8.4 Hz), 7.46 (d, 1H, J=8.0 Hz), 7.33 (s, 1H), 7.14 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 48

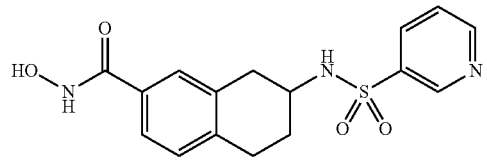 [SMILES: O=C(NO)c1ccc2c(c1)CC(NS(=O)(=O)c1cccnc1)CC2]

7-(Pyridine-3-sulfonylamino)-5,6,7,8-tetrahydro-naphthalene-2-carboxylic acid hydroxyamide The title compound was prepared in two steps according to Scheme 6 by (1) treating amine VII with pyridine-3-sulfonyl chloride and TEA in dichloromethane, and (2) treating the ester intermediate with aqueous $HONH_2$ and KOH. MS: calc'd ($MH^+$) 348, exp ($MH^+$) 348.4. $^1$H NMR ($CD_3OD$, 400 MHz), 9.05 (s, 1H), 8.80 (d, 1H, J=4.4 Hz), 7.31 (d, 1H, J=8.0 Hz), 7.65 (m, 1H), 7.47 (d, 1H, J=8.0 Hz), 7.36 (s, 1H), 7.16 (d, 1H, J=8.0 Hz), 3.55 (m, 1H), 2.95 (m, 2H), 2.82 (m, 1H), 2.69 (m, 1H), 1.95 (m, 1H) 1.73 (m, 1H).

Example 49

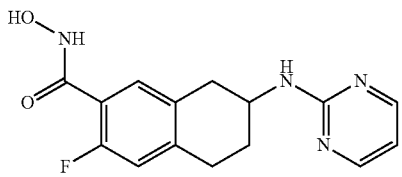 [SMILES: O=C(NO)c1cc2c(cc1F)CCC(Nc1ncccn1)C2]

3-Fluoro-7-(pyrimidin-2-ylamino)-5,6,7,8-tetrahydro-naphthalene-2-carboxylic acid hydroxyamide The title compound was prepared according to Scheme 7 and the synthesis was in close analogy to that of EXAMPLE 7. A detailed method was provided as shown in Scheme 12.

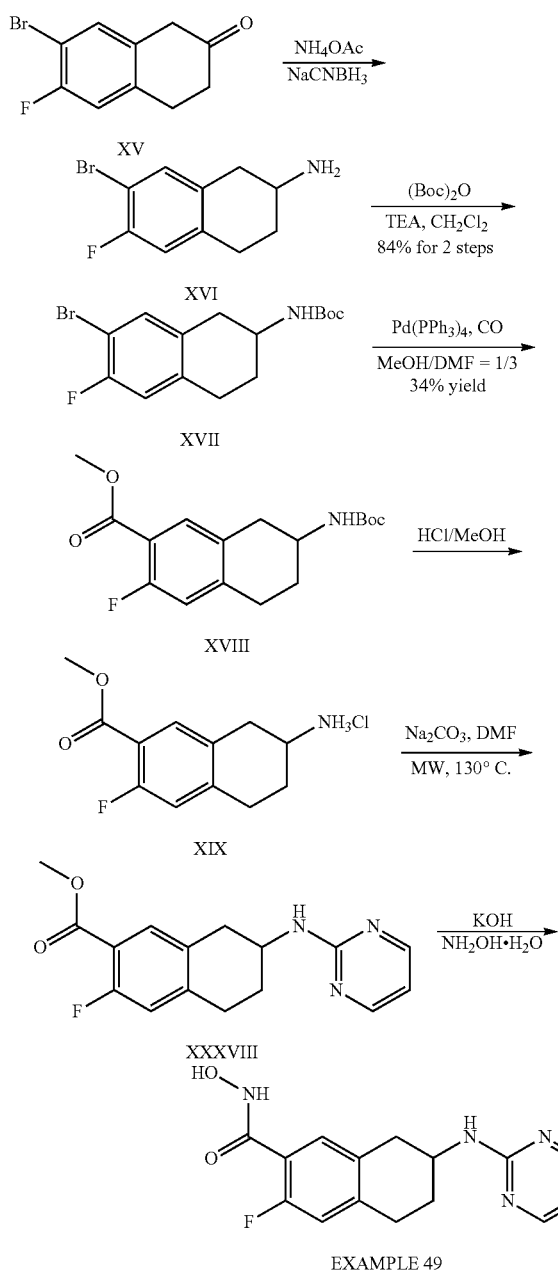

7-Bromo-6-fluoro-1,2,3,4-tetrahydro-naphthalen-2-ylamine XVI was prepared from commercial available 7-bromo-6-fluoro-3,4-dihydro-1H-naphthalen-2-one XV. To a stirred solution of XV (0.10 g, 0.41 mmol) in 3 mL of MeOH was added NH$_4$OAc, followed by NaCNBH$_3$ (0.018 g) in one portion at ambient temperature. The reaction mixture was stirred at ambient temperature for 16 h. Removal of solvent under vacuum gave the crude product, which was partitioned between 2N Na$_2$CO$_3$ and CH$_2$Cl$_2$. The organic layer was separated and dried over MgSO$_4$. The solvent was removed under vacuum and the so-obtained crude product was dissolved in 2 mL of CH$_2$Cl$_2$. To this solution was added TEA (0.12 mL) and (Boc)$_2$O (90 mg, 0.41 mmol). The reaction mixture was stirred at rt overnight. Removal of the solvent under vacuum gave the crude product, which was purified by column to give the pure product XVII (119 mg, 84% over 2 steps). MS: calc'd (MH$^+$) 344, exp (MH$^+$) 344.

7-Amino-3-fluoro-5,6,7,8-tetrahydro-naphthalene-2-carboxylic acid methyl ester XIX was made in two steps from XVII. To a stirred solution of 7-bromo-6-fluoro-1,2,3,4-tetrahydro-naphthalen-2-ylamine XVII (1.0 g, 2.9 mmol) in a mixed solvent (DMF/MeOH, 3/1, 15 mL) was added DIPEA (1.0 mL) and Pd (Ph$_3$)$_4$ (0.34 g, 0.29 mmol). The system was evacuated and refilled with CO gas for 3 times. After that, the reaction mixture was stirred at 80° C. under CO balloon pressure for 18 h before quenching with water. The reaction mixture was extracted with EtOAc and dried over MgSO$_4$. After removal of solvent, the residue was purified by column to afford the product XVIII (320 mg, 34%). MS: calc'd (MH$^+$) 324, exp (MH$^+$) 324. To the above product XVIII (0.20 g, 0.62 mmol) was added 4 mL of MeOH saturated with HCl gas. The reaction mixture was stirred at rt for 2 h. Removal of the solvent gave the crude product XIX as its HCl salt, which was used directly in next step reaction. MS: calc'd (MH$^+$) 224, exp (MH$^+$) 224.

7-Amino-3-fluoro-5,6,7,8-tetrahydro-naphthalene-2-carboxylic acid methyl ester XIX (0.05 g, 0.224 mmol) and 2-chloro-pyrimidine (0.05 g, 0.45 mmol) were dissolved in 1 mL of DMF followed by the addition of Na$_2$CO$_3$ (0.06 g, 0.56 mmol). The reaction mixture was heated in a microwave reactor (130° C.) for 2 h. After it was cooled to rt, the reaction mixture was diluted with water and extracted with EtOAc. The combined organic layer was dried over MgSO$_4$. The solvent was removed on vacuum and the residue was purified by column to afford the product XXXVIII. MS: calc'd (MH$^+$) 302, exp (MH$^+$) 302.

The above methyl ester XXXVIII (8 mg, 0.026 mmol) was dissolved in a mixed solvent (MeOH/NH$_2$OH.H$_2$O, 1/1, 0.6 mL) and followed by the addition of KOH (10 mg). The reaction mixture was stirred at rt for 1 hour and submitted to HPLC separation to afford the titled compound (4 mg, 50%), EXAMPLE 49. MS: calc'd (MH$^+$) 303, exp (MH$^+$) 303.3. $^1$H NMR (CD$_3$OD, 400 MHz) δ 8.30 (d, J=4.8

Example 50

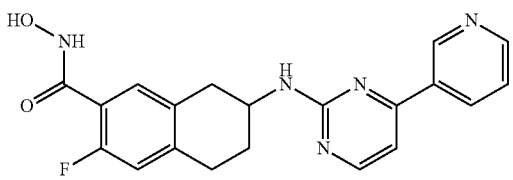 [SMILES: O=C(NO)c1cc2c(cc1F)CCC(Nc1nccc(-c3cccnc3)n1)C2]

3-Fluoro-7-(4-pyridin-3-yl-pyrimidin-2-ylamino)-5,6,7,8-tetrahydro-naphthalene-2-carboxylic acid hydroxyamide The title compound was prepared in analogy to EXAMPLE 49 as shown in Scheme 12, by using 2-chloro-4-pyridin-3-yl-pyrimidine instead of 2-chloro-pyrimidine. MS: calc'd (MH$^+$) 380.1, exp (MH$^+$) 380.4. $^1$H NMR (CD$_3$OD, 400 MHz) δ 9.50 (d, J=1.6 Hz, 1H), 9.07 (d, J=1.6 Hz, 1H), 8.91 (d, J=4.4 Hz, 1H), 8.50 (d, J=5.6 Hz, 1H), 8.02 (dd, $J_1$=8.0, $J_2$=5.6 Hz, 1H), 7.48 (d, J=7.2 Hz, 1H), 7.46 (d, J=8.4 Hz, 1H), 7.01 (d, J=11.6 Hz, 1H), 4.48 (br s, 1H), 3.37 (d, J=3.6 Hz, 1H), 3.06 (t, J=6.4 Hz, 2H), 2.88 (d, $J_1$=16.0, $J_2$=9.6 Hz, 1H), 2.29-2.27 (m, 1H), 2.01-1.92 (m, 1H).

Example 51

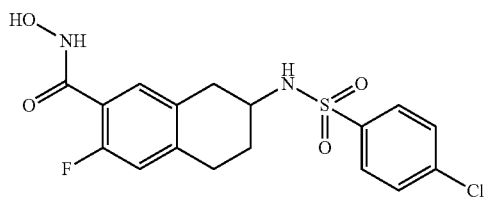 [SMILES: O=C(NO)c1cc2c(cc1F)CCC(NS(=O)(=O)c1ccc(Cl)cc1)C2]

7-(4-Chloro-benzenesulfonylamino)-3-fluoro-5,6,7,8-tetrahydro-naphthalene-2-carboxylic acid hydroxyamide The title compound was synthesized in analogy to Scheme 6. A detailed procedure was provided in Scheme 13.

Scheme 13

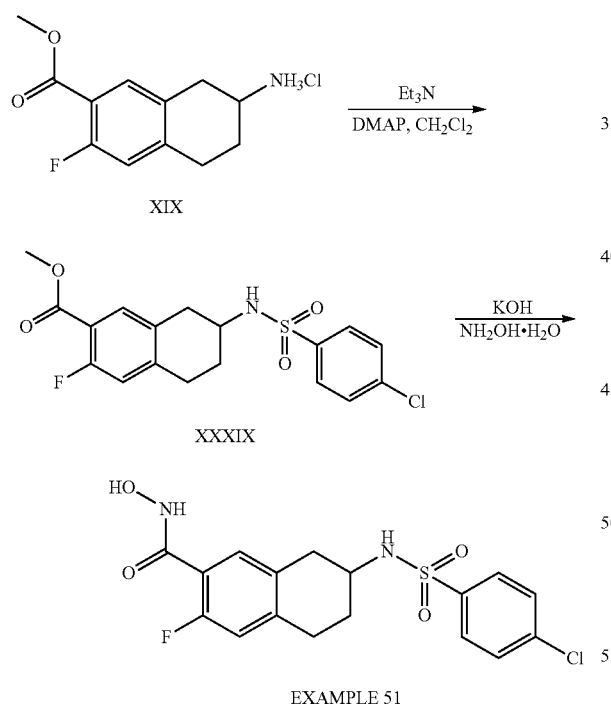

EXAMPLE 51

To a stirred solution of 7-amino-3-fluoro-5,6,7,8-tetrahydro-naphthalene-2-carboxylic acid methyl ester XIX (0.048 g, 0.216 mmol) in 2 mL of $CH_2Cl_2$ was added TEA (0.2 mL) and catalytic amount of DMAP, followed by the addition of 4-chlorobenzenesulfonylchloride (69 mg, 0.325 mmol) at 0° C. After the reaction mixture was stirred at rt for 2 hours, it was quenched with satd. $NaHCO_3$, extracted with $CH_2Cl_2$, dried over $MgSO_4$. Purification by silica gel column gave the ester product XXXIX (69 mg, 80%). MS: calc'd ($MH^+$) 398, exp ($MH^+$) 398. The above methyl ester XXXIX (69 mg, 0.173 mmol) was dissolved in a mixed solvent (MeOH/$NH_2OH.H_2O$, 1/1, 4.0 mL) and followed by the addition of KOH (72 mg). The reaction mixture was stirred at rt for 1 hour and submitted to HPLC separation to afford the titled compound, EXAMPLE 51. MS: calc'd ($MH^+$) 399, exp ($MH^+$) 399.8. $^1$H NMR ($CD_3OD$, 400 MHz) δ 7.90 (dd, J=6.8, 1.6 Hz, 2H), 7.61 (dd, J=6.8, 1.6 Hz, 2H), 7.30 (d, J=7.2 Hz, 1H), 6.92 (d, J=11.6 Hz, 1H), 3.57-3.51 (m, 1H), 2.95-2.87 (m, 2H), 2.85-2.76 (m, 1H), 2.64 (dd, $J_1$=16.4, $J_2$=8.8 Hz, 1H), 1.94-1.89 (m, 1H), 1.77-1.70 (m, 1H).

Example 52

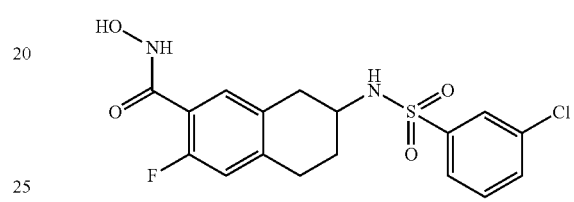

7-(3-Chloro-benzenesulfonylamino)-3-fluoro-5,6,7,8-tetrahydro-naphthalene-2-carboxylic acid hydroxyamide The title compound was prepared in analogy to EXAMPLE 51 as shown in Scheme 13, by using 3-chlorobenzensulfonylchloride instead of 4-chlorobenzensulfonylchloride. MS: calc'd ($MH^+$) 399, exp ($MH^+$) 399.8. $^1$H NMR ($CD_3OD$, 400 MHz), 7.90 (d, J=1.6 Hz, 1H), 7.84 (d, J=7.6 Hz, 1H), 7.67 (dt, $J_1$=7.2, $J_2$=3.4 Hz, 1H), 7.59 (t, J=8.0 Hz, 1H), 7.29 (d, J=7.2 Hz, 1H), 6.92 (d, J=11.2 Hz, 1H), 3.60-3.53 (m, 1H), 2.95-2.85 (m, 2H), 2.83-2.77 (m, 1H), 2.65 (dd, $J_1$=16.4, $J_2$=8.4 Hz, 1H), 1.94-1.90 (m, 1H), 1.78-1.74 (m, 1H).

Example 53

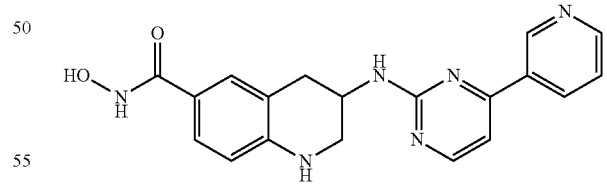

3-(Pyridin-3-yl-pyrimidine-2-ylamino)-1,2,3,4-tetrahydro-quinoline-6-carboxylic acid hydroxyamide The title compound was prepared according to Scheme 8 by treating intermediate XXVI with appropriately substituted 2-chloropyrimidine and conversion of ester functional group to hydroxamic acid. A detailed synthesis procedure is provided as Scheme 14.

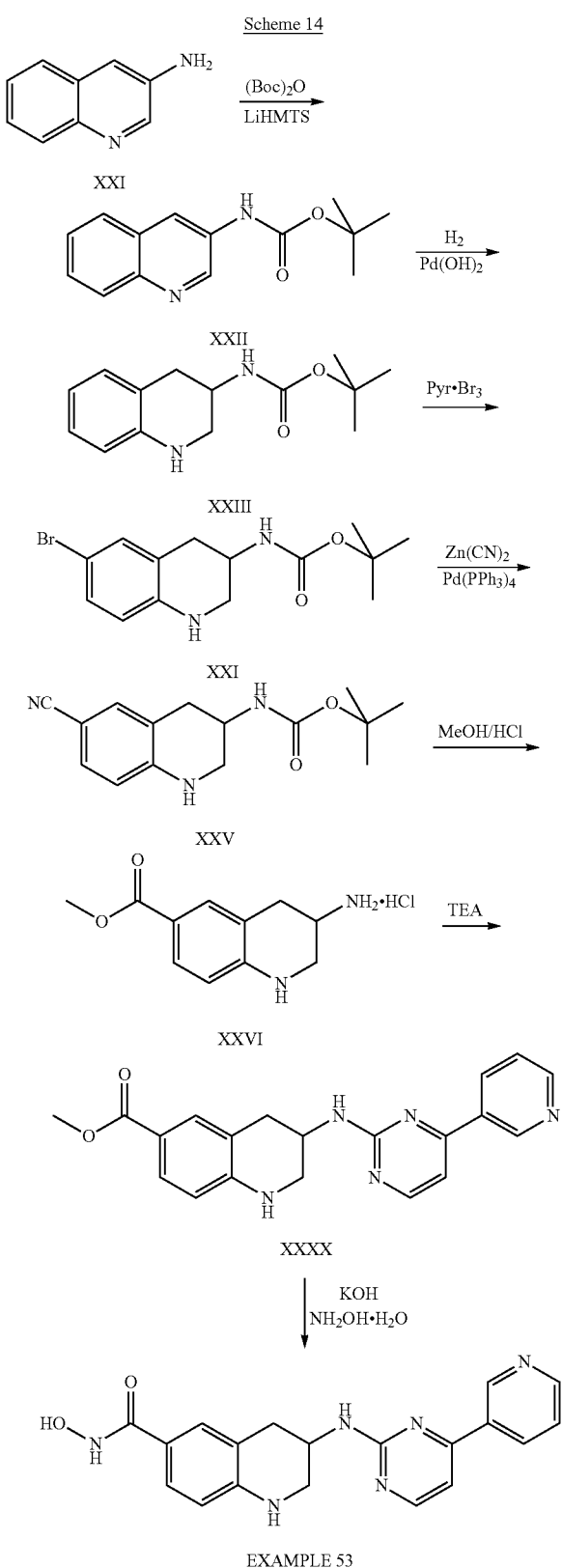

Scheme 14

EXAMPLE 53

To a solution of 3-aminoquinoline XXI (4.32 g, 30 mmol) in 100 mL of anhydrous THF was added 63 mL of sodium bis(trimethylsilyl)amide (1M solution in THF, 63 mmol) dropwise at rt under argon protection. After the mixture was stirred at rt for half an hour, di-tert-butyl dicarbonate (7.2 g, 33 mmol) was added in one batch. The reaction was quenched 2 hours later, with the addition of water (30 mL) and 1N aqueous HCl (45 mL). The aqueous phase was separated and extracted with EtOAc. The combined organic phase was washed with saturated NaCl, dried over $Na_2SO_4$ and concentrated. The residue was purified by silica gel chromatography to give quinolin-3-yl-carbamic acid tert-butyl ester XXII (6.1 g, 83.5%).

To a solution of XXII (6.0 g, 24.56 mmol) in 150 mL of MeOH was added acetic acid (18 mL). The mixture was bubbled with argon for 15 min, then palladium hydroxide (20% palladium on carbon, 1.2 g) was added to the flask. The resulting suspension was subjected to hydrogenation under 45 psi for 16 h before filtered. The filtrate was concentrated and the residue was dissolved in $CH_2Cl_2$. The resulting $CH_2Cl_2$ solution was washed with saturated $NaHCO_3$, dried over $Na_2SO_4$ and concentrated. The residue was purified through silica gel to give (1,2,3,4-tetrahydro-quinoline-3-yl)-carbamic acid tert-butyl ester XXIII (4.2 g, 68%).

To a solution of XXIII (2.7 g, 10.9 mmol) in THF was added dropwise a solution of pyridinium tribromide (3.83, 0.41 mmol) in 50 mL of THF at rt. The reaction mixture was stirred for 15 min before 60 mL of water was added into the flask. The aqueous phase was extracted with EtOAc. The combined organic phase was washed with saturated NaCl, dried over $Na_2SO_4$ and concentrated. The residue was purified by flash silica gel chromatography to give (6-bromo-1,2,3,4-tetrahydro-quinoline-3-yl)-carbamic acid tert-butyl ester XXIV (2.5 g, 70%) as white solid.

To an argon sparkled solution of XXIV (1 g, 3.04 mmol), and zinc cyanide (352 mg, 3 mmol) in DMF (5 mL) was added tetrakis-(triphenylphosphine) palladium (0) (300 mg, 0.228 mmol) and the reaction mixture was then heated at 90° C. overnight. When the mixture was cooled down and partitioned between EtOAc and water, the aqueous phase was separated and extracted with EtOAc. The combined organic phase was washed with saturated NaCl, dried over $Na_2SO_4$ and concentrated. The residue was purified by silica gel column to give (6-cyano-1,2,3,4-tetrahydro-quinolin-3-yl)-carbamic acid tert-butyl ester XXV (560 mg, 67%) as white solid.

The mixture of XXV (560 mg, 2 mmol) in 10 mL of concentrated HCl was stirred at 80° C. in a sealed tube overnight. Then the reaction mixture was cooled to rt and evaporated to dryness under reduced pressure. The residue was dissolved in MeOH and the resulted solution was stirred at 60° C. for 2 h. The solvent was removed to give hydrochloride salt of 3-amino-1,2,3,4-tetrahydro-quinoline-6-carboxylic acid methyl ester XXVI in quantitative yield.

The mixture of XXVI (242 mg, 1 mmol), 2-chloro-4-pyridin-3-pyrimidine (191 mg, 1 mmol) and TEA (0.2 mL) in 3 mL of DMF was heated at 150° C. for 1 h in microwave reactor. The reaction mixture was diluted with EtOAc and washed with water. The combined organic phase was washed with saturated NaCl, dried over $Na_2SO_4$ and concentrated. The residue was purified through silica gel column to give intermediate 3-(4-pyridin-3-yl-pyrimidin-2-ylamino)-1,2,3,4-tetrahydro-quinoline-6-carboxylic acid methyl ester XXXX (172 mg, 48%) as white solid.

The mixture of XXXX (172 mg), 50% aqueous $NH_2OH$ (1 mL) and KOH (150 mg) in 1 mL of MeOH was stirred at rt for 1 h. The reaction solution was sent to preparative HPLC to give the title compound, EXAMPLE 53. MS: calc'd ($MH^+$) 363.1, exp ($MH^+$) 363.2. $^1H$ NMR (MeOD, 400 MHz), 9.44 (s, 1H), 8.95 (d, 1H, J=8.0 Hz), 8.50 (d, 1H, J=4.8 Hz), 8.48

(d, 1H, J=4.8 Hz), 7.92 (m, 1H), 7.42 (m, 1H), 6.59 (t, 3H, J=5.2 Hz), 4.61 (m, 1H), 3.60 (m, 1H), 3.30 (m, 1H), 3.18 (m, 1H), 2.98 (m, 1H).

Example 54

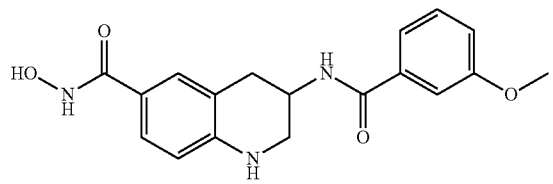 [SMILES: COc1cccc(C(=O)NC2CNc3ccc(C(=O)NO)cc3C2)c1]

3-(3-Methoxy-benzoylamino)-1,2,3,4-tetrahydro-quinoline-6-carboxylic acid hydroxyamide The title compound was prepared according to Scheme 8 by treating intermediate XXVI with appropriately substituted acyl chloride and conversion of ester functional group to hydroxamic acid. A detailed synthesis procedure is provided as Scheme 15.

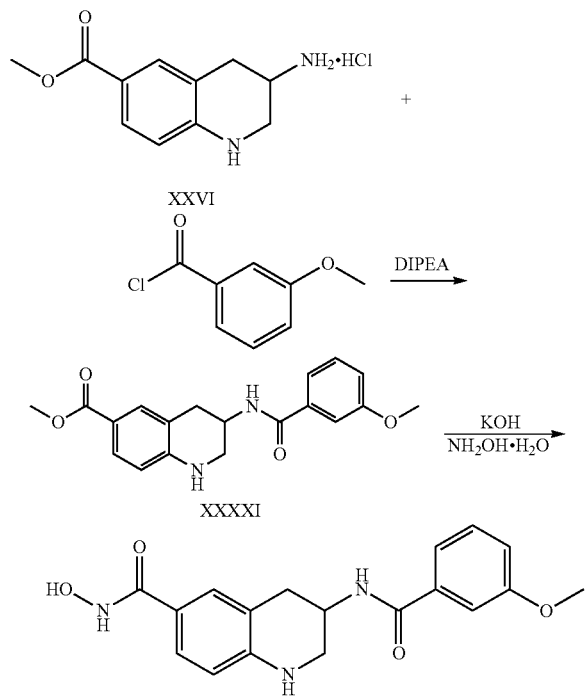

EXAMPLE 54

To a solution of XXVI (242 mg, 1 mmol) in CH$_2$Cl$_2$ (10 mL) was added 3-methoxy benzoyl chloride (170 mg, 1 mmol) and DIPEA (1 mmol), and the mixture was stirred at rt for 1 h. After solvent removal, the residue (crude product of XXXXI) was dissolved in 1 mL of MeOH. 1 mL of 50% aqueous NH$_2$OH and KOH (150 mg) was added to this solution, and the mixture was stirred at rt for 1 h. The reaction solution was sent to preparative HPLC to give the title compound, EXAMPLE 54. MS: calc'd (MH$^+$) 342.4, exp (MH$^+$) 342.4. $^1$H NMR (MeOD, 400 MHz), 7.37-7.4 (m, 5H), 7.09-7.12 (m, 1H), 6.55-6.57 (d, 1H, J=8.8 Hz), 4.39-4.42 (m, 1H), 3.85 (s, 3H), 3.52-3.53 (m, 1H), 3.25-3.28 (m, 1H), 3.05-3.06 (m, 1H), 2.96-2.98 (m, 1H).

Example 55

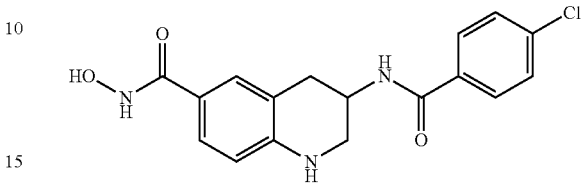

3-(4-Chloro-benzoylamino)-1,2,3,4-tetrahydro-quinoline-6-carboxylic acid hydroxyamide The title compound was prepared in analogy to EXAMPLE 54 as shown in Scheme 15, by using 4-chlorobenzoxyl chloride instead of 3-methoxy benzoxyl chloride. MS: calc'd (MH$^+$) 346.0, exp (MH$^+$) 346. $^1$H NMR (MeOD, 400 MHz), 7.78-7.82 (m, 2H), 7.46-7.50 (m, 2H), 7.39-7.41 (m, 2H), 6.56 (d, 1H, J=12 Hz), 4.40-4.42 (m, 1H), 3.40-3.56 (m, 1H), 3.25-3.30 (m, 1H), 3.14-3.15 (m, 1H), 2.96-2.98 (m, 1H).

Example 56

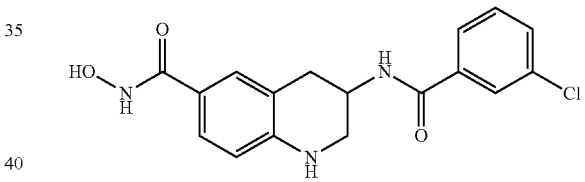

3-(3-Chloro-benzoylamino)-1,2,3,4-tetrahydro-quinoline-6-carboxylic acid hydroxyamide The title compound was prepared in analogy to EXAMPLE 54 as shown in Scheme 15, by using 3-chlorobenzoxyl chloride instead of 3-methoxy benzoxyl chloride. MS: calc'd (MH$^+$) 346, exp (MH$^+$) 346. $^1$H NMR (MeOD, 400 MHz), 7.83-7.84 (m, 1H), 7.73-7.75 (m, 1H), 7.55-7.57 (m, 1H), 7.44-7.48 (m, 1H), 7.39-7.41 (m, 2H), 6.57 (d, 1H, J=1.2 Hz), 4.39-4.41 (m, 1H), 3.51-3.56 (m, 1H), 3.25-3.28 (m, 1H), 3.05-3.07 (m, 1H), 2.97-3.05 (m, 1H).

Example 57

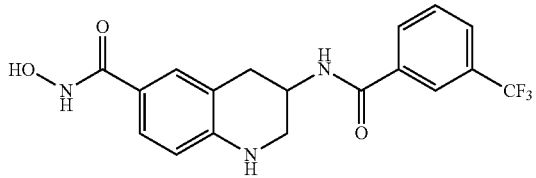 [SMILES: O=C(NO)c1ccc2c(c1)CC(NC(=O)c1cccc(C(F)(F)F)c1)CN2]

3-(3-Trifluoromethyl-benzoylamino)-1,2,3,4-tetrahydro-quinoline-6-carboxylic acid hydroxyamide The title compound was prepared in analogy to EXAMPLE 54 as shown in Scheme 15, by using 3-trifluofomethylbenzoxyl chloride instead of 3-methoxy benzoxyl chloride. MS: calc'd (MH+) 380.1, exp (MH+) 380.3. $^1$H NMR (MeOD, 400 MHz), 8.15 (s, 1H), 8.08 (d, 1H, J=8.0 Hz), 7.65 (d, 1H, 8.0 Hz), 7.68 (t, 1H, J=8.0 Hz), 7.40 (m, 2H), 6.58 (d, 1H, J=8.0 Hz), 4.46 (m, 1H), 3.56 (m, 1H), 3.33 (m, 1H), 3.12 (m, 1H), 2.98 (m, 1H).

Example 58

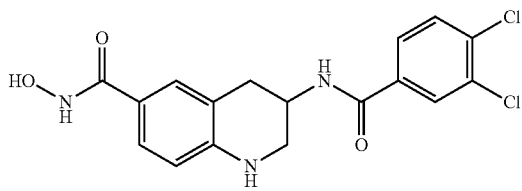 [SMILES: O=C(NO)c1ccc2c(c1)CC(NC(=O)c1ccc(Cl)c(Cl)c1)CN2]

3-(3,4-Dichloro-benzoylamino)-1,2,3,4-tetrahydroquinoline-6-carboxylic acid hydroxyamide The title compound was prepared in analogy to EXAMPLE 54 as shown in Scheme 15, by using 3,4-dichlorobenzoxyl chloride instead of 3-methoxy benzoxyl chloride. MS: calc'd (MH+) 380.1, exp (MH+) 380.1. $^1$H NMR (MeOD, 400 MHz), 7.99 (d, 1H, J=2.0 Hz), 7.74 (m, 1H), 7.64 (d, 1H, J=8.4 Hz), 7.40 (m, 2H), 6.57 (d, 1H, J=8.6 Hz), 4.40 (m, 1H), 3.55 (m, 1H), 3.30 (m, 1H), 3.25-2.90 (m, 2H).

Example 59

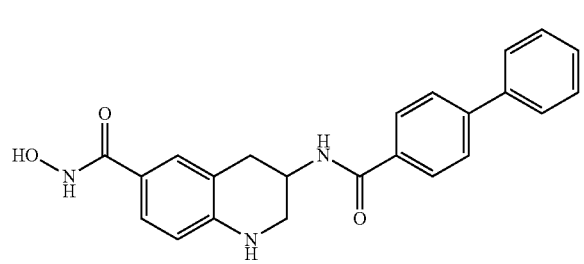 [SMILES: O=C(NO)c1ccc2c(c1)CC(NC(=O)c1ccc(-c3ccccc3)cc1)CN2]

3-[(Biphenyl-4-carbonyl)-amino]-1,2,3,4-tetrahydroquinoline-6-carboxylic acid hydroxyamide The title compound was prepared in analogy to EXAMPLE 54 as shown in Scheme 15, by using biphenyl-4-carbonyl chloride instead of 3-methoxy benzoxyl chloride. MS: calc'd (MH+) 388.4, exp (MH$^1$) 388.2. $^1$H NMR (MeOD, 400 MHz), 7.90 (d, 2H, J=8.4 Hz), 7.74-7.67 (m, 4H), 7.50-7.38 (m, 5H), 6.59 (d, 1H, 8.4 Hz), 4.45 (m, 1H), 3.58 (m, 1H), 3.30 (m, 1H), 3.13-2.94 (m, 2H).

Example 60

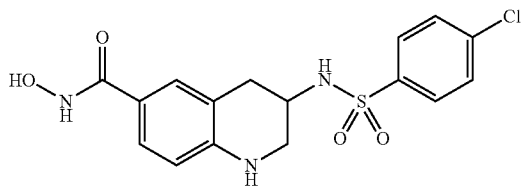 [SMILES: O=C(NO)c1ccc2c(c1)CC(NS(=O)(=O)c1ccc(Cl)cc1)CN2]

3-(4-Chloro-benzenesulfonylamino)-1,2,3,4-tetrahydro-quinoline-6-carboxylic acid hydroxyamide The title compound was prepared according to Scheme 8 by treating intermediate XXVI with appropriately substituted sulfonyl chloride and conversion of ester functional group to hydroxamic acid. A detailed synthesis procedure is provided as Scheme 16.

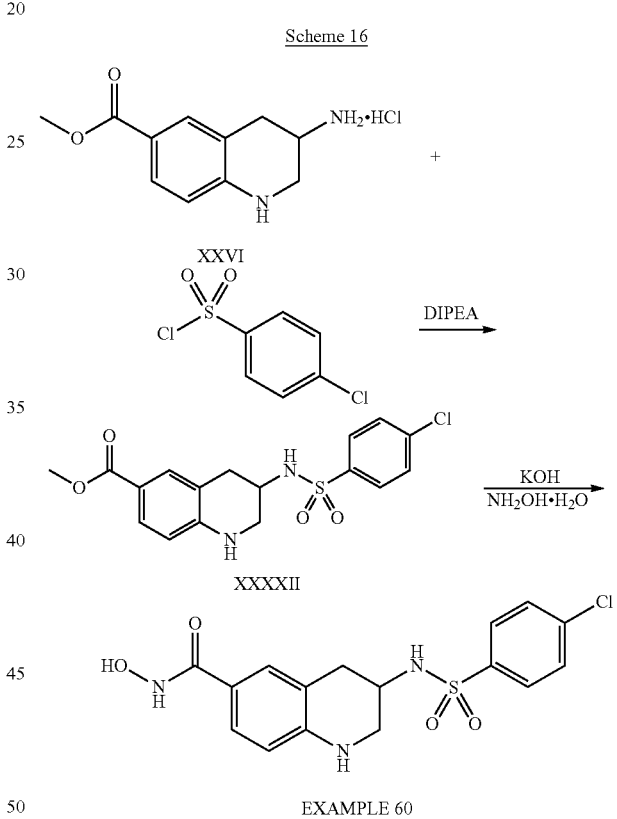

To a solution of XXVI (242 mg, 1 mmol) in 10 mL of CH$_2$Cl$_2$ was added 4-chloro-benzensulfonyl chloride (211 mg, 1 mmol) and DIPEA (1 mmol). After stirred at rt for 1 h, the reaction mixture was worked up with CH$_2$Cl$_2$ and aqueous HCl (1N). The organic phase was washed with brine, dried over Na$_2$SO$_4$ and concentrated to give sulfonamide XXXXII. 1 mL of 50% aqueous NH$_2$OH and KOH (150 mg) was added to a solution of XXXXII in 1 mL of MeOH, and the mixture was stirred at rt for 1 h. After that, the reaction solution was sent to preparative HPLC to give the title compound, EXAMPLE 60. MS: calc'd (MH+) 382.0, exp (MH+) 382.1. $^1$H NMR (MeOD, 400 MHz), 7.87-7.89 (m, 2H), 7.59-7.62 (m, 2H), 7.35-7.37 (dd, 1H, J$_1$=8.4 Hz, J$_2$=2 Hz), 7.23 (d, 1H, J=2 Hz), 6.48 (d, 1H, J=8.8 Hz), 3.62-3.65 (m, 1H), 3.50-3.61 (m, 1H), 3.04-3.09 (m, 1H), 2.82-2.84 (m, 1H), 2.78-2.84 (m, 1H).

Example 61

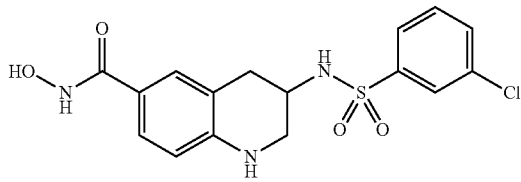 [SMILES: O=C(NO)c1ccc2c(c1)CC(NS(=O)(=O)c1cccc(Cl)c1)CN2]

3-(3-Chloro-benzenesulfonylamino)-1,2,3,4-tetrahydro-quinoline-6-carboxylic acid hydroxyamide The title compound was prepared in analogy to EXAMPLE 60 as shown in Scheme 16, by using 3-chloro-benzenesulfonyl chloride instead of 4-chloro-benzenesulfonyl chloride. MS: calc'd (MH$^+$) 382.0, exp (MH$^+$) 382.1. $^1$H NMR (MeOD, 400 MHz), 7.90 (m, 1H), 7.84-7.82 (m, 1H), 7.67-7.55 (m, 2H), 7.37 (m, 1H), 7.21 (d, 1H, J=1.6 Hz), 6.49 (d, 1H, J=8.8 Hz), 3.67 (m, 1H), 3.30 (m, 1H), 3.09 (m, 1H), 2.83 (m, 1H), 2.66 (m, 1H).

Example 62

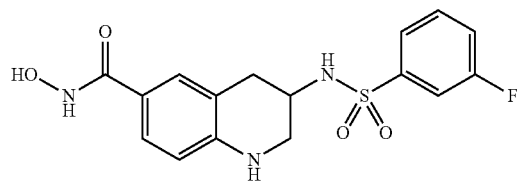 [SMILES: O=C(NO)c1ccc2c(c1)CC(NS(=O)(=O)c1cccc(F)c1)CN2]

3-(3-Fluoro-benzenesulfonylamino)-1,2,3,4-tetrahydro-quinoline-6-carboxylic acid hydroxyamide The title compound was prepared in analogy to EXAMPLE 60 as shown in Scheme 16, by using 3-fluoro-benzenesulfonyl chloride instead of 4-chloro-benzenesulfonyl chloride. MS: calc'd (MH$^+$) 366.4, exp (MH$^+$) 366.1. $^1$H NMR (MeOD, 400 MHz), 7.43 (d, 1H, J=8.0 Hz), 7.62 (m, 2H), 7.40 (m, 2H), 7.22 (s, 1H), 6.49 (d, 1H, J=8.8 Hz), 3.66 (m, 1H), 3.34-3.30 (m, 1H), 3.08 (m, 1H), 2.79 (m, 1H), 2.65 (m, 1H).

Example 63

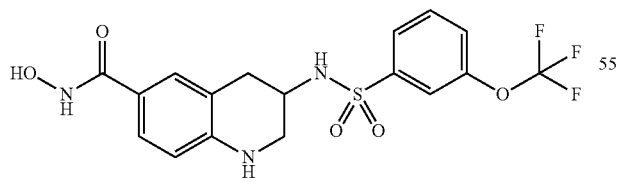

3-(3-Trifluoromethoxy-benzenesulfonylamino)-1,2,3,4-tetrahydro-quinoline-6-carboxylic acid hydroxyamide The title compound was prepared in analogy to EXAMPLE 60 as shown in Scheme 16, by using 3-trifluoromethoxy-benzensulfonyl chloride instead of 4-chloro-benzensulfonyl chloride. MS: calc'd (MH$^+$) 432.4, exp (MH$^+$) 432.1. $^1$H NMR (MeOD, 400 MHz), 7.92 (d, 1H, J=8.0 Hz), 7.81 (s, 1H), 7.72 (t, 1H, J=8.0 Hz), 7.58 (d, 1H, J=8.0 Hz), 7.36 (m, 1H), 7.23 (s, 1H), 6.51 (d, 1H, J=8.8 Hz), 3.67 (m, 1H), 3.33-3.30 (m, 1H), 3.10 (m, 1H), 2.80 (m, 1H), 2.67 (m, 1H).

Example 64

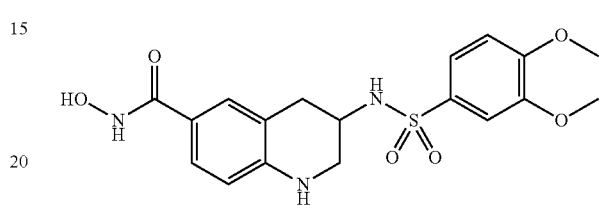

3-(3,4-Dimethoxy-benzenesulfonylamino)-1,2,3,4-tetrahydro-quinoline-6-carboxylic acid hydroxyamide The title compound was prepared in analogy to EXAMPLE 60 as shown in Scheme 16, by using 3,4-dimethoxy-benzenesulfonyl chloride instead of 4-chloro-benzensulfonyl chloride. MS: calc'd (MH$^+$) 408.4 exp (MH$^+$) 408.3. $^1$H NMR (MeOD, 400 MHz), 7.52 (m, 1H), 7.40 (d, 1H, J=2.4), 7.36 (m, 1H), 7.20 (s, 1H), 7.10 (d, 1H, J=8.8 Hz), 6.48 (d, 1H, 8.8 Hz), 3.93 (s, 3H), 3.87 (s, 3H), 3.60 (m, 1H), 3.29 (m, 1H), 3.08 (m, 1H), 2.76 (m, 1H), 2.63 (m, 1H).

Example 65

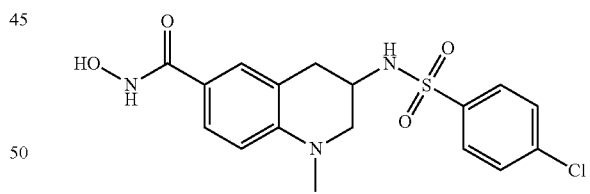

3-(4-Chloro-benzenesulfonylamino)-1-methyl-1,2,3,4-tetrahydro-quinoline-6-carboxylic acid hydroxyamide The title compound was prepared according to Scheme 8, by treating XXXXII with paraformaldehyde and sodium cyanoborohydride in acetic acid to give N-methylated intermediate, and following treatment of ester with 50% aqueous NH$_2$OH and KOH in MeOH. MS: calc'd 396 (MH$^+$), exp 396 (MH$^+$). $^1$H NMR (MeOD, 400 MHz), 7.88 (d, 2H, J=1.6 Hz), 7.60-7.63 (m, 2H), 7.28-7.51 (dd, 1H, J$_1$=8.8 Hz, J$_2$=2 Hz), 7.25-7.26 (m, 1H), 6.60-6.62 (d, 1H, J=8.8 Hz), 3.73-3.75 (m, 1H), 3.37-3.38 (m, 1H), 3.12-3.14 (m, 1H), 3.87 (s, 3H), 2.84-2.87 (m, 1H), 2.67-2.69 (m, 1H).

Example 66

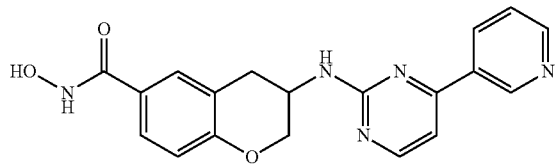 [SMILES: O=C(NO)c1ccc2c(c1)CC(Nc1nccc(-c3cccnc3)n1)CO2]

3-(5-Pyridin-3-yl-pyrimidin-2-ylamino)-chroman-6-carboxylic acid hydroxyamide

The title compound was prepared according to Scheme 9 by treating intermediate XXXIV with 2-chloro-5-pyridin-3-yl-pyrimidine and conversion of ester functional group to hydroxamic acid. A detailed synthesis procedure is provided as Scheme 17.

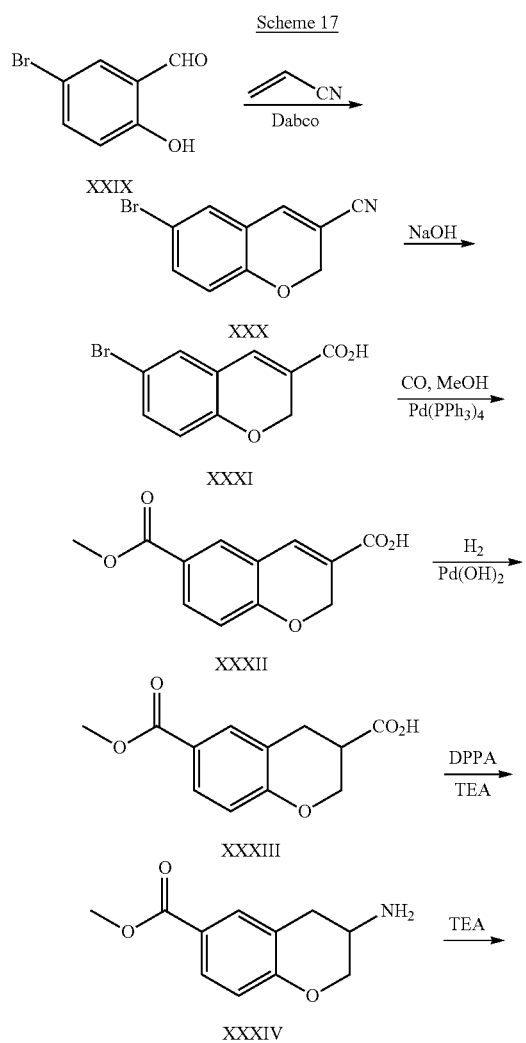

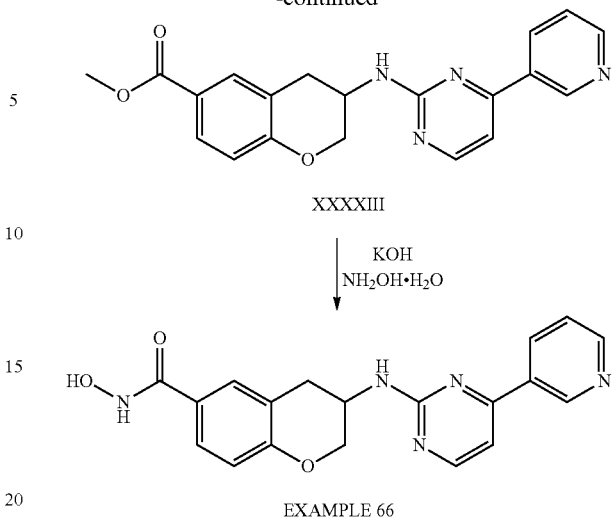

A mixture of 2-hydroxy-5-bromobenzaldehyde XXIX (30 g, 0.15 mol), acrylonitrile (50 g, 0.75 mol), and 1,4-diazabicyclo[2.2.2]octane (Dabco, 4 g, 0.035 mol) was refluxed overnight. The reaction mixture was diluted with ethyl ether and washed with NaOH (1N), water, HCl (1N) and brine. The organic phase was dried over anhydrous $Na_2SO_4$, and concentrated in vacuo to give 25 g of 6-bromo-2H-chromene-3-carbonitrile XXX (Yield 70%). MS: calc'd 237 ($MH^+$), exp 237 ($MH^+$).

A mixture of XXX (25 g, 0.1 mol) and 300 mL of 10% NaOH was refluxed for 6 h. The mixture was acidified with concentrated HCl. The precipitate was collected and dried to yield 15 g of 6-bromo-2H-chromene-3-carboxylic acid XXXI (Yield 59%). MS: calc'd 256 ($MH^+$), exp 256 ($MH^+$).

A mixture of XXXI (2 g, 7.84 mmol), Pd $(PPh_3)_4$ (1.36 g, 1.18 mmol), $Et_3N$ (3.3 mL, 23.52 mmol), MeOH (30 mL) and DMF (10 mL) was heated at 80° C. for 12 h under carbon monoxide atmosphere. After solvent removal, the residue was extracted with EtOAc and the organic phase was washed with brine, dried over $Na_2SO_4$, filtered, and evaporated. After silica gel column purification, 1.2 g of 2H-chromene-3,6-dicarboxylic acid 6-methyl ester XXXII was obtained (Yield 66%). MS: calc'd 235 ($MH^+$), exp 235 ($MH^+$).

A mixture of ester XXXII (2 g, 8.5 mmol) and 300 mg of Pd $(OH)_2$ in 20 mL of MeOH was stirred in an autoclave at 80° C. for 48 h under 40 psi of $H_2$. Then the reaction mixture was filtered, and concentrated to give 1.7 g of chroman-3,6-dicarboxylic acid 6-methyl ester XXXIII (Yield 85%). MS: calc'd 237 ($MH^+$), exp 237 ($MH^+$).

To a solution of XXXIII (1 g, 4.2 mmol) and TEA (1 mL) in 10 mL of tert-butylalcohol was added 1.15 g of diphenyl phosphoryl azide (4.2 mol). The reaction mixture was stirred at 80° C. for 12 h before concentrated in vacuo. The residue was dissolved in 20 mL of HCl/MeOH (1 N) and the mixture was stirred for at rt for 2 h. After solvent removal, the residue was partitioned between water and EtOAc. The aqueous layer was neutralized to pH 8 by addition of $Na_2CO_3$, and extracted with EtOAc. The organic phase was dried over $Na_2SO_4$ and concentrated to give 0.25 g of 3-amino-chroman-6-carboxylic acid methyl ester XXXIV (Yield 29%). MS: calc'd 208 ($MH^+$), exp 208 ($MH^+$).

A mixture of XXXIV (100 mg, 0.48 mmol), 2-chloro-5-pyridin-3-yl-pyrimidine (96 mg, 0.5 mmol) and TEA (137 μl, 1 mmol) in 2 mL of DMF was stirred at 150° C. for 1 h in a microwave reactor. The mixture was worked up with brine and EtOAc, and the organic phase was dried over Na$_2$SO$_4$, filtered, and evaporated in vacuo. Purification by silica gel column gave 80 mg of 3-(5-pyridin-3-yl-pyrimidin-2-ylamino)-chroman-6-carboxylic acid methyl ester XXXXIII (Yield 44%). MS: calc'd 363 (MH$^+$), exp 363 (MH$^+$).

To a solution of XXXXIII (80 mg, 0.22 mmol) in MeOH (1 mL) was added 0.5 mL of NH$_2$OH (50 wt. % solution in water) and KOH (86 mg, 1.54 mmol). After stirred at rt for 1 h, the reaction mixture was sent to purification by preparative HPLC and 30 mg of title compound was obtained (Yield 38%). EXAMPLE 66: MS: calc'd 364 (MH$^+$), exp 364 (MH$^+$) $^1$H NMR (DMSO, 400 MHz), 8.78 (d, 2H), 8.56-8.58 (m, 1H), 8.00-8.02 (d, 1H, J=8.0 Hz), 7.95-7.97 (d, 2H, J=8.0 Hz), 7.51-7.55 (d, 1H, J=16 Hz), 7.41-7.43 (d, 2H, J=8.0 Hz), 7.10-7.14 (m, 1H), 6.81-6.85 (d, 1H, J=16 Hz), 6.53-6.56 (dd, 1H, J1=11.2 Hz, J2=2.8 Hz), 6.35-6.37 (m, 1H), 5.22 (s, 2H), 4.49 (s, 2H).

Example 67

Biological Activities

The compounds of the present invention demonstrated sub-micromolar to micromolar inhibition of HDAC6 or HDAC8 based on their in-cell tubulin acetylation activity and enzymatic inhibition of HDAC8. Compounds from the present invention are able to induce obvious NB cell differentiation. Compounds from the present invention also demonstrate synergy when combined with bortezomib in cell growth inhibition of MM cell lines.

HDAC8 Inhibition by Novel Compounds: Recombinant HDAC8 Fluorometric Assay

A competitive inhibitory assay of HDAC8 was carried out by using recombinant HDAC8 and a commercial substrate Ac-Arg-His-Lys-Lys(ε-acetyl)-AMC. Examples in Table 1 of this invention demonstrated HDAC8 inhibitory activities with IC$_{50}$ values in the range of 0.2 μM to 3 μM as shown in Table 1.

Compounds were tested for their ability to inhibit histone deacetylase 8 using an in vitro deacetylation assay. The enzyme source for this assay was recombinant human HDAC8 protein expressed and purified from insect cells. The HDAC8 enzyme activity was validated by comparing with commercial HDAC8 (Cayman Chemical). The substrate consisted of a commercial product Ac-Arg-His-Lys-Lys(ε-acetyl)-AMC (substrate is available from Cayman Chemical). Using the substrate concentration at the K$_m$ for the HDAC8 enzyme, the deacetylation assay was performed in the presence of novel compounds from 0.01-30 μM using half-log dilutions. In a detailed procedure, 8 μl of HDAC8 enzyme solution (0.125 μg/μl) was transferred to assay plates (CORNING 3676). 1 μl of half-log diluted compounds were added into wells and incubated for 15 min at rt. After that, 8 μl of substrate solution was transferred to the wells and incubated for 30 min at rt. After deacetylation of the substrate by incubation with HDAC8 enzyme, subsequent exposure to a developing reagent produced a fluorophore that was directly proportional to the level of deacetylation. So 4 μl of developer regent (Cayman 10006394) was added into the wells in the assay plates and incubated for 15 min. The fluorescence signal was measured by a FlexStation3 plate reader (excitation wave length 340-360 nm; emission wave length 440-465 nm). The IC$_{50}$ was calculated after normalization and curve fitting using XLfit4.0 software. Inhibition %=[Mean(top)−signal (sample)]*100/[Mean(top)−Mean(bottom)].

TABLE 1

HDAC8 inhibition by novel compounds: recombinant HDAC8 fluorometric assay

| Example # | HDAC8 IC$_{50}$ (μM) |
|---|---|
| 1 | 2.68 |
| 2 | 0.68 |
| 3 | 3.74 |
| 4 | 3.73 |
| 5 | 2.90 |
| 6 | 0.93 |
| 7 | 0.73 |
| 8 | 0.30 |
| 9 | 0.29 |
| 10 | 2.13 |
| 11 | 0.80 |
| 12 | 0.26 |
| 13 | 2.20 |
| 14 | 1.66 |
| 15 | 0.30 |
| 16 | 0.80 |
| 17 | 1.10 |
| 18 | 1.23 |
| 19 | 1.69 |
| 20 | 1.52 |
| 21 | 2.15 |
| 22 | 2.24 |
| 23 | 1.44 |
| 24 | 0.72 |
| 25 | 0.48 |
| 26 | 0.52 |
| 27 | 0.52 |
| 28 | 1.00 |
| 29 | 0.90 |
| 30 | 0.51 |
| 31 | 0.32 |
| 32 | 1.50 |
| 33 | 3.78 |
| 34 | 0.48 |
| 35 | 1.78 |
| 36 | 3.04 |
| 37 | 0.99 |
| 38 | 1.27 |
| 39 | 0.91 |
| 40 | 0.35 |
| 41 | 0.85 |
| 42 | 0.16 |
| 43 | 0.37 |
| 44 | 0.21 |
| 45 | 0.39 |
| 46 | 0.19 |
| 47 | 0.47 |
| 48 | 0.37 |
| 50 | 1.51 |
| 51 | 1.28 |
| 52 | 0.93 |
| 53 | 0.47 |
| 54 | 2.81 |
| 55 | 2.41 |
| 56 | 3.37 |
| 57 | 2.67 |
| 58 | 2.63 |
| 59 | 2.85 |
| 60 | 1.46 |
| 61 | 0.97 |
| 62 | 1.14 |
| 63 | 1.61 |
| 64 | 1.22 |
| 65 | 0.75 |
| 66 | 0.83 |

Tubulin Acetylation Induction by Novel Compounds: Tubulin Acetylation Cytoblot Assay Tubulin acetylation is a PD marker for HDAC6 inhibition. The extent of tubulin acetylation represents the inhibitory effect on HDAC6. Examples in Table 2 of this invention demonstrated tubulin acetylation activities with EC$_{50}$ values in the range of 0.1 μM to 10 μM as shown in Table 2.

Novel compounds were tested for their ability to inhibit HDAC6 using a cell-based deacetylation assay. Tubulin acetylation was detected by the anti-acetylated tubulin antibody (Sigma) and horse radish peroxidase (HRP) conjugated secondary antibody (KangChen Bio. Tech.). A549 cells were seeded into assay plates (CORNING 3912) at concentration of 1×10$^5$ cells/mL and incubated for 16-18 h at 37° C. with the presence of 5% $CO_2$. 20 µl of diluted compound solution was transferred to the cell culture plate and incubated for 17-18 h. After medium removal and fixation by formaldehyde (3.7% paraformaldehyde in TBS), the cells in the plates were treated with 180 µl of −20° C. MeOH and incubated for 5 min at rt. The cell lysis was incubated with 75 µl of primary anti-acetylated tubulin antibody and secondary HRP conjugated antibody solution (1:750 anti-acetylated tubulin, 1:750 HRP conjugated anti-mouse IgG in antibody dilution buffer not containing sodium azide) for 4 h at 4° C. By adding the HRP substrate, enhanced chemiluminescence (ECL) reagent (GE Healthcare) generated luminescence corresponding to the level of tubulin acetylation. So that 75 µl of ECL was added into the wells and the luminescence from each well was immediately quantified by the plate reader. Based on the luminescence reading, the $IC_{50}$s against HDAC6 of the tested compounds were calculated by plotting the curve with XLfit4.0 software. Inhibition %=[signal(sample)−Mean(bottom)]*100/[Mean(top)−Mean(bottom)]

TABLE 2

Tubulin acetylation induction by novel compounds: tubulin acetylation cytoblot assay

| Example # | Tub-ac $EC_{50}$ (µM) |
|---|---|
| 1 | 12.45 |
| 2 | 5.47 |
| 3 | 1.86 |
| 4 | 0.46 |
| 5 | 5.00 |
| 6 | 2.07 |
| 7 | 0.73 |
| 8 | 0.83 |
| 9 | 1.68 |
| 10 | 1.31 |
| 11 | 5.10 |
| 12 | 0.97 |
| 13 | 8.70 |
| 14 | 4.95 |
| 15 | 0.93 |
| 16 | 3.46 |
| 17 | 2.30 |
| 18 | 1.37 |
| 19 | 5.00 |
| 20 | 6.20 |
| 21 | 9.53 |
| 22 | 6.00 |
| 24 | 1.18 |
| 25 | 6.20 |
| 26 | 1.52 |
| 27 | 1.90 |
| 28 | 5.47 |
| 29 | 1.43 |
| 30 | 0.60 |
| 31 | 6.70 |
| 32 | 5.20 |
| 34 | 7.86 |
| 35 | 0.93 |
| 36 | 2.25 |
| 38 | 0.93 |
| 39 | 4.20 |
| 40 | 0.99 |
| 41 | 1.07 |
| 42 | 1.72 |
| 43 | 3.85 |

TABLE 2-continued

Tubulin acetylation induction by novel compounds: tubulin acetylation cytoblot assay

| Example # | Tub-ac $EC_{50}$ (µM) |
|---|---|
| 44 | 3.90 |
| 45 | 3.43 |
| 46 | 4.86 |
| 47 | 3.42 |
| 48 | 6.20 |
| 49 | 4.30 |
| 50 | 6.43 |
| 51 | 5.20 |
| 52 | 3.74 |
| 53 | 11.82 |
| 54 | 3.39 |
| 55 | 2.69 |
| 56 | 3.43 |
| 57 | 7.13 |
| 58 | 5.36 |
| 59 | 7.99 |
| 65 | 10.58 | p21 Reporter Gene Induction by Novel Compounds

As a surrogate for in-cell HDAC1/2/3 inhibition, p21 induction was used as a counterscreen to evaluate the selectivity of the compounds in the present invention toward HDAC6 or HDAC8. In contrast to positive controls MS275 and SAHA, none of the compounds of the present invention showed comparable p21 induction activity at 3 µM, 10 µM, and 30 µM concentrations.

The novel compounds of the present invention were tested for their ability to induce p21 gene expression using a reporter gene assay involving HeLa cells transfected with a p21 promoter-luciferase construct. The p21 promoter contained the Sp1/Sp3 binding site for HDAC but not the upstream p53 binding site. Briefly, the day before transfection, HeLa cells were seeded at 11,000 cells/well in a 96-well culture plate and incubated at 37° C. in 5% $CO_2$ overnight. A transfection media was prepared prior to transfection according to the following procedure: (1) 5 µl serum-free DMEM, 0.15 µl Fugene 6 reagent, 40 ng p21-luc, 10 ng GFP were mixed gently and incubated at rt for 30 minutes; (2), then 98 µl DMEM (with 10% FBS, 1% penicillin and streptomycin) was added to the DNA: Fugene 6 reagent complex and mixed gently. For transfection, the medium was removed and replaced with 100 µl/well transfection media which was prepared according to the procedure above. After incubating the cells for 24 hours at 37° C. in 5% $CO_2$, fresh media and test compounds were added to the wells and the cells further incubated for 15 hours at 37° C. in 5% $CO_2$. Cells were lysed by adding 80 µl/well of a cell culture lysis reagent (Promega). 50 µl of each lysate was taken for GFP detection using an excitation wavelength of 486 nm and detection at 527 nm. 100 µl luciferase assay reagent (Promega) was then added to every 20 µl cell lysate for luminometer detection. The compounds of this invention described in the Examples and Tables above exhibit weak p21 induction activity in the range of about 0% to 50% relative to the known HDAC inhibitor (MS-275) at 1 µM, 3 µM, and 10 µM concentrations. Induction activity for specific representative compounds can be found in Table 3.

TABLE 3 p21 reporter gene induction by novel compounds in relative potency to MS-275

| Example # | p21 RP3 * | p21 RP10 * | p21 RP30 * |
|---|---|---|---|
| 1 | −0.07 | −0.01 | −0.01 |
| 2 | 0.26 | −0.06 | −0.04 |
| 3 | 0.08 | −0.08 | −0.06 |
| 4 | −0.02 | −0.08 | −0.06 |
| 5 | −0.09 | −0.01 | 0.00 |
| 6 | 0.18 | 0.03 | −0.01 |
| 7 |  | −0.01 | −0.05 |
| 8 | −0.12 | −0.06 | −0.19 |
| 9 | −0.21 | −0.03 | −0.10 |
| 10 | −0.58 | −0.08 |  |
| 11 | −0.13 | −0.18 | −0.18 |
| 12 | 0.10 | 0.00 | −0.10 |
| 13 | −0.22 | −0.20 | −0.23 |
| 14 | −0.68 | −0.59 | −0.49 |
| 15 | 0.30 | 0.00 | 0.00 |
| 16 | 1.50 | 0.40 | 0.30 |
| 17 | −0.56 | −0.47 | −0.45 |
| 18 | 0.43 | 0.06 | −0.06 |
| 19 | −0.18 | −0.26 | −0.29 |
| 20 | −0.71 | −0.44 | −0.40 |
| 21 | −0.24 | −0.28 | −0.32 |
| 22 | −0.87 | −0.59 | −0.52 |
| 23 | 0.30 | 0.00 | −0.10 |
| 24 | −0.33 | −0.02 |  |
| 25 | 0.30 | 0.13 | 0.08 |
| 26 | 0.68 | 0.20 | −0.05 |
| 27 | 0.35 | 0.05 | −0.09 |
| 28 | −0.20 | −0.19 | −0.24 |
| 29 | 0.39 | 0.07 | −0.02 |
| 30 | 0.40 | 0.10 | −0.03 |
| 31 | 0.18 | 0.19 | 0.12 |
| 32 | 0.26 | 0.15 | −0.04 |
| 33 | 0.19 | −0.20 | −0.25 |
| 34 | 0.42 | 0.31 | −0.02 |
| 35 | −0.86 | −0.30 |  |
| 36 | −0.38 | −0.10 |  |
| 37 | −0.18 | −0.05 |  |
| 38 | 0.15 | 0.05 | 0.02 |
| 39 | 0.08 | 0.03 | 0.04 |
| 40 | 0.18 | 0.26 | 0.38 |
| 41 | −0.15 | 0.35 | 0.05 |
| 42 | 0.52 | 0.31 | 0.01 |
| 43 | 0.13 | 0.08 | −0.04 |
| 44 | 0.63 | 0.32 | 0.56 |
| 45 | 0.18 | 0.18 | 0.46 |
| 46 | 0.49 | 0.15 | 0.01 |
| 47 | 0.08 | 0.01 | −0.04 |
| 48 | 0.41 | 0.17 | 0.17 |
| 49 | 0.50 | 0.08 | 0.00 |
| 50 | 0.26 | 0.03 | −0.01 |
| 51 | 0.20 | 0.03 | 0.00 |
| 52 | 0.12 | 0.01 | −0.02 |
| 53 | 0.18 | 0.03 | 0.02 |
| 54 | 0.03 | 0.03 | 0.07 |
| 55 | 0.50 | 0.13 | 0.06 |
| 56 | 0.04 | 0.05 | 0.12 |
| 57 | 0.07 | 0.01 | 0.04 |
| 58 | 0.03 | −0.03 | 0.01 |
| 59 | 0.20 | 0.08 | 0.15 |
| 60 | 0.46 | 0.10 | 0.04 |
| 61 | 0.21 | 0.07 | 0.04 |
| 62 | 0.13 | 0.02 | 0.01 |
| 63 | 0.11 | 0.04 | 0.01 |
| 64 | −0.02 | 0.06 | 0.04 |
| 65 | 0.41 | 0.26 | 0.46 |
| 66 | −0.02 | −0.03 | 0.02 |

* Note:
p21 RP3 represents the relative gene level of p21 induced by individual example compared to MS275 at 3 μM concentrations;
p21 RP10 represents the relative level of p21 induced by individual example compared to MS275 at 10 μM concentrations;
p21 RP30 represents the relative level of p21 induced by individual example compared to MS275 at 30 μM concentrations.

Differentiation Morphology Evaluation Assay

Novel compounds were tested for their ability to induce neuroblastoma cell differentiation. The BE(2)-C neuroblastoma cells were seeded in 6 cm culture plate at 20000 cells/ml and incubated at 37° C. in 5% $CO_2$ overnight. Different concentrations of compounds were added into the plate and 13-cis-retinoic acid (13-cRA) was used as positive control. The cells were cultured for another 6 d. Media was replaced every other day along with the addition of fresh compound. On day 3 and day 6, cell morphology was observed by microscope. The neurite extensions were counted evaluated with a score 0-5. Score 0 was assigned to DMSO negative control, and 13-cis-retinoic acid positive control was considered as score 5.

WST Anti-Proliferative Assay and Assessment of Growth Inhibitory Synergy Between Novel Compounds and Bortezomib (Velcade) in Multiple Myeloma Cell Lines The novel compounds of the present invention were tested for their ability to inhibit growth of multiple myeloma cell lines using in vitro growth inhibition assays described below.

Cells were seeded in 96-well culture plates (200 μl/well at different seeding concentrations depending on cell type) and incubated overnight at 37° C. in 5% $CO_2$. After adding compound dilutions to the cells (DMSO concentration kept below 0.5%), the cells were incubated at 37° C. in 5% $CO_2$ for 72 hours. The effects on proliferation were determined by addition of CCK-8 reagent (Dojindo) according to the manufacturer's instruction, followed by incubation for 2 hours at 37° C. in 5% $CO_2$, and finally recording the absorbance at 450 nm using an ELISA plate reader.

Novel compounds were tested for their synergistic effect with Velcade in multiple myeloma cells in vitro. Briefly, the multiple myeloma cells (RPMI-8226, OPM-2, or NCI-H929) were seeded into 96 well plate at 18000-20000 cells per well. The GI50s of these compounds against myeloma cells were measured by WST assay. Based on GI50 data, a suitable series of compound dilution were determined to inhibit the cell viability from 20% to 70%. The tested compound and Velcade used the same dilution factor in the combination treatment. Similar to the WST assay, both velcade and tested compound were added into the cells at a series of dilution concentrations. After 72 h treatment, cell viability was measured at 450 nm by SpectraMAX190 after 2 h incubation with CCK8 reagent at 37° C. Synergy between the tested compounds and velcade was analyzed by software Calcusyn. A combination index below 1 indicates synergy between the novel compound and Velcade which is further illustrated by the notes below.

$$CI = \frac{(D)_1}{(D_x)_1} + \frac{(D)_2}{(D_x)_2} + \frac{(D)_1(D)_2}{(D_x)_1(D_x)_2}$$

Notes: Chou and Talalay in 1983 proposed the designation of CI (combination index)=1 as the additive effect. CI<1, =1, and >1 indicates synergism, additive effect, and antagonism, respectively (Chou, T.-C., and Talalay, P. *Trends Pharmacol. Sci.* 1983, 4:450-454). It can be calculated by the equation above. This equation dictates that drug 1, $(D)1$, and drug 2, $(D)2$, (in the numerators) in combination inhibit x % in the actual experiment. Thus, the experimentally observed x % inhibition may not be a round number but most frequently has a decimal fraction. $(Dx)1$ and $(Dx)2$ (in the denominators) of this equation are the doses of drug 1 and drug 2 inhibit x % alone, respectively.

Figure 2:
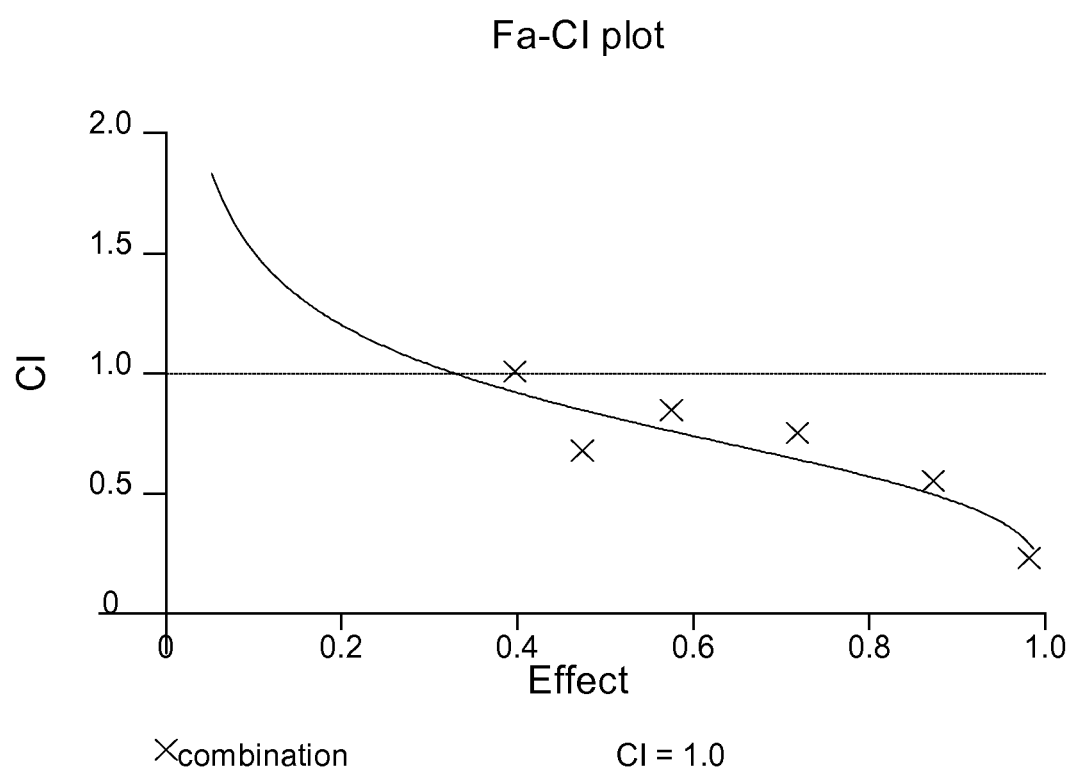
FIG. 2. The combination index (CI) of EXAMPLE 24 with Velcade in the Fa-CI plot is below 1 at both $EC_{50}$ and $EC_{90}$ concentrations.

The synergistic effects are shown in FIG. 1 and FIG. 2.

It has been found that the compounds of the present invention are HDAC6 or HDAC8 inhibitors which have anti-proliferative and differentiation-inducing activity, which results in inhibition of tumor cell proliferation and induction of apoptosis. These compounds are therefore useful for the treatment of diseases such as neuroblastoma and multiple myeloma in humans or animals.

Example A

Tablet Formulation

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
| Total | 425 mg |

Example B

Capsule Formulation

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
| Total | 220.0 mg |

The invention claimed is:

1. A compound of formula (I)

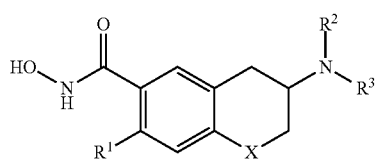

wherein
X is —$CH_2$—, oxygen or —$NR^4$;
$R^1$ is hydrogen or halogen;
$R^2$ is hydrogen; or
  alkyl, provided that X is —$CH_2$— or oxygen;
$R^3$ is phenyl, unsubstituted or once or twice substituted by halogen, nitro, alkyl, trifluoromethyl, dialkylamino, aminoalkyl, cyano or phenoxy;
  pyridin-2-yl, unsubstituted or once or twice substituted by nitro or trifluoromethyl;
  pyrimidin-2-yl, unsubstituted or once or twice substituted by alkyl, trifluoromethyl, alkoxy, phenoxy, pyridinyl, alkylpyridinyl, alkoxypyridinyl, halopyridinyl, morpholinylpyridinyl, naphthyl, quinolinyl, phenyl or substituted phenyl, wherein substituted phenyl is phenyl once or twice substituted by alkyl, halogen, dialkylamino, nitro, alkoxy, trifluoromethyl or phenoxy;
  quinazolin-2-yl, unsubstituted or once or twice substituted by halogen;
  phenylalkenylcarbonyl;
  phenylalkylcarbonyl;
  phenylalkoxycarbonyl;
  phenylcarbonyl, unsubstituted or once or twice substituted by halogen, alkyl, trifluoromethyl, alkoxy, trifluoromethoxy, cyano, dialkylamino or phenyl;
  pyridinylalkenylcarbonyl;
  pyridinylalkylcarbonyl;
  pyridinylalkoxycarbonyl;
  alkylsulfonyl;
  phenylsulfonyl, wherein phenyl is unsubstituted or once or twice substituted by halogen, trifluoromethyl, trifluoromethoxy, alkoxy, cyano, dialkylamino or dialkylaminoalkyl;
  or pyridinylsulfonyl;
$R^4$ is hydrogen or alkyl;
or a pharmaceutically acceptable salt, ester or stereoisomers thereof.

2. A compound according to claim 1, wherein
X is —$CH_2$—, oxygen or —$NR^4$;
$R^1$ is hydrogen or halogen;
$R^2$ is hydrogen; or
  alkyl, provided that X is —$CH_2$— or oxygen;
$R^3$ is phenyl, unsubstituted or once or twice substituted by halogen, nitro or cyano;
  pyridin-2-yl, unsubstituted or once substituted by nitro;
  pyrimidin-2-yl, unsubstituted or once or twice substituted by alkyl, trifluoromethyl, alkoxy, phenoxy, pyridinyl, alkylpyridinyl, alkoxypyridinyl, halopyridinyl, morpholinylpyridinyl, naphthyl, quinolinyl, phenyl or substituted phenyl, wherein substituted phenyl is phenyl once or twice substituted by alkyl, halogen, dialkylamino, alkoxy, trifluoromethyl or phenoxy;
  quinazolin-2-yl substituted by halogen;
  alkoxyphenylcarbonyl;
  halophenylcarbonyl;
  trifluoromethylphenylcarbonyl;
  phenylphenylcarbonyl;
  pyridinylalkenylcarbonyl;
  pyridinylalkoxycarbonyl;
  alkylsulfonyl;
  phenylsulfonyl, wherein phenyl is once or twice substituted by halogen, trifluoromethyl, trifluoromethoxy or alkoxy;
  or pyridinylsulfonyl;
$R^4$ is hydrogen or alkyl;
or a pharmaceutically acceptable salt, ester or stereoisomers thereof.

3. A compound according to claim 1, wherein $R^1$ is hydrogen or fluoro; and all remaining substituents have the significances given in claim 1.

4. A compound according to claim 1, wherein $R^2$ is hydrogen; or
methyl, provided that X is —$CH_2$— or oxygen;
and all remaining substituents have the significances given in claim 1.

5. A compound according to claim 1, wherein
$R^3$ is phenyl, unsubstituted or once or twice substituted by fluoro, chloro, bromo, nitro or cyano;
pyridin-2-yl, unsubstituted or once substituted by nitro;
pyrimidin-2-yl, unsubstituted or once or twice substituted by methyl, trifluoromethyl, ethoxy, phenoxy, pyridinyl, methylpyridinyl, methoxypyridinyl, chloropyridinyl, morpholinylpyridinyl, naphthyl, quinolinyl, phenyl or substituted phenyl wherein substituted phenyl is phenyl once or twice substituted by methyl, fluoro, chloro, dimethylamino, methoxy, trifluoromethyl or phenoxy;
fluoroquinazolin-2-yl;
pyridinylethylenylcarbonyl;
pyridinylmethoxycarbonyl;
methoxyphenylcarbonyl;
chlorophenylcarbonyl;
trifluoromethylphenylcarbonyl;
phenylphenylcarbonyl;
butylsulfonyl;
phenylsulfonyl, wherein phenyl is once or twice substituted by fluoro, chloro, trifluoromethyl, trifluoromethoxy or methoxy;
or pyridinylsulfonyl;
and all remaining substituents have the significances given in claim 1.

6. A compound according to claim 5, wherein
$R^3$ is phenyl, unsubstituted or once or twice substituted by bromo;
pyrimidin-2-yl, unsubstituted or once or twice substituted by methyl, trifluoromethyl, ethoxy, pyridinyl, methylpyridinyl, methoxypyridinyl, chloropyridinyl, morpholinylpyridinyl, quinolinyl, phenyl or substituted phenyl wherein substituted phenyl is phenyl once or twice substituted by methyl, fluoro, chloro, dimethylamino or methoxy;
fluoroquinazolin-2-yl;
pyridinylethoxycarbonyl;
methoxyphenylcarbonyl;
butylsulfonyl;
or phenylsulfonyl, wherein phenyl is once or twice substituted by fluoro, chloro, trifluoromethyl or methoxy;
and all remaining substituents have the significances given in claim 5.

7. A compound according to claim 1, wherein $R^4$ is hydrogen or methyl; and all remaining substituents have the significances given in claim 1.

8. A compound of formula (I) according to claim 1 selected from the group consisting of:
7-(4-fluoro-phenylamino)-5,6,7,8-tetrahydro-naphthalene-2-carboxylic acid hydroxyamide;
7-(4-bromo-phenylamino)-5,6,7,8-tetrahydro-naphthalene-2-carboxylic acid hydroxyamide;
7-(4-nitro-phenylamino)-5,6,7,8-tetrahydro-naphthalene-2-carboxylic acid hydroxyamide;
7-(3-chloro-4-cyano-phenylamino)-5,6,7,8-tetrahydro-naphthalene-2-carboxylic acid hydroxyamide;
7-(pyridin-2-ylamino)-5,6,7,8-tetrahydro-naphthalene-2-carboxylic acid hydroxyamide;
7-(5-nitro-pyridin-2-ylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide; and
7-(4-Phenyl-pyrimidin-2-ylamino)-5,6,7,8-tetrahydro-naphthalene-2-carboxylic acid hydroxyamide.

9. A compound of formula (I) according to claim 1 selected from the group consisting of:
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(4-chloro-phenyl)-pyrimidin-2-ylamino]-5,6,7,8-tetrahydro-naphthalene-2-carboxylic acid hydroxyamide;
7-[4-(3-chloro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide;
7-[4-(2-fluoro-4-methyl-phenyl)-pyrimidin-2-ylamino]-5,6,7,8-tetrahydro-naphthalene-2-carboxylic acid hydroxyamide;
7-[4-(2,4-Dimethoxy-phenyl)-pyrimidin-2-ylamino]-5,6,7,8-tetrahydro-naphthalene-2-carboxylic acid hydroxyamide;
7-[4-(4-Trifluoromethyl-phenyl)-pyrimidin-2-ylamino]-5,6,7,8-tetrahydro-naphthalene-2-carboxylic acid hydroxyamide; and
7-[4-(2,4-Dichloro-phenyl)-pyrimidin-2-ylamino]-5,6,7,8-tetrahydro-naphthalene-2-carboxylic acid hydroxyamide.

10. A compound of formula (I) according to claim 1 selected from the group consisting of:
7-[4-(4-chloro-2-methyl-phenyl)-pyrimidin-2-ylamino]-5,6,7,8-tetrahydro-naphthalene-2-carboxylic acid hydroxyamide;
7-[4-(3-Chloro-4-fluoro-phenyl)-pyrimidin-2-ylamino]-5,6,7,8-tetrahydro-naphthalene-2-carboxylic acid hydroxyamide;
7-[4-(4-Phenoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Methoxy-pyridin-3-yl)-pyrimidin-2-ylamino]-5,6,7,8-tetrahydro-naphthalene-2-carboxylic acid hydroxyamide;
7-[4-(6-Chloro-pyridin-3-yl)-pyrimidin-2-ylamino]-5,6,7,8-tetrahydro-naphthalene-2-carboxylic acid hydroxyamide; and
7-[4-(2-Chloro-pyridin-3-yl)-pyrimidin-2-ylamino]-5,6,7,8-tetrahydro-naphthalene-2-carboxylic acid hydroxyamide.

11. A compound of formula (I) according to claim 1 selected from the group consisting of:

7-[4-(6-Morpholin-pyridin-3-yl)-pyrimidin-2-ylamino]-5,6,7,8-tetrahydro-naphthalene-2-carboxylic acid hydroxyamide;

7-(4-Methyl-6-phenoxy-pyrimidin-2-ylamino)-5,6,7,8-tetrahydro-naphthalene-2-carboxylic acid hydroxyamide;

7-(4-Naphthalen-2-yl-pyrimidin-2-ylamino)-5,6,7,8-tetrahydro-naphthalene-2-carboxylic acid hydroxyamide;

7-(4-Quinolin-3-yl-pyrimidin-2-ylamino)-5,6,7,8-tetrahydro-naphthalene-2-carboxylic acid hydroxyamide;

7-(6-Fluoro-quinazolin-2-ylamino)-5,6,7,8-tetrahydro-naphthalene-2-carboxylic acid hydroxyamide;

7-[Methyl-(4-pyridin-3-ylpyrimidin-2-yl)-amino]-5,6,7,8-tetrahydro-naphthalene-2-carboxylic acid hydroxyamide;

7-(3-Pyridin-3-yl-acryloylamino)-5,6,7,8-tetrahydro-naphthalene-2-carboxylic acid hydroxyamide;

7-(Hydroxycarbamoyl-1,2,3,4-tetrahydro-naphthalen-2-yl)-carbamic acid pyridin-3-ylmethyl ester;

7-(Butane-1-sulfonylamino)-5,6,7,8-tetrahydro-naphthalene-2-carboxylic acid hydroxyamide; and 7-(3-Fluoro-benzenesulfonylamino)-5,6,7,8-tetrahydro-naphthalene-2-carboxylic acid hydroxyamide.

12. A compound of formula (I) according to claim 1 selected from the group consisting of:
7-(4-Chloro-benzenesulfonylamino)-5,6,7,8-tetrahydro-naphthalene-2-carboxylic acid hydroxyamide;
7-(3-Chloro-benzenesulfonylamino)-5,6,7,8-tetrahydro-naphthalene-2-carboxylic acid hydroxyamide;
7-(3-Trifluoromethyl-benzenesulfonylamino)-5,6,7,8-tetrahydro-naphthalene-2-carboxylic acid hydroxyamide;
7-(2,4-Difluoro-benzenesulfonylamino)-5,6,7,8-tetrahydro-naphthalene-2-carboxylic acid hydroxyamide;
7-(3,4-Dimethoxy-benzenesulfonylamino)-5,6,7,8-tetrahydro-naphthalene-2-carboxylic acid hydroxyamide;
7-(2,4-Dichloro-benzenesulfonylamino)-5,6,7,8-tetrahydro-naphthalene-2-carboxylic acid hydroxyamide;
7-(3,4-Dichloro-benzenesulfonylamino)-5,6,7,8-tetrahydro-naphthalene-2-carboxylic acid hydroxyamide;
7-(Pyridine-3-sulfonylamino)-5,6,7,8-tetrahydro-naphthalene-2-carboxylic acid hydroxyamide;
3-Fluoro-7-(pyrimidin-2-ylamino)-5,6,7,8-tetrahydro-naphthalene-2-carboxylic acid hydroxyamide; and
3-Fluoro-7-(4-phenyl-pyrimidin-2-ylamino)-5,6,7,8-tetrahydro-naphthalene-2-carboxylic acid hydroxyamide.

13. A compound of formula (I) according to claim 1 selected from the group consisting of:
7-(4-Chloro-benzenesulfonylamino)-3-fluoro-5,6,7,8-tetrahydro-naphthalene-2-carboxylic acid hydroxyamide;
7-(3-Chloro-benzenesulfonylamino)-3-fluoro-5,6,7,8-tetrahydro-naphthalene-2-carboxylic acid hydroxyamide;
3-(Pyridin-3-yl-pyrimidine-2-ylamino)-1,2,3,4-tetrahydro-quinoline-6-carboxylic acid hydroxyamide;
3-(3-Methoxy-benzoylamino)-1,2,3,4-tetrahydro-quinoline-6-carboxylic acid hydroxyamide;
3-(4-Chloro-benzoylamino)-1,2,3,4-tetrahydro-quinoline-6-carboxylic acid hydroxyamide;
3-(3-Chloro-benzoylamino)-1,2,3,4-tetrahydro-quinoline-6-carboxylic acid hydroxyamide;
3-(3-Trifluoromethyl-benzoylamino)-1,2,3,4-tetrahydro-quinoline-6-carboxylic acid hydroxyamide;
3-(3,4-Dichloro-benzoylamino)-1,2,3,4-tetrahydro-quinoline-6-carboxylic acid hydroxyamide;
3-[(Biphenyl-4-carbonyl)-amino]-1,2,3,4-tetrahydro-quinoline-6-carboxylic acid hydroxyamide; and
3-(3-Fluoro-benzenesulfonylamino)-1,2,3,4-tetrahydro-quinoline-6-carboxylic acid hydroxyamide.

14. A compound of formula (I) according to claim 1 selected from the group consisting of:
3-(3-Chloro-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide;
3-(3-Trifluoromethyl-benzenesulfonylamino)-1,2,3,4-tetrahydro-quinoline-6-carboxylic acid hydroxyamide;
3-(3,4-Dimethoxy-benzenesulfonylamino)-1,2,3,4-tetrahydro-quinoline-6-carboxylic acid hydroxyamide;
3-(4-Chloro-benzenesulfonylamino)-1,2,3,4-tetrahydro-quinoline-6-carboxylic acid hydroxyamide; and
3-(4-Pyridin-3-yl-pyrimidin-2-ylamino)-chroman-6-6-carboxylic acid hydroxyamide.

15. A compound of formula (I) according to claim 1 selected from
7-(4-bromo-phenylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide;
7-(4-Phenyl-pyrimidin-2-ylamino)-5,6,7,8-tetrahydro-naphthalene-2-carboxylic acid hydroxyamide;
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide; and
7-[4-(2-fluoro-4-methyl-phenyl)-pyrimidin-2-ylamino]-5,6,7,8-tetrahydro-naphthalene-2-carboxylic acid hydroxyamide.

16. A compound of formula (I) according to claim 1 selected from the group consisting of:
7-[4-(2,4-Dimethoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Chloro-pyridin-3-yl)-pyrimidin-2-ylamino]-5,6,7,8-tetrahydro-naphthalene-2-carboxylic acid hydroxyamide;
7-[4-(2-Chloro-pyridin-3-yl)-pyrimidin-2-ylamino]-5,6,7,8-tetrahydro-naphthalene-2-carboxylic acid hydroxyamide;
7-[4-(6-Morpholin-pyridin-3-yl)-pyrimidin-2-ylamino]-5,6,7,8-tetrahydro-naphthalene-2-carboxylic acid hydroxyamide;
7-(4-Quinolin-3-yl-pyrimidin-2-ylamino)-5,6,7,8-tetrahydro-naphthalene-2-carboxylic acid hydroxyamide; and 7-(6-Fluoro-quinazolin-2-ylamino)-5,6,7,8-tetrahydro-naphthalene-2-carboxylic acid hydroxyamide.

17. A compound of formula (I) according to claim 1 selected from the group consisting of:
- 7-(Hydroxycarbamoyl-1,2,3,4-tetrahydro-naphthalen-2-yl)-carbamic acid pyridin-3-ylmethyl ester;
- 7-(Butane-1-sulfonylamino)-5,6,7,8-tetrahydro-naphthalene-2-carboxylic acid hydroxyamide;
- 7-(3-Fluoro-benzenesulfonylamino)-5,6,7,8-tetrahydro-naphthalene-2-carboxylic acid hydroxyamide;
- 7-(4-Chloro-benzenesulfonylamino)-5,6,7,8-tetrahydro-naphthalene-2-carboxylic acid hydroxyamide;
- 7-(3-Chloro-benzenesulfonylamino)-5,6,7,8-tetrahydro-naphthalene-2-carboxylic acid hydroxyamide;
- 7-(3-Trifluoromethyl-benzenesulfonylamino)-5,6,7,8-tetrahydro-naphthalene-2-carboxylic acid hydroxyamide;
- 7-(2,4-Difluoro-benzenesulfonylamino)-5,6,7,8-tetrahydro-naphthalene-2-carboxylic acid hydroxyamide;
- 7-(3,4-Dimethoxy-benzenesulfonylamino)-5,6,7,8-tetrahydro-naphthalene-2-carboxylic acid hydroxyamide;
- 7-(3,4-Dichloro-benzenesulfonylamino)-5,6,7,8-tetrahydro-naphthalene-2-carboxylic acid hydroxyamide; and
- 3-Fluoro-7-(4-phenyl-pyrimidin-2-ylamino)-5,6,7,8-tetrahydro-naphthalene-2-carboxylic acid hydroxyamide.

18. A compound of formula (I) according to claim 1 selected from the group consisting of:
- 7-(3-Chloro-benzenesulfonylamino)-3-fluoro-5,6,7,8-tetrahydro-naphthalene-2-carboxylic acid hydroxyamide;
- 3-(Pyridin-3-yl-pyrimidine-2-ylamino)-1,2,3,4-tetrahydro-quinoline-6-carboxylic acid hydroxyamide;
- 3-(3-Methoxy-benzoylamino)-1,2,3,4-tetrahydro-quinoline-6-carboxylic acid hydroxyamide;
- 3-(3-Fluoro-benzenesulfonylamino)-1,2,3,4-tetrahydro-quinoline-6-carboxylic acid hydroxyamide;
- 3-(3-Chloro-benzenesulfonylamino)-1,2,3,4-tetrahydro-quinoline-6-carboxylic acid hydroxyamide;
- 3-(3,4-Dimethoxy-benzenesulfonylamino)-1,2,3,4-tetrahydro-quinoline-6-carboxylic acid hydroxyamide;
- 3-(4-Chloro-benzenesulfonylamino)-1,2,3,4-tetrahydro-quinoline-6-carboxylic acid hydroxyamide; and
- 3-(4-Pyridin-3-yl-pyrimidin-2-ylamino)-chroman-6-6-carboxylic acid hydroxyamide.

19. A compound of formula (I) according to claim 1 selected from the group consisting of:
- 7-(4-fluoro-phenylamino)-5,6,7,8-tetrahydro-naphthalene-2-carboxylic acid hydroxyamide;
- 7-(4-bromo-phenylamino)-5,6,7,8-tetrahydro-naphthalene-2-carboxylic acid hydroxyamide;
- 7-(4-nitro-phenylamino)-5,6,7,8-tetrahydro-naphthalene-2-carboxylic acid hydroxyamide;
- 7-(3-chloro-4-cyano-phenylamino)-5,6,7,8-tetrahydro-naphthalene-2-carboxylic acid hydroxyamide;
- 7-(pyridin-2-ylamino)-5,6,7,8-tetrahydro-naphthalene-2-carboxylic acid hydroxyamide;
- 7-(5-nitro-pyridin-2-ylamino)-5,6,7,8-tetrahydro-naphthalene-2-carboxylic acid hydroxyamide;
- 7-(Pyrimidin-2-ylamino)-5,6,7,8-tetrahydro-naphthalene-2-carboxylic acid hydroxyamide;
- 7-(4-trifluoromethyl-pyrimidin-2-ylamino)-5,6,7,8-tetrahydro-naphthalene-2-carboxylic acid hydroxyamide;
- 7-(4-Methoxy-6-methyl-pyrimidin-2-ylamino)-5,6,7,8-tetrahydro-naphthalene-2-carboxylic acid hydroxyamide; and
- 7-(4-Phenyl-pyrimidin-2-ylamino)-5,6,7,8-tetrahydro-naphthalene-2-carboxylic acid hydroxyamide.

20. A compound of formula (I) according to claim 1 selected from the group consisting of:
- 7-(4-p-Tolyl-pyrimidin-2-ylamino)-5,6,7,8-tetrahydro-naphthalene-2-carboxylic acid hydroxyamide;
- 7-[4-(4-fluoro-phenyl)-pyrimidin-2-ylamino]-5,6,7,8-tetrahydro-naphthalene-2-carboxylic acid hydroxyamide;
- 7-[4-(4-chloro-phenyl)-pyrimidin-2-ylamino]-5,6,7,8-tetrahydro-naphthalene-2-carboxylic acid hydroxyamide;
- 7-[4-(3-chloro-phenyl)-pyrimidin-2-ylamino]-5,6,7,8-tetrahydro-naphthalene-2-carboxylic acid hydroxyamide;
- 7-[4-(2-chloro-phenyl)-pyrimidin-2-ylamino]-5,6,7,8-tetrahydro-naphthalene-2-carboxylic acid hydroxyamide;
- 7-[4-(3-Dimethylamino-phenyl)-pyrimidin-2-ylamino]-5,6,7,8-tetrahydro-naphthalene-2-carboxylic acid hydroxyamide;
- 7-[4-(2-fluoro-4-methyl-phenyl)-pyrimidin-2-ylamino]-5,6,7,8-tetrahydro-naphthalene-2-carboxylic acid hydroxyamide;
- 7-[4-(2,4-Dimethoxy-phenyl)-pyrimidin-2-ylamino]-5,6,7,8-tetrahydro-naphthalene-2-carboxylic acid hydroxyamide;
- 7-[4-(4-Trifluoromethyl-phenyl)-pyrimidin-2-ylamino]-5,6,7,8-tetrahydro-naphthalene-2-carboxylic acid hydroxyamide; and
- 7-[4-(2,4-Dichloro-phenyl)-pyrimidin-2-ylamino]-5,6,7,8-tetrahydro-naphthalene-2-carboxylic acid hydroxyamide.

21. A compound of formula (I) according to claim 1 selected from the group consisting of:
- 7-[4-(4-chloro-2-methyl-phenyl)-pyrimidin-2-ylamino]-5,6,7,8-tetrahydro-naphthalene-2-carboxylic acid hydroxyamide;
- 7-[4-(3-Chloro-4-fluoro-phenyl)-pyrimidin-2-ylamino]-5,6,7,8-tetrahydro-naphthalene-2-carboxylic acid hydroxyamide;
- 7-[4-(4-Phenoxy-phenyl)-pyrimidin-2-ylamino]-5,6,7,8-tetrahydro-naphthalene-2-carboxylic acid hydroxyamide;
- 7-(4-Pyridin-3-yl-pyrimidin-2-ylamino)-5,6,7,8-tetrahydro-naphthalene-2-carboxylic acid hydroxyamide;
- 7-[4-(6-Methyl-pyridin-3-yl)-pyrimidin-2-ylamino]-5,6,7,8-tetrahydro-naphthalene-2-carboxylic acid hydroxyamide;
- 7-[4-(5-Methyl-pyridin-3-yl)-pyrimidin-2-ylamino]-5,6,7,8-tetrahydro-naphthalene-2-carboxylic acid hydroxyamide;
- 7-[4-(5-Methoxy-pyridin-3-yl)-pyrimidin-2-ylamino]-5,6,7,8-tetrahydro-naphthalene-2-carboxylic acid hydroxyamide;
- 7-[4-(6-Methoxy-pyridin-3-yl)-pyrimidin-2-ylamino]-5,6,7,8-tetrahydro-naphthalene-2-carboxylic acid hydroxyamide;
- 7-[4-(6-Chloro-pyridin-3-yl)-pyrimidin-2-ylamino]-5,6,7,8-tetrahydro-naphthalene-2-carboxylic acid hydroxyamide; and
- 7-[4-(2-Chloro-pyridin-3-yl)-pyrimidin-2-ylamino]-5,6,7,8-tetrahydro-naphthalene-2-carboxylic acid hydroxyamide.

22. A compound of formula (I) according to claim 1 selected from the group consisting of:
- 7-[4-(6-Morpholin-pyridin-3-yl)-pyrimidin-2-ylamino]-5,6,7,8-tetrahydro-naphthalene-2-carboxylic acid hydroxyamide;
- 7-(4-Methyl-6-phenoxy-pyrimidin-2-ylamino)-5,6,7,8-tetrahydro-naphthalene-2-carboxylic acid hydroxyamide;
- 7-(4-Naphthalen-2-yl-pyrimidin-2-ylamino)-5,6,7,8-tetrahydro-naphthalene-2-carboxylic acid hydroxyamide;

7-(4-Quinolin-3-yl-pyrimidin-2-ylamino)-5,6,7,8-tetrahydro-naphthalene-2-carboxylic acid hydroxyamide;
7-(6-Fluoro-quinazolin-2-ylamino)-5,6,7,8-tetrahydro-naphthalene-2-carboxylic acid hydroxyamide;
7-[Methyl-(4-pyridin-3-ylpyrimidin-2-yl)-amino]-5,6,7,8-tetrahydro-naphthalene-2-carboxylic acid hydroxyamide;
7-(Hydroxycarbamoyl-1,2,3,4-tetrahydro-naphthalen-2-yl)-carbamic acid pyridin-3-ylmethyl ester;
7-(Butane-1-sulfonylamino)-5,6,7,8-tetrahydro-naphthalene-2-carboxylic acid hydroxyamide;
7-(3-Fluoro-benzenesulfonylamino)-5,6,7,8-tetrahydro-naphthalene-2-carboxylic acid hydroxyamide; and
7-(4-Chloro-benzenesulfonylamino)-5,6,7,8-tetrahydro-naphthalene-2-carboxylic acid hydroxyamide.

23. A compound of formula (I) according to claim 1 selected from the group consisting of:
7-(3-Chloro-benzenesulfonylamino)-5,6,7,8-tetrahydro-naphthalene-2-carboxylic acid hydroxyamide;
7-(3-Trifluoromethyl-benzenesulfonylamino)-5,6,7,8-tetrahydro-naphthalene-2-carboxylic acid hydroxyamide;
7-(2,4-Difluoro-benzenesulfonylamino)-5,6,7,8-tetrahydro-naphthalene-2-carboxylic acid hydroxyamide;
7-(3,4-Dimethoxy-benzenesulfonylamino)-5,6,7,8-tetrahydro-naphthalene-2-carboxylic acid hydroxyamide;
7-(2,4-Dichloro-benzenesulfonylamino)-5,6,7,8-tetrahydro-naphthalene-2-carboxylic acid hydroxyamide;
7-(3,4-Dichloro-benzenesulfonylamino)-5,6,7,8-tetrahydro-naphthalene-2-carboxylic acid hydroxyamide;
7-(Pyridine-3-sulfonylamino)-5,6,7,8-tetrahydro-naphthalene-2-carboxylic acid hydroxyamide;
3-Fluoro-7-(pyrimidin-2-ylamino)-5,6,7,8-tetrahydro-naphthalene-2-carboxylic acid hydroxyamide;
3-Fluoro-7-(4-phenyl-pyrimidin-2-ylamino)-5,6,7,8-tetrahydro-naphthalene-2-carboxylic acid hydroxyamide; and
7-(4-Chloro-benzenesulfonylamino)-3-fluoro-5,6,7,8-tetrahydro-naphthalene-2-carboxylic acid hydroxyamide.

24. A compound of formula (I) according to claim 1 selected from the group consisting of:
7-(3-Chloro-benzenesulfonylamino)-3-fluoro-5,6,7,8-tetrahydro-naphthalene-2-carboxylic acid hydroxyamide;
3-(Pyridin-3-yl-pyrimidine-2-ylamino)-1,2,3,4-tetrahydro-quinoline-6-carboxylic acid hydroxyamide;
3-(3-Methoxy-benzoylamino)-1,2,3,4-tetrahydro-quinoline-6-carboxylic acid hydroxyamide;
3-(4-Chloro-benzoylamino)-1,2,3,4-tetrahydro-quinoline-6-carboxylic acid hydroxyamide;
3-(3-Chloro-benzoylamino)-1,2,3,4-tetrahydro-quinoline-6-carboxylic acid hydroxyamide;
3-(3-Trifluoromethyl-benzoylamino)-1,2,3,4-tetrahydro-quinoline-6-carboxylic acid hydroxyamide;
3-(3,4-Dichloro-benzoylamino)-1,2,3,4-tetrahydro-quinoline-6-carboxylic acid hydroxyamide;
3-[(Biphenyl-4-carbonyl)-amino]-1,2,3,4-tetrahydro-quinoline-6-carboxylic acid hydroxyamide; and
3-(4-Chloro-benzenesulfonylamino)-1,2,3,4-tetrahydro-quinoline-6-carboxylic acid hydroxyamide.

25. A compound of formula (I) according to claim 1 selected from
7-(4-fluoro-phenylamino)-5,6,7,8-tetrahydro-naphthalene-2-carboxylic acid hydroxyamide;
7-(4-bromo-phenylamino)-5,6,7,8-tetrahydro-naphthalene-2-carboxylic acid hydroxyamide;
7-(4-nitro-phenylamino)-5,6,7,8-tetrahydro-naphthalene-2-carboxylic acid hydroxyamide;
7-(3-chloro-4-cyano-phenylamino)-5,6,7,8-tetrahydro-naphthalene-2-carboxylic acid hydroxyamide;
7-(pyridin-2-ylamino)-5,6,7,8-tetrahydro-naphthalene-2-carboxylic acid hydroxyamide;
7-(5-nitro-pyridin-2-ylamino)-5,6,7,8-tetrahydro-naphthalene-2-carboxylic acid hydroxyamide;
7-(Pyrimidin-2-ylamino)-5,6,7,8-tetrahydro-naphthalene-2-carboxylic acid hydroxyamide;
7-(4-trifluoromethyl-pyrimidin-2-ylamino)-5,6,7,8-tetrahydro-naphthalene-2-carboxylic acid hydroxyamide;
7-(4-Methoxy-6-methyl-pyrimidin-2-ylamino)-5,6,7,8-tetrahydro-naphthalene-2-carboxylic acid hydroxyamide; and
7-(4-Phenyl-pyrimidin-2-ylamino)-5,6,7,8-tetrahydro-naphthalene-2-carboxylic acid hydroxyamide.

26. A compound of formula (I) according to claim 1 selected from the group consisting of:
7-(4-p-Tolyl-pyrimidin-2-ylamino)-5,6,7,8-tetrahydro-naphthalene-2-carboxylic acid hydroxyamide;
7-[4-(4-fluoro-phenyl)-pyrimidin-2-ylamino]-5,6,7,8-tetrahydro-naphthalene-2-carboxylic acid hydroxyamide;
7-[4-(4-chloro-phenyl)-pyrimidin-2-ylamino]-5,6,7,8-tetrahydro-naphthalene-2-carboxylic acid hydroxyamide;
7-[4-(3-chloro-phenyl)-pyrimidin-2-ylamino]-5,6,7,8-tetrahydro-naphthalene-2-carboxylic acid hydroxyamide;
7-[4-(2-chloro-phenyl)-pyrimidin-2-ylamino]-5,6,7,8-tetrahydro-naphthalene-2-carboxylic acid hydroxyamide;
7-[4-(3-Dimethylamino-phenyl)-pyrimidin-2-ylamino]-5,6,7,8-tetrahydro-naphthalene-2-carboxylic acid hydroxyamide;
7-[4-(2-fluoro-4-methyl-phenyl)-pyrimidin-2-ylamino]-5,6,7,8-tetrahydro-naphthalene-2-carboxylic acid hydroxyamide;
7-[4-(2,4-Dimethoxy-phenyl)-pyrimidin-2-ylamino]-5,6,7,8-tetrahydro-naphthalene-2-carboxylic acid hydroxyamide;
7-[4-(4-Trifluoromethyl-phenyl)-pyrimidin-2-ylamino]-5,6,7,8-tetrahydro-naphthalene-2-carboxylic acid hydroxyamide; and
7-[4-(2,4-Dichloro-phenyl)-pyrimidin-2-ylamino]-5,6,7,8-tetrahydro-naphthalene-2-carboxylic acid hydroxyamide.

27. A compound of formula (I) according to claim 1 selected from the group consisting of:
7-[4-(4-chloro-2-methyl-phenyl)-pyrimidin-2-ylamino]-5,6,7,8-tetrahydro-naphthalene-2-carboxylic acid hydroxyamide;
7-[4-(3-Chloro-4-fluoro-phenyl)-pyrimidin-2-ylamino]-5,6,7,8-tetrahydro-naphthalene-2-carboxylic acid hydroxyamide;
7-[4-(4-Phenoxy-phenyl)-pyrimidin-2-ylamino]-5,6,7,8-tetrahydro-naphthalene-2-carboxylic acid hydroxyamide;
7-(4-Pyridin-3-yl-pyrimidin-2-ylamino)-5,6,7,8-tetrahydro-naphthalene-2-carboxylic acid hydroxyamide;
7-[4-(6-Methyl-pyridin-3-yl)-pyrimidin-2-ylamino]-5,6,7,8-tetrahydro-naphthalene-2-carboxylic acid hydroxyamide;
7-[4-(5-Methyl-pyridin-3-yl)-pyrimidin-2-ylamino]-5,6,7,8-tetrahydro-naphthalene-2-carboxylic acid hydroxyamide;
7-[4-(5-Methoxy-pyridin-3-yl)-pyrimidin-2-ylamino]-5,6,7,8-tetrahydro-naphthalene-2-carboxylic acid hydroxyamide;
7-[4-(6-Methoxy-pyridin-3-yl)-pyrimidin-2-ylamino]-5,6,7,8-tetrahydro-naphthalene-2-carboxylic acid hydroxyamide;

7-[4-(6-Chloro-pyridin-3-yl)-pyrimidin-2-ylamino]-5,6,7,8-tetrahydro-naphthalene-2-carboxylic acid hydroxyamide;

7-[4-(2-Chloro-pyridin-3-yl)-pyrimidin-2-ylamino]-5,6,7,8-tetrahydro-naphthalene-2-carboxylic acid hydroxyamide; and 7-[4-(6-Morpholin-pyridin-3-yl)-pyrimidin-2-ylamino]-5,6,7,8-tetrahydro-naphthalene-2-carboxylic acid hydroxyamide.

28. A compound of formula (I) according to claim 1 selected from the group consisting of:

7-(4-Methyl-6-phenoxy-pyrimidin-2-ylamino)-5,6,7,8-tetrahydro-naphthalene-2-carboxylic acid hydroxyamide;

7-(4-Naphthalen-2-yl-pyrimidin-2-ylamino)-5,6,7,8-tetrahydro-naphthalene-2-carboxylic acid hydroxyamide;

7-(4-Quinolin-3-yl-pyrimidin-2-ylamino)-5,6,7,8-tetrahydro-naphthalene-2-carboxylic acid hydroxyamide;

7-(6-Fluoro-quinazolin-2-ylamino)-5,6,7,8-tetrahydro-naphthalene-2-carboxylic acid hydroxyamide;

7-[Methyl-(4-pyridin-3-ylpyrimidin-2-yl)-amino]-5,6,7,8-tetrahydro-naphthalene-2-carboxylic acid hydroxyamide;

7-(3-Pyridin-3-yl-acryloylamino)-5,6,7,8-tetrahydro-naphthalene-2-carboxylic acid hydroxyamide;

7-(Hydroxycarbamoyl-1,2,3,4-tetrahydro-naphthalen-2-yl)-carbamic acid pyridin-3-ylmethyl ester;

7-(Butane-1-sulfonylamino)-5,6,7,8-tetrahydro-naphthalene-2-carboxylic acid hydroxyamide;

7-(3-Fluoro-benzenesulfonylamino)-5,6,7,8-tetrahydro-naphthalene-2-carboxylic acid hydroxyamide; and 7-(4-Chloro-benzenesulfonylamino)-5,6,7,8-tetrahydro-naphthalene-2-carboxylic acid hydroxyamide.

29. A compound of formula (I) according to claim 1 selected from the group consisting of:

7-(3-Chloro-benzenesulfonylamino)-5,6,7,8-tetrahydro-naphthalene-2-carboxylic acid hydroxyamide;

7-(3-Trifluoromethyl-benzenesulfonylamino)-5,6,7,8-tetrahydro-naphthalene-2-carboxylic acid hydroxyamide;

7-(2,4-Difluoro-benzenesulfonylamino)-5,6,7,8-tetrahydro-naphthalene-2-carboxylic acid hydroxyamide;

7-(3,4-Dimethoxy-benzenesulfonylamino)-5,6,7,8-tetrahydro-naphthalene-2-carboxylic acid hydroxyamide;

7-(2,4-Dichloro-benzenesulfonylamino)-5,6,7,8-tetrahydro-naphthalene-2-carboxylic acid hydroxyamide;

7-(3,4-Dichloro-benzenesulfonylamino)-5,6,7,8-tetrahydro-naphthalene-2-carboxylic acid hydroxyamide;

7-(Pyridine-3-sulfonylamino)-5,6,7,8-tetrahydro-naphthalene-2-carboxylic acid hydroxyamide;

3-Fluoro-7-(4-phenyl-pyrimidin-2-ylamino)-5,6,7,8-tetrahydro-naphthalene-2-carboxylic acid hydroxyamide;

7-(4-Chloro-benzenesulfonylamino)-3-fluoro-5,6,7,8-tetrahydro-naphthalene-2-carboxylic acid hydroxyamide; and 7-(3-Chloro-benzenesulfonylamino)-3-fluoro-5,6,7,8-tetrahydro-naphthalene-2-carboxylic acid hydroxyamide.

30. A compound of formula (I) according to claim 1 selected from the group consisting of:

3-(Pyridin-3-yl-pyrimidine-2-ylamino)-1,2,3,4-tetrahydro-quinoline-6-carboxylic acid hydroxyamide;

3-(3-Methoxy-benzoylamino)-1,2,3,4-tetrahydro-quinoline-6-carboxylic acid hydroxyamide;

3-(4-Chloro-benzoylamino)-1,2,3,4-tetrahydro-quinoline-6-carboxylic acid hydroxyamide;

3-(3-Chloro-benzoylamino)-1,2,3,4-tetrahydro-quinoline-6-carboxylic acid hydroxyamide;

3-(3-Trifluoromethyl-benzoylamino)-1,2,3,4-tetrahydro-quinoline-6-carboxylic acid hydroxyamide;

3-(3,4-Dichloro-benzoylamino)-1,2,3,4-tetrahydro-quinoline-6-carboxylic acid hydroxyamide;

3-[(Biphenyl-4-carbonyl)-amino]-1,2,3,4-tetrahydro-quinoline-6-carboxylic acid hydroxyamide;

3-(3-Fluoro-benzenesulfonylamino)-1,2,3,4-tetrahydro-quinoline-6-carboxylic acid hydroxyamide;

3-(3-Chloro-benzenesulfonylamino)-1,2,3,4-tetrahydro-quinoline-6-carboxylic acid hydroxyamide; and 3-(4-Chloro-benzenesulfonylamino)-1,2,3,4-tetrahydro-quinoline-6-carboxylic acid hydroxyamide.

31. A compound of formula (I) according to claim 1 selected from the group consisting of:

3-(3-Trifluoromethyl-benzenesulfonylamino)-1,2,3,4-tetrahydro-quinoline-6-carboxylic acid hydroxyamide;

3-(3,4-Dimethoxy-benzenesulfonylamino)-1,2,3,4-tetrahydro-quinoline-6-carboxylic acid hydroxyamide;

3-(4-Chloro-benzenesulfonylamino)-1,2,3,4-tetrahydro-quinoline-6-carboxylic acid hydroxyamide; and 3-(4-Pyridin-3-yl-pyrimidin-2-ylamino)-chroman-6-6-carboxylic acid hydroxyamide.

32. A pharmaceutical composition comprising a compound in accordance with claim 1 and a therapeutically inert carrier.

* * * * *